United States Patent
Urano et al.

(10) Patent No.: US 10,114,287 B2
(45) Date of Patent: Oct. 30, 2018

(54) SILICONE SKELETON-CONTAINING POLYMER COMPOUND AND METHOD FOR PRODUCING SAME, CHEMICALLY AMPLIFIED NEGATIVE RESIST COMPOSITION, PHOTO-CURABLE DRY FILM AND METHOD FOR PRODUCING SAME, PATTERNING PROCESS, LAYERED PRODUCT, AND SUBSTRATE

(71) Applicant: SHIN-ETSU CHEMICAL CO., LTD., Chiyoda-ku (JP)

(72) Inventors: Hiroyuki Urano, Jyoetsu (JP); Masashi Iio, Jyoetsu (JP); Katsuya Takemura, Jyoetsu (JP); Koji Hasegawa, Jyoetsu (JP); Masahiro Fukushima, Jyoetsu (JP); Takayuki Fujiwara, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 356 days.

(21) Appl. No.: 14/855,163

(22) Filed: Sep. 15, 2015

(65) Prior Publication Data

US 2016/0097973 A1    Apr. 7, 2016

(30) Foreign Application Priority Data

Oct. 2, 2014 (JP) ................................. 2014-204210
May 8, 2015 (JP) ................................... 2015-95564

(51) Int. Cl.
*G03F 7/004* (2006.01)
*G03F 7/075* (2006.01)
(Continued)

(52) U.S. Cl.
CPC ............ *G03F 7/0757* (2013.01); *C07C 39/21* (2013.01); *C08G 77/16* (2013.01); *C08G 77/18* (2013.01);
(Continued)

(58) Field of Classification Search
CPC ...... G03F 7/0757; G03F 7/168; G03F 7/2002; G03F 7/2037; G03F 7/32; G03F 7/38;
(Continued)

(56) References Cited

U.S. PATENT DOCUMENTS 3,159,601 A    12/1964    Ashby
3,159,662 A    12/1964    Ashby
(Continued)

FOREIGN PATENT DOCUMENTS

JP    2008-184571 A    8/2008
JP    2009-200315 A    9/2009

OTHER PUBLICATIONS

Oct. 30, 2015 Extended European Search Report issued in Patent Application No. 15002687.0.

*Primary Examiner* — Amanda C. Walke
(74) *Attorney, Agent, or Firm* — Oliff PLC

(57) ABSTRACT

The present invention provides a silicone skeleton-containing polymer compound containing a repeating unit shown by the general formula (1) and having a weight average molecular weight of 3,000 to 500,000. There can be provided a silicone skeleton-containing polymer compound suitable used as a base resin of a chemically amplified negative resist composition that can remedy the problem of delamination generated on a metal wiring such as Cu and Al, an electrode, and a substrate, especially on a substrate such as SiN, and can form a fine pattern without generating a scum and a footing profile in the pattern bottom and on the substrate when the widely used 2.38% TMAH aqueous solution is used as a developer.

(Continued)

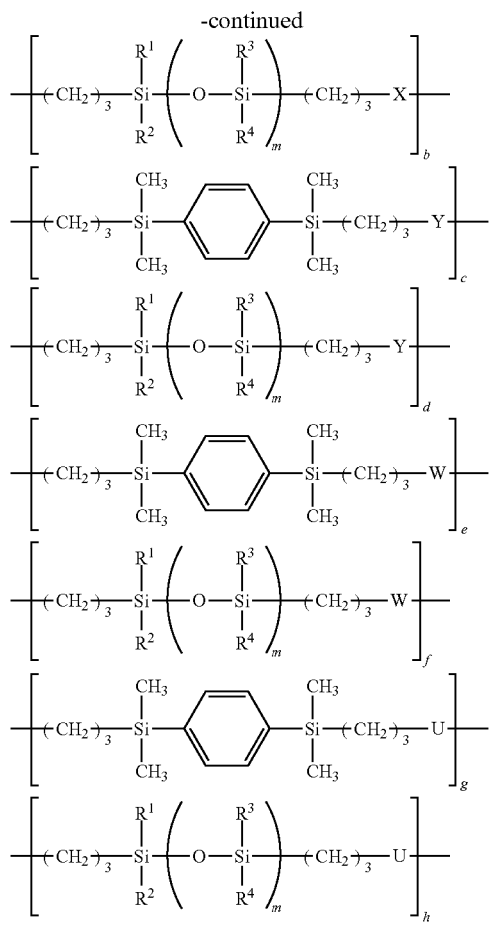

-continued

32 Claims, 1 Drawing Sheet

(51) Int. Cl.
 *G03F 7/20* (2006.01)
 *G03F 7/32* (2006.01)
 *C09D 183/14* (2006.01)
 *C08L 83/14* (2006.01)
 *C07C 39/21* (2006.01)
 *H01L 21/027* (2006.01)
 *C08G 77/52* (2006.01)
 *C08G 77/38* (2006.01)
 *C08G 77/16* (2006.01)
 *C08G 77/18* (2006.01)
 *G03F 7/16* (2006.01)
 *G03F 7/38* (2006.01)
 *G03F 7/40* (2006.01)
 *C08K 5/09* (2006.01)
 *G03F 7/038* (2006.01)
 *G03F 7/11* (2006.01)
 *C08G 77/14* (2006.01)

(52) U.S. Cl.
 CPC ............. *C08G 77/38* (2013.01); *C08G 77/52* (2013.01); *C08K 5/09* (2013.01); *C08L 83/14* (2013.01); *C09D 183/14* (2013.01); *G03F 7/038* (2013.01); *G03F 7/0382* (2013.01); *G03F 7/11* (2013.01); *G03F 7/168* (2013.01); *G03F 7/2002* (2013.01); *G03F 7/2014* (2013.01); *G03F 7/2037* (2013.01); *G03F 7/32* (2013.01); *G03F 7/38* (2013.01); *G03F 7/40* (2013.01); *H01L 21/0274* (2013.01); *C08G 77/14* (2013.01)

(58) Field of Classification Search
 CPC .......... G03F 7/40; G03F 7/038; G03F 7/0382; G03F 7/09; G03F 7/11; C08G 77/52; C08G 77/12; C09D 183/14; C08L 83/14; H01L 21/312; C07C 39/21
 USPC .............................................. 430/285.1, 271.1
 See application file for complete search history.

(56) References Cited

U.S. PATENT DOCUMENTS

| | | |
|---|---|---|
| 3,220,972 A | 11/1965 | Lamoreaux |
| 3,775,452 A | 11/1973 | Karstedt |
| 9,377,689 B2 * | 6/2016 | Takemura ............... C07C 39/21 |
| 2008/0182087 A1 | 7/2008 | Kato et al. |
| 2009/0215222 A1 | 8/2009 | Arai et al. |
| 2012/0108762 A1 | 5/2012 | Kondo et al. |

* cited by examiner

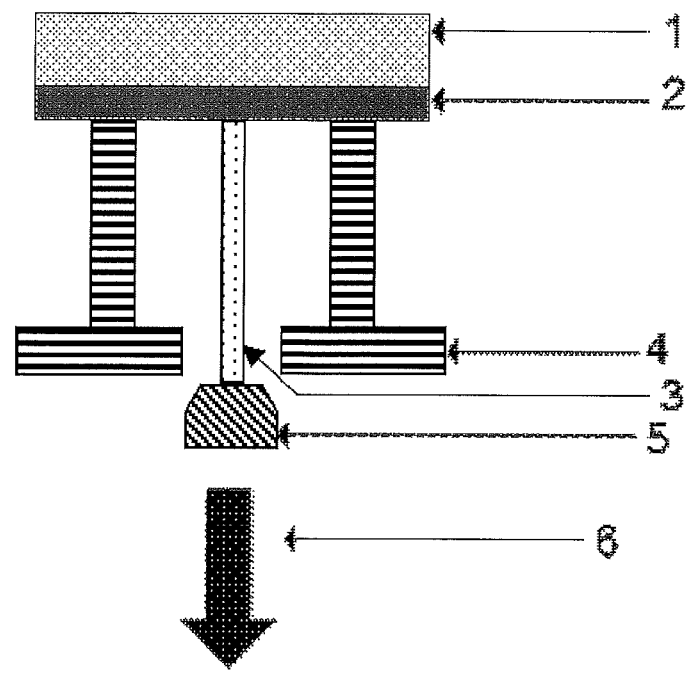

SILICONE SKELETON-CONTAINING POLYMER COMPOUND AND METHOD FOR PRODUCING SAME, CHEMICALLY AMPLIFIED NEGATIVE RESIST COMPOSITION, PHOTO-CURABLE DRY FILM AND METHOD FOR PRODUCING SAME, PATTERNING PROCESS, LAYERED PRODUCT, AND SUBSTRATE

BACKGROUND OF THE INVENTION

Field of the Invention

The present invention relates to a silicone skeleton-containing polymer compound and a method for producing the same, a chemically amplified negative resist composition using the silicone skeleton-containing polymer compound, a photo-curable dry film formed by using the chemically amplified negative resist composition and a method for producing the same, a patterning process using the chemically amplified negative resist composition or the photo-curable dry film, a layered product having the photo-curable dry film laminated on a substrate, and a substrate obtained by the patterning process.

Description of the Related Art

In accordance with progress of various electronic devices including a personal computer, a digital camera, and a mobile phone toward downsizing and higher performance, requirements are rapidly increasing for further downsizing, thinning, and higher density in a semiconductor device. Accordingly, it is desired to develop a photosensitive insulation material that can accommodate not only an increase in surface area of a substrate for the sake of higher productivity, but also structures having fine concavity and convexity with a high aspect ratio on a substrate, in high density mounting technologies including a chip size package or a chip scale package (CSP) and a three-dimensional lamination.

As to the above-mentioned photosensitive insulation material, a photo-curable resin composition has been proposed (Patent Document 1), in which the composition can be applied so as to give a wide range of film thickness by a spin coating method commonly used in the semiconductor device fabrication, can be processed into a fine pattern using a wide range of wavelength, and can be post-cured at low temperature into a top coat having excellent flexibility, heat resistance, electric characteristics, adhesiveness, reliability, and chemical resistance to protect electric and electronic parts. The spin coating method has an advantage that a film can be readily formed on a substrate.

The above-mentioned photo-curable resin composition for providing a top coat to protect electric and electronic parts is used with a film thickness of 1 to 100 μm on a substrate. However, there is a practical limit in the photo-curable resin composition because when the film thickness exceeds about 30 μm, its viscosity becomes too high to form a film on a substrate by the spin coating method.

Also, when the photo-curable resin composition is applied onto a substrate having an uneven surface by spin coating, it is difficult to form a uniform layer on the substrate. Because of this, the photo-curable resin layer tends to generate voids on the uneven part of the substrate, and thus, further improvements in planarity and step coverage have been desired. As the alternative coating method in place of the spin coating method, a spray coating method has been proposed (Patent Document 2). However, in principle, this method tends to readily cause defects such as height difference due to unevenness of the substrate, film loss at pattern edge, and a pinhole in recess bottom; and thus, the problems of planarity and step coverage still remain unsolved.

Recently, in the high density mounting technologies including a chip size package or a chip scale package (CSP) and a three-dimensional lamination, a technology by which a fine pattern having a high aspect ratio is formed on a substrate, followed by laminating the obtained pattern with a metal such as copper, whereby rewiring from a chip, is very active. As the chip advances toward higher density and higher integration, it is strongly desired in the rewiring technology to reduce the line width of a pattern and the size of a contact hole for connecting between substrates. To obtain a fine pattern, a lithography technology is generally used, and among these, a chemically amplified negative resist composition is suitable to obtain a fine pattern. Moreover, a pattern used for rewiring not only permanently exists between device chips but also needs to serve as a top coat that is curable and also has excellent flexibility, heat resistance, electric characteristics, adhesiveness, reliability, and chemical resistance to protect electric and electronic parts; and therefore, it is said that the resist composition to obtain the pattern is preferably of a negative type.

As mentioned above, a chemically amplified negative resist composition is suitable as the composition for a patterning process that is capable of processing a fine rewire and forming a top coat having excellent flexibility, heat resistance, electric characteristics, adhesiveness, reliability, and chemical resistance to protect electric and electronic parts.

On the other hand, the chemically amplified negative resist composition that is capable of forming a fine pattern to be used for processing a rewire and is useful for a top coat to protect electric and electronic parts occasionally covers over a Cu wiring that has been previously processed on a substrate or over an Al electrode on a substrate. In addition, the substrates provided with a wire and an electrode include an insulating substrate such as SiN, which needs to be covered widely. However, adhesiveness between these substrates and a covering layer formed of the chemically amplified negative resist composition is not sufficient yet, so that there often occurs a problem that the covering layer formed of the resist composition is delaminated from the substrate.

Moreover, in patterning by using the chemically amplified negative resist composition useful for a top coat to protect electric and electronic parts, an organic solvent is used often as a developer in development. In this case, the exposed part becomes insoluble in an organic solvent developer by a crosslinking reaction or the like, while the unexposed part is readily soluble in the organic solvent developer, thereby obtaining a pattern.

However, there is an idea that development by the organic solvent developer is not desirable in view of treatment of waste liquid after development, load to an environment, and so forth. Moreover, the organic solvent developer is so expensive. Therefore, development is preferably performed by an aqueous alkaline solution such as a 2.38% tetramethyl ammonium hydroxide (TMAH) aqueous solution, which is cheap and widely used in lithography patterning.

In development using an aqueous alkaline solution such as a 2.38% TMAH aqueous solution, some negative resist compositions used in recent years exhibit small difference in solubility in the developer between the exposed part and the unexposed part. In other words, the so-called dissolution contrast therebetween is sometimes small. When the dissolution contrast is small, it cannot be always expected to form a good pattern satisfying a demand of a fine pattern. In addition, when the dissolution contrast is small, there is a fear that a pattern cannot be formed on a substrate accurately according to a mask used in transferring and forming a pattern. Accordingly, the resist composition requires the highest dissolution contrast as possible in the use of an alkaline developer, that is, it is required to enhance resolution.

Moreover, in the chemically amplified negative resist composition that is capable of forming a fine pattern to be used for processing a rewire and is useful for the top coat to protect electric and electronic parts, sufficient solubility of the unexposed part in the aqueous alkaline developer is important. In other words, if solubility of the unexposed part in the aqueous alkaline developer is poor, and in the case that the resist composition film to cover the substrate is thick, sometimes observed are the pattern deteriorations such as an undissolved residue or a scum in the pattern bottom, and a footing profile in the pattern on the substrate. The scum and footing profile as mentioned above may cause problems including disconnection of an electric circuit and wire during a rewiring process; and thus, it is necessary to suppress generation of such problems.

Accordingly, drastic improvement of adhesiveness on a substrate is desired while not only maintaining the fine patterning ability in the rewiring technology required in accordance with the trends to higher density and higher integration of chips but also serving as a chemically amplified negative resist composition useful for a top coat to protect electric and electronic parts. In addition, wanted is prompt building up of the system in which patterning is possible by a widely used alkaline developer such as a 2.38% TMAH aqueous solution, further improvement in resolution can be expected, and a scum and a footing profile are not generated in the pattern bottom.

PRIOR ART DOCUMENTS

Patent Documents

Patent Document 1: Japanese Patent Laid-Open Publication No. 2008-184571
Patent Document 2: Japanese Patent Laid-Open Publication No. 2009-200315

SUMMARY OF THE INVENTION

The present invention was accomplished in view of the above-described problems, and an object thereof is to provide a silicone skeleton-containing polymer compound suitably used as a base resin of a chemically amplified negative resist composition that can remedy the problem of delamination generated on a metal wiring such as Cu and Al, an electrode, and a substrate, especially on a substrate such as SiN, and can form a fine pattern without generating a scum and a footing profile in the pattern bottom and on the substrate when the widely used 2.38% TMAH aqueous solution is used as a developer, and to further provide a method for producing the same and a chemically amplified negative resist composition using the silicone skeleton-containing polymer compound.

Another object of the present invention is to provide a patterning process in which the above-mentioned chemically amplified negative resist composition is easily applied on a substrate by using a spin coating method to form a fine pattern.

Further object of the present invention is to provide a photo-curable dry film using the chemically amplified negative resist composition, a method for producing the photo-curable dry film, a layered product having the photo-curable dry film laminated on a substrate, and a patterning process in which a resist layer having a wide range of film thickness is formed by using the photo-curable dry film to form a fine pattern even on a substrate having concavity and convexity.

Furthermore, the present invention has another object to provide a substrate protected by a cured film that is obtained by post-curing a pattern obtained by the above-mentioned patterning process at low temperature.

To accomplish the above-mentioned objects, the present invention provides a silicone skeleton-containing polymer compound comprising a repeating unit shown by the general formula (1) and having a weight average molecular weight of 3,000 to 500,000,

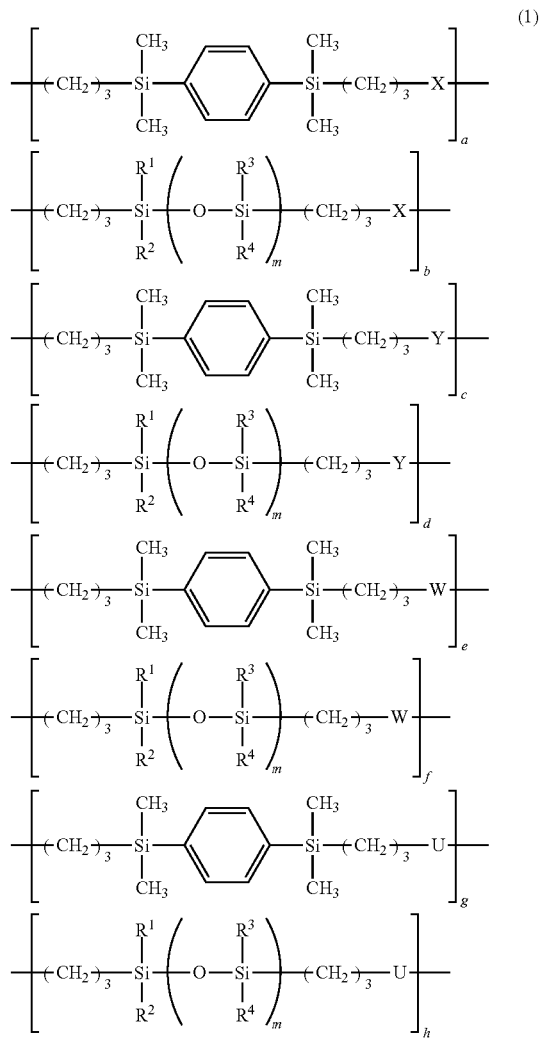

wherein $R^1$ to $R^4$ may be the same or different and represent a monovalent hydrocarbon group having 1 to 8 carbon atoms; "m" is an integer of 1 to 100; "a", "b", "c", "d", "e", and "f" are each 0 or a positive number, and "g" and "h" are each a positive number, provided that a+b+c+d+e+f+g+h=1; X is a divalent organic group shown by the general formula (2); Y is a divalent organic group shown by the general formula (3); W is a divalent organic group shown by the general formula (4); and U is a divalent organic group shown by the general formula (5),

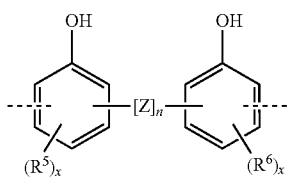
(2)

wherein Z represents a divalent organic group selected from any of

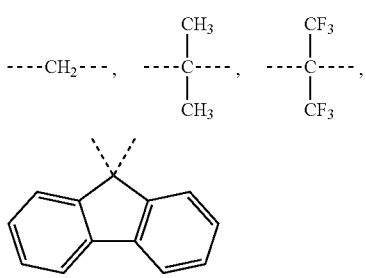

the dotted line represents a bond; "n" is 0 or 1; $R^5$ and $R^6$ each represent an alkyl group or alkoxy group having 1 to 4 carbon atoms and may be the same or different; and "x" is 0, 1, or 2;

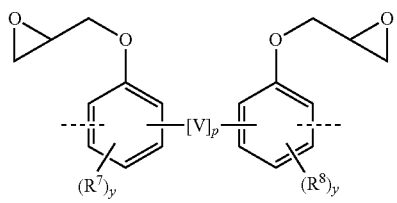
(3)

wherein V represents a divalent organic group selected from any of

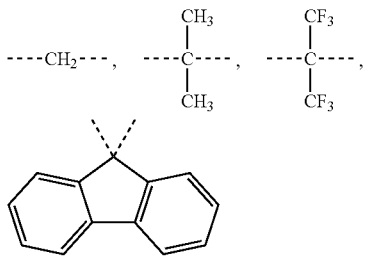

the dotted line represents a bond; "p" is 0 or 1; $R^7$ and $R^8$ each represent an alkyl group or alkoxy group having 1 to 4 carbon atoms and may be the same or different; and "y" is 0, 1, or 2;

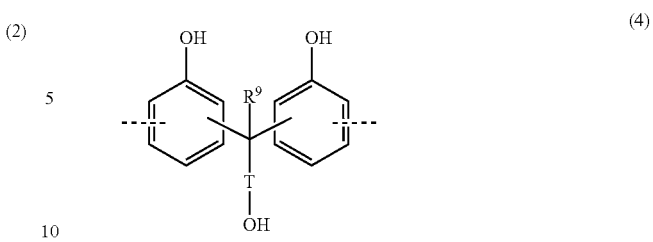
(4)

wherein the dotted line represents a bond; T represents an alkylene group having 1 to 10 carbon atoms or a divalent aromatic group; and $R^9$ represents a hydrogen atom or a methyl group;

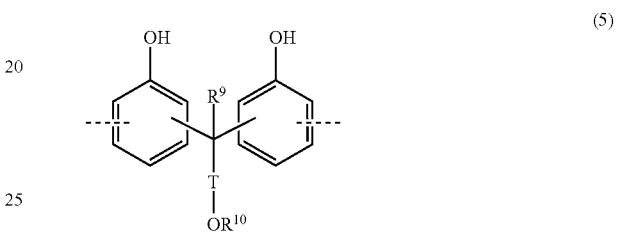
(5)

wherein the dotted line represents a bond; T and $R^9$ have the same meanings as defined above; and $R^{10}$ represents a monovalent carboxyl-containing organic group.

Such a silicone skeleton-containing polymer compound can be used as a base resin of a chemically amplified negative resist composition that can remedy the problem of delamination generated on a metal wiring such as Cu and Al, an electrode, and a substrate, especially on a substrate such as SiN, and can form a fine pattern without generating a scum and a footing profile in the pattern bottom and on the substrate when the widely used 2.38% TMAH aqueous solution is used as a developer.

$R^{10}$ in the general formula (5) is preferably a monovalent carboxyl-containing organic group shown by the general formula (6),

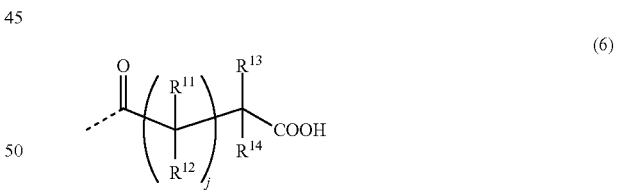
(6)

wherein the dotted line represents a bond; $R^{11}$ to $R^{14}$ may be the same or different and represent a hydrogen atom, a halogen atom, a linear, branched, or cyclic alkyl group having 1 to 12 carbon atoms, or an aromatic group; $R^{11}$ and $R^{13}$ may be bonded respectively to $R^{12}$ and $R^{14}$ to form a substituted or unsubstituted ring structure having 1 to 12 carbon atoms; and "j" is any of 1 to 7.

The silicone skeleton-containing polymer compound like this can further enhance the effects of the present invention.

In the general formula (1), it is preferred that $0 \leq a \leq 0.5$, $0 \leq b \leq 0.3$, $0 \leq c \leq 0.5$, $0 \leq d \leq 0.3$, $0 \leq e \leq 0.8$, $0 \leq f \leq 0.5$, $0 < g \leq 0.8$, and $0 < h \leq 0.5$.

The silicone skeleton-containing polymer compound like this can further enhance the effects of the present invention.

Further, in the general formula (1), it is preferred that a=0, b=0, c=0, d=0, 0≤e≤0.3, 0≤f≤0.2, 0<g≤0.8, and 0<h≤0.5.

The silicone skeleton-containing polymer compound like this can further enhance the effects of the present invention.

In addition, the present invention provides a method for producing the above-mentioned silicone skeleton-containing polymer compound, comprising:
introducing a carboxyl group by reacting a part or all of alcoholic or phenolic hydroxyl groups of a silicone skeleton-containing polymer compound having a repeating unit shown by the general formula (7) with a dicarboxylic acid anhydride,

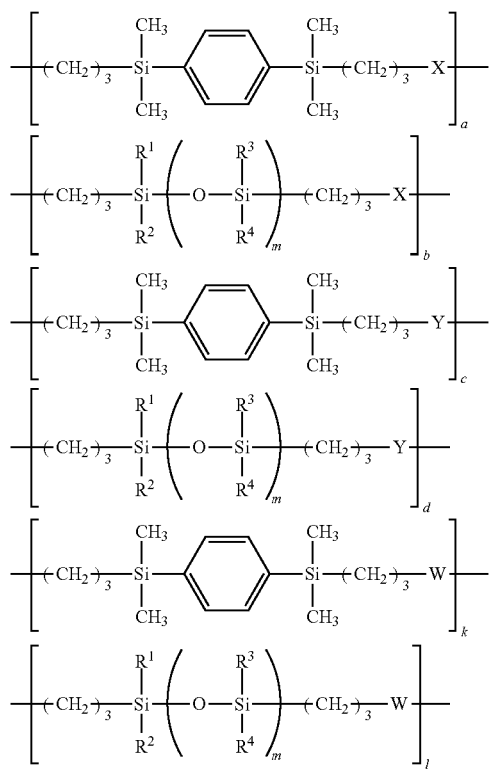
(7)

wherein $R^1$ to $R^4$, "a", "b", "c", "d", "m", X, Y, and W have the same meanings as defined above; "k" and "l" are each a positive number satisfying k=e+g and l=f+h; and "e", "f", "g", and "h" have the same meanings as defined above.

The producing method like this is suitable to obtain the above-mentioned silicone skeleton-containing polymer compound.

The silicone skeleton-containing polymer compound shown by the general formula (7) is preferably a polymer compound obtained by polymerization reaction of: either or both of a hydrogensilphenylene shown by the structural formula (8) and a dihydroorganosiloxane shown by the general formula (9),

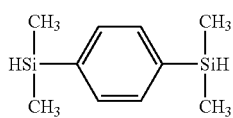
(8)

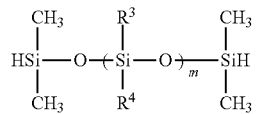
(9)

wherein $R^3$, $R^4$, and "m" have the same meanings as defined above;

either or both of a phenol compound having two allyl groups and shown by the general formula (10) and a compound having two allyl groups and shown by the general formula (11),

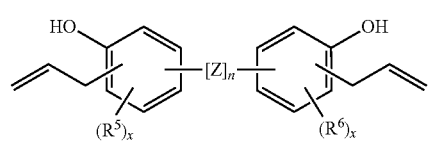
(10)

wherein Z, $R^5$, $R^6$, "n" and "x" have the same meanings as defined above,

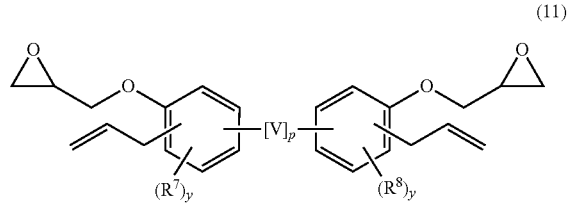
(11)

wherein V, $R^7$, $R^8$, "p" and "y" have the same meanings as defined above;

and a phenol compound having two allyl groups and shown by the general formula (12)

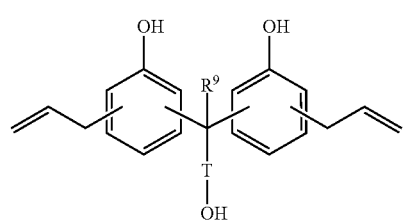
(12)

wherein T and $R^9$ have the same meanings as defined above; in the presence of a catalyst.

The producing method like this is more suitable to obtain the above-mentioned silicone skeleton-containing polymer compound.

The phenol compound having two allyl groups and shown by the general formula (12) is preferably a compound shown by the general formula (13),

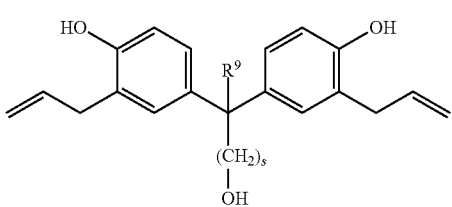
(13)

wherein $R^9$ has the same meaning as defined above, and "s" is a positive number of 1 to 12.

Such a compound is suitable to obtain the silicone skeleton-containing polymer compound having an alcoholic hydroxyl group as mentioned above.

Alternatively, the phenol compound having two allyl groups and shown by the general formula (12) is preferably a compound shown by the general formula (14),

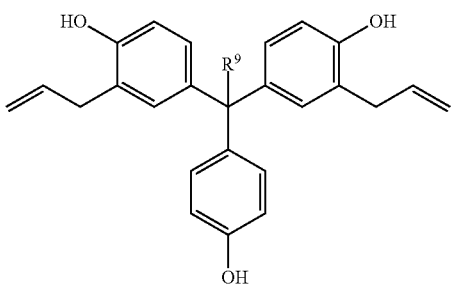
(14)

wherein $R^9$ has the same meaning as defined above.

Such a compound is suitable to obtain the silicone skeleton-containing polymer compound having a phenolic hydroxyl group as mentioned above.

In addition, the present invention provides a silicone skeleton-containing polymer compound comprising a repeating unit shown by the general formula (24) and having a weight average molecular weight of 3,000 to 500,000,

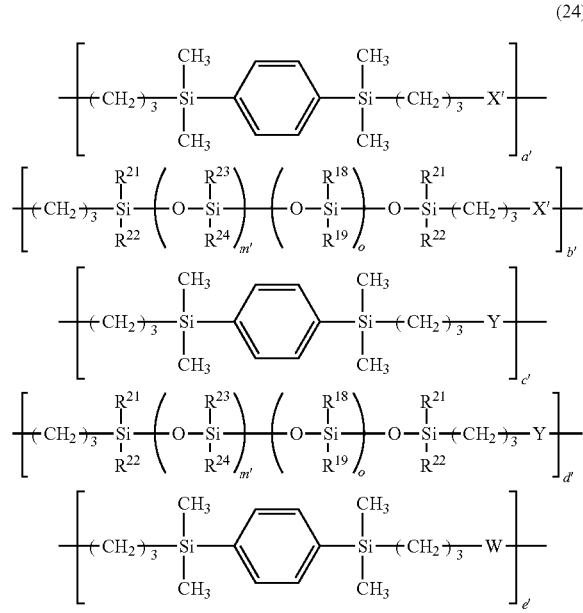
(24)

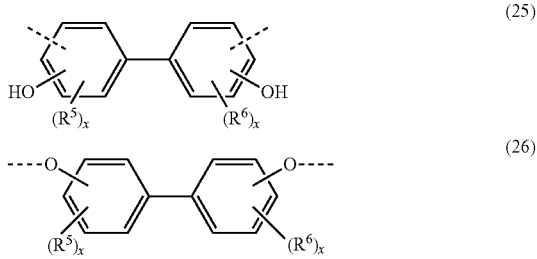

wherein $R^{21}$ to $R^{24}$ may be the same or different and represent a monovalent organic group having 1 to 15 carbon atoms and optionally containing an oxygen atom; $R^{18}$ and $R^{19}$ may be the same or different and represent a monovalent organic group having 1 to 28 carbon atoms and optionally containing an oxygen atom; m' is an integer of 0 to 100; "o" is an integer of 0 to 100; c', d', e', and f' are each 0 or a positive number, and a', b', g' and h' are each a positive number, provided that a'+b'+c'+d'+e'+f'+g'+h'=1; X' is a divalent organic group shown by the general formula (25) or the general formula (26); Y is a divalent organic group shown by the general formula (3); W is a divalent organic group shown by the general formula (4); and U is a divalent organic group shown by the general formula (5),

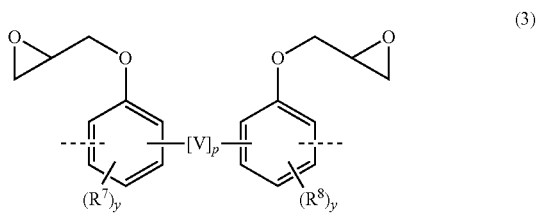
(25)

(26)

wherein the dotted line represents a bond; $R^5$ and $R^6$ each represent an alkyl group or alkoxy group having 1 to 4 carbon atoms and may be the same or different; and "x" is 0, 1, or 2;

(3)

wherein V represents a divalent organic group selected from any of

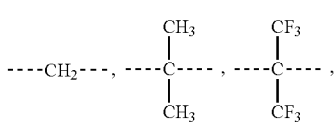

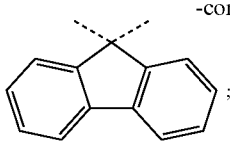

the dotted line represents a bond; "p" is 0 or 1; $R^7$ and $R^8$ each represent an alkyl group or alkoxy group having 1 to 4 carbon atoms and may be the same or different; and "y" is 0, 1, or 2;

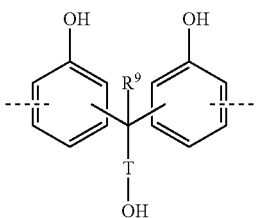

(4)

wherein the dotted line represents a bond; T represents an alkylene group having 1 to 10 carbon atoms or a divalent aromatic group; and $R^9$ represents a hydrogen atom or a methyl group;

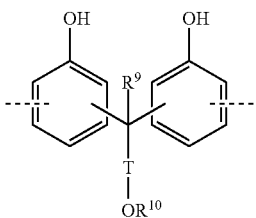

(5)

wherein the dotted line represents a bond; T and $R^9$ have the same meanings as defined above; and $R^{10}$ represents a monovalent carboxyl-containing organic group.

Such a silicone skeleton-containing polymer compound can be used as a base resin of a chemically amplified negative resist composition that can remedy the problem of delamination generated on a metal wiring such as Cu and Al, an electrode, and a substrate, especially on a substrate such as SiN, can form a fine pattern without generating a scum and a footing profile in the pattern bottom and on the substrate when the widely used 2.38% TMAH aqueous solution is used as a developer, and can provide a cured film excellent in mechanical strength, chemical resistance, and reliability, etc.

It is preferred that in the general formula (24), "o" is an integer of 1 to 100; $R^{21}$ to $R^{24}$ may be the same or different and represent a monovalent hydrocarbon group having 1 to 8 carbon atoms; $R^{18}$ represents a phenyl substituent containing a hydroxyl group or an alkoxy group and shown by the general formula (27); and $R^{19}$ may be the same as or different from $R^{21}$ to $R^{24}$ and represents a monovalent organic group having 1 to 10 carbon atoms and optionally containing an oxygen atom, or $R^{19}$ may be the same as or different from $R^{18}$ and represents a phenyl substituent containing a hydroxyl group or an alkoxy group and shown by the general formula (27),

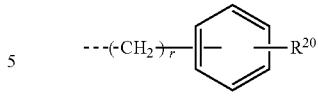

(27)

wherein "r" is an integer of 0 to 10; $R^{20}$ represents a hydroxyl group or a linear, branched, or cyclic alkoxy group having 1 to 12 carbon atoms.

A chemically amplified negative resist composition using such a silicone skeleton-containing polymer compound can improve the crosslinking reactivity of the exposed part in patterning. Moreover, the improvement in crosslinking reactivity of the exposed part leads to low solubility of the exposed part in the developer and thus high dissolution contrast.

In this case, the phenyl substituent shown by the general formula (27) is preferably one group, or two or more groups selected from the formula (28),

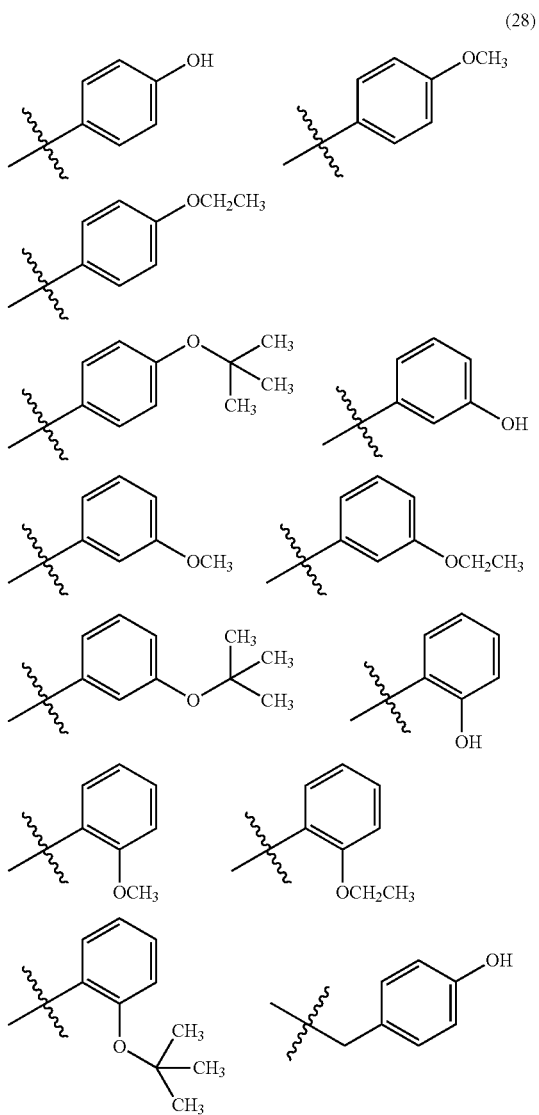

(28)

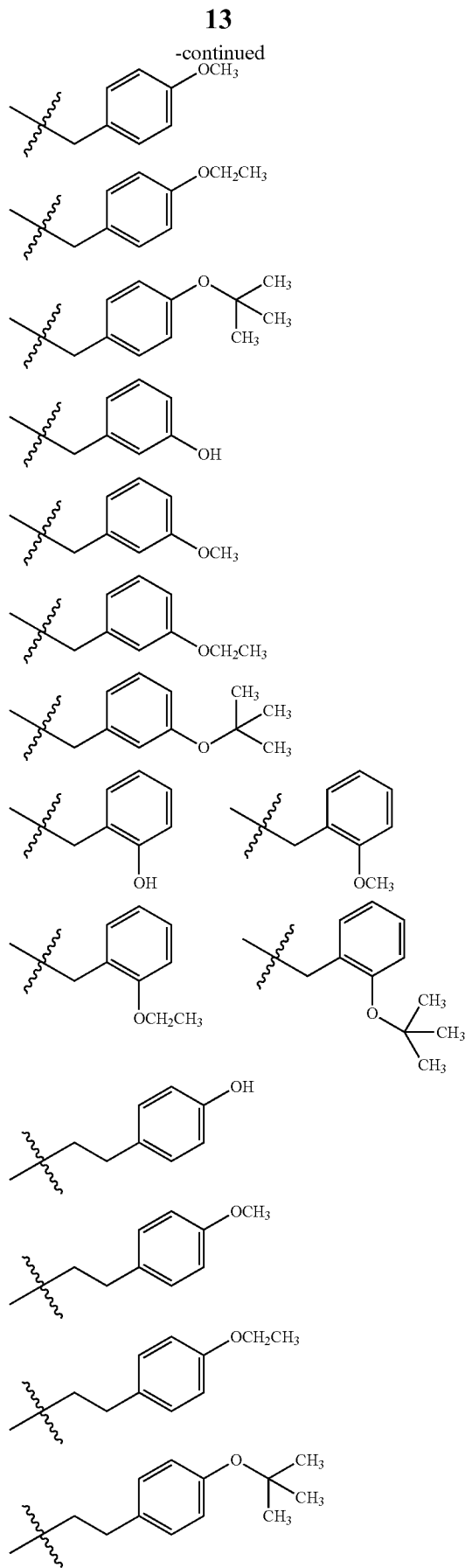
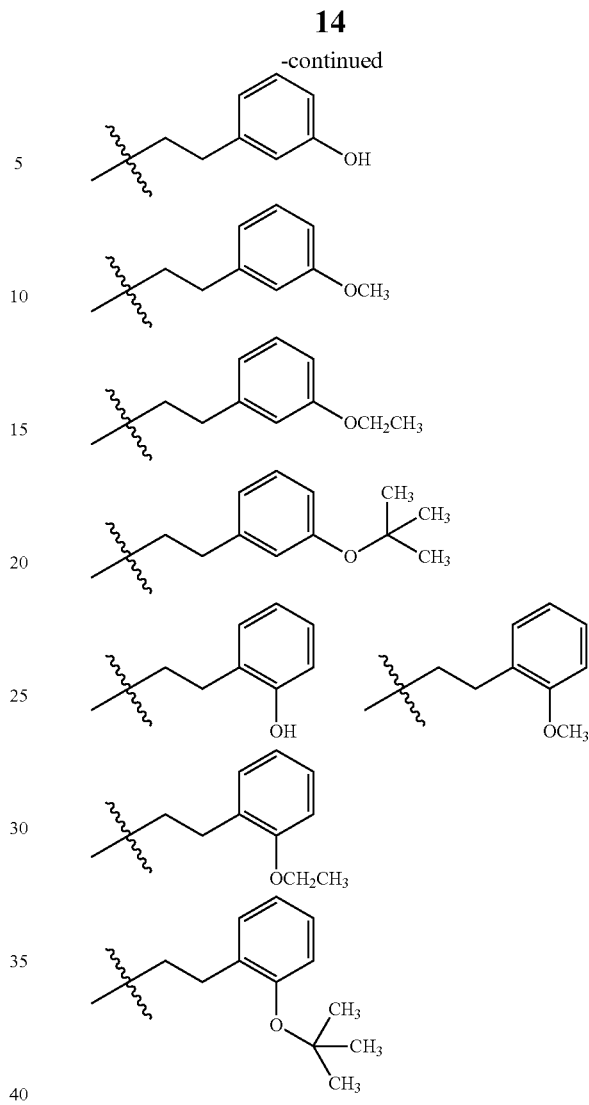

wherein the line with a wavy line represents a bonding arm.

A chemically amplified negative resist composition using such a silicone skeleton-containing polymer compound can further improve the crosslinking reactivity of the exposed part in patterning. Moreover, the further improvement in crosslinking reactivity of the exposed part leads to lower solubility of the exposed part in the developer and thus higher dissolution contrast.

In addition, the present invention provides a chemically amplified negative resist composition comprising:

(A) the above-mentioned silicone skeleton-containing polymer compound;
(B) a photosensitive acid generator capable of generating an acid by decomposition with light having a wavelength of 190 to 500 nm;
(C) one or more crosslinking agents selected from an amino condensate modified by formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted by a glycidyl group, a polyhydric phenol compound in which a hydrogen atom of a phenolic hydroxyl group is substituted by a substituent shown by the formula (C-1), and a compound having two or more nitrogen atoms bonded to a glycidyl group and shown by the formula (C-2),

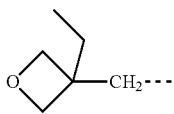

(C-1)

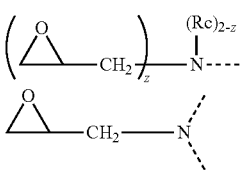

(C-2)

wherein the dotted line represents a bond; $R_c$ represents a linear, branched, or cyclic alkyl group having 1 to 6 carbon atoms; and "z" is 1 or 2;

(D) a solvent; and (E) a basic compound.

Such a chemically amplified negative resist composition can remedy the problem of delamination generated on a metal wiring such as Cu and Al, an electrode, and a substrate, especially on a substrate such as SiN, and can form a fine pattern without generating a scum and a footing profile in the pattern bottom and on the substrate when the widely used 2.38% TMAH aqueous solution is used as a developer.

In addition, the present invention provides a photo-curable dry film comprising a supporting film, a top coat film, and a photo-curable resin layer having a film thickness of 10 to 100 μm, the photo-curable resin layer being sandwiched between the supporting film and the top coat film, wherein the photo-curable resin layer is formed of the above-mentioned chemically amplified negative resist composition.

Such a photo-curable dry film can form a fine pattern in wide ranges of film thickness and wavelength, and exhibits excellent flexibility, heat resistance, electric characteristics, adhesiveness, reliability, and chemical resistance by post-curing at low temperature.

In addition, the present invention provides a method for producing a photo-curable dry film, comprising:

(I) continuously applying the above-mentioned chemically amplified negative resist composition onto a supporting film to form a photo-curable resin layer, (II) continuously drying the photo-curable resin layer, and further (III) laminating a top coat film onto the photo-curable resin layer.

The producing method like this is suitable to obtain the above-mentioned photo-curable dry film.

In addition, the present invention provides a patterning process comprising:

(1) applying the above-mentioned chemically amplified negative resist composition onto a substrate to form a photosensitive material film;

(2) exposing the photosensitive material film to a high energy beam having a wavelength of 190 to 500 nm or an electron beam via a photomask after a heat treatment; and (3) subjecting to development with a developer after a heat treatment.

Such a patterning process can remedy the problem of delamination generated on a metal wiring such as Cu and Al, an electrode, and a substrate, especially on a substrate such as SiN, and can form a fine pattern without generating a scum and a footing profile in the pattern bottom and on the substrate when the widely used 2.38% TMAH aqueous solution is used as a developer. Also, applying the chemically amplified negative resist composition can be performed by a spin coating method.

Further, the present invention provides a patterning process comprising:

(i) separating the top coat film from the above-mentioned photo-curable dry film and bringing an exposed photo-curable resin layer into close contact with a substrate;

(ii) exposing the photo-curable resin layer to a high energy beam having a wavelength of 190 to 500 nm or an electron beam via a photomask either through the supporting film or in a peeled-off state of the supporting film;

(iii) subjecting to a heat treatment after the exposure; and (iv) subjecting to development with a developer.

Such a patterning process can remedy the problem of delamination generated on a metal wiring such as Cu and Al, an electrode, and a substrate, especially on a substrate such as SiN, and can form a fine pattern without generating a scum and a footing profile in the pattern bottom and on the substrate when the widely used 2.38% TMAH aqueous solution is used as a developer.

At this time, it is preferred that the patterning process further comprise post-curing a patterned film formed by the development at 100 to 250° C. after the development.

The cured film thus obtained has excellent flexibility, adhesiveness to substrate, heat resistance, electric characteristics, mechanical strength, and chemical resistance to a soldering flux liquid, and thus, a semiconductor device having the cured film like this as the top coat exhibits a superior reliability, and especially, generation of cracks during a thermal cycle test can be prevented.

At this time, the substrate may include a trench and/or a hole each having an aperture width of 10 to 100 μm and a depth of 10 to 120 μm.

When the photo-curable dry film of the present invention is used, a resist film having a wide range of film thickness can be formed even on the substrate having concavity and convexity, so that a fine pattern can be formed.

Also, the present invention provides a layered product comprising a substrate including a trench and/or a hole each having an aperture width of 10 to 100 μm and a depth of 10 to 120 μm, and the above-mentioned photo-curable resin layer of the photo-curable dry film laminated on the substrate.

When such a layered product is employed, the pattern can be adequately embedded therein. Further, the layered product is excellent in various properties.

Also, the present invention provides a substrate that is protected by a film obtained by curing a pattern formed by the above-mentioned patterning process.

Such a substrate is protected by the cured film having excellent flexibility, adhesiveness, heat resistance, electric characteristics, mechanical strength, chemical resistance, reliability, and crack resistance.

As mentioned above, the present invention can provide a silicone skeleton-containing polymer compound suitably used as a base resin of a chemically amplified negative resist composition that can dramatically remedy the problem of delamination generated on a metal wiring such as Cu and Al, an electrode, and a substrate, especially on a substrate such as SiN, and further provide a method for producing the same and a chemically amplified negative resist composition using the silicone skeleton-containing polymer compound. By using this chemically amplified negative resist composition, a fine pattern can be formed without generating a scum and a footing profile in a wide range of wavelength; and in addition, miniaturization of the pattern is possible in the rewiring technology in accordance with the trend to higher density and higher integration of chips. Moreover, this chemically amplified negative resist composition can be developed by an aqueous alkaline solution such as a 2.38% TMAH aqueous solution, thereby providing a photo-curable dry film and a patterning process using the same. When the pattern formed by the patterning process like this is post-cured at low temperature, a substrate protected by a cured film having excellent flexibility, adhesiveness, heat resistance, electric characteristics, mechanical strength, chemical resistance, reliability, and crack resistance can be obtained.

BRIEF DESCRIPTION OF THE DRAWING

FIG. 1 is an explanatory view of the adhesiveness measurement method in Examples.

DETAILED DESCRIPTION OF THE PREFERRED EMBODIMENTS

As described above, there have been demanded a silicone skeleton-containing polymer compound suitably used as a base resin of a chemically amplified negative resist composition that can remedy the problem of delamination generated on a metal wiring such as Cu and Al, an electrode, and a substrate, especially on a substrate such as SiN, can form a fine pattern without generating a scum and a footing profile in the pattern bottom and on the substrate when the widely used 2.38% TMAH aqueous solution is used as a developer, and can provide a cured film excellent in mechanical strength, chemical resistance, and reliability, etc.

The present inventors have earnestly investigated to achieve the above object, and consequently found that a silicone skeleton-containing polymer compound containing alcoholic or phenolic hydroxyl groups is obtained by polymerization reaction of a phenol compound having two allyl groups of formula (12), a hydrogensilphenylene of formula (8), a dihydroorganosiloxane of formula (9), a phenol compound having two allyl groups of formula (10), and a compound having two allyl groups of formula (11) in the presence of a catalyst, and a carboxyl group can be introduced to the silicone skeleton by reacting a part or all of the alcoholic or phenolic hydroxyl groups of the obtained silicone skeleton-containing polymer compound with a dicarboxylic acid anhydride, whereby a desired silicone skeleton-containing polymer compound having carboxylic acid and siloxane chain can be obtained. Also, the present inventors found that a chemically amplified negative resist composition comprising the following components (A) to (E), which uses the above-mentioned silicone skeleton-containing polymer compound having carboxylic acid and siloxane chain, can form a fine pattern, dramatically remedy the problem of delamination generated on a metal wiring such as Cu and Al, an electrode, and a substrate, especially on a substrate such as SiN, and dramatically improve the adhesiveness to substrate. Further, they found that a cured film obtained by the above-mentioned patterning process is excellent as a top coat to protect electric and electronic parts, thereby bringing the present invention to completion.

Hereinafter, the present invention will be described in detail, but the present invention is not limited thereto.

The silicone skeleton-containing polymer compound of the present invention contains a repeating unit shown by the general formula (1) and has a weight average molecular weight of 3,000 to 500,000,

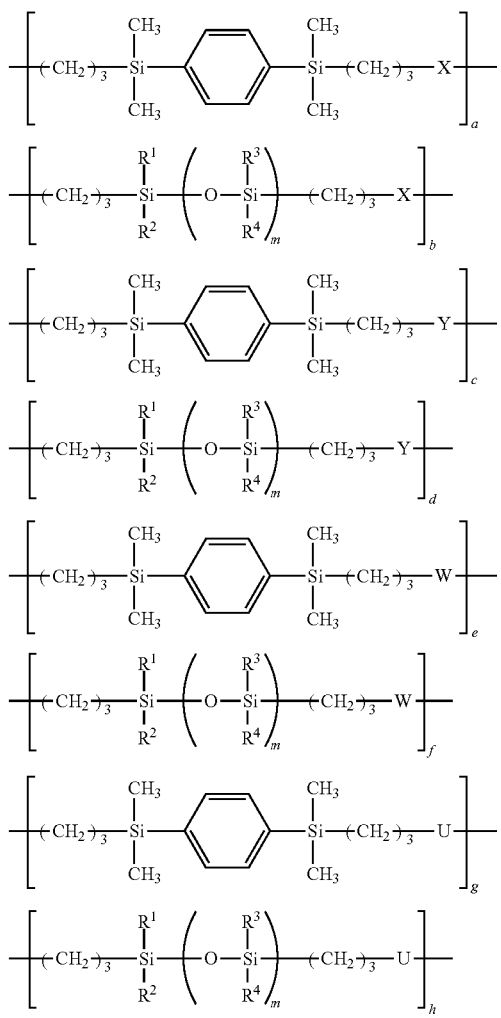

wherein $R^1$ to $R^4$ may be the same or different and represent a monovalent hydrocarbon group having 1 to 8 carbon atoms; "m" is an integer of 1 to 100; "a", "b", "c", "d", "e", and "f" are each 0 or a positive number, and "g" and "h" are each a positive number, provided that a+b+c+d+e+f+g+h=1; X is a divalent organic group shown by the general formula (2); Y is a divalent organic group shown by the general formula (3); W is a divalent organic group shown by the general formula (4); and U is a divalent organic group shown by the general formula (5),

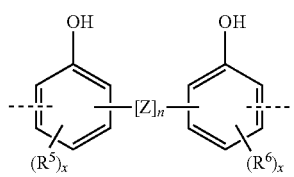

wherein Z represents a divalent organic group selected from any of

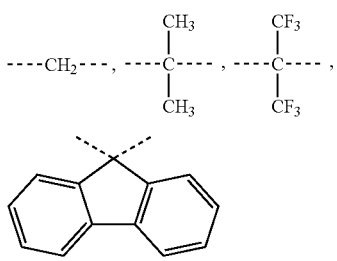

the dotted line represents a bond; "n" is 0 or 1; $R^5$ and $R^6$ each represent an alkyl group or alkoxy group having 1 to 4 carbon atoms and may be the same or different; and "x" is 0, 1, or 2;

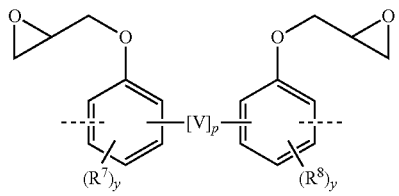
(3)

wherein V represents a divalent organic group selected from any of

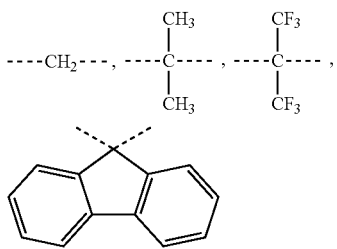

the dotted line represents a bond; "p" is 0 or 1; $R^7$ and $R^8$ each represent an alkyl group or alkoxy group having 1 to 4 carbon atoms and may be the same or different; and "y" is 0, 1, or 2;

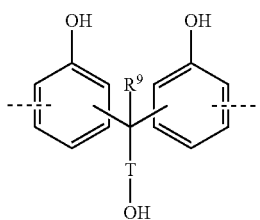
(4)

wherein the dotted line represents a bond; T represents an alkylene group having 1 to 10 carbon atoms or a divalent aromatic group; and $R^9$ represents a hydrogen atom or a methyl group;

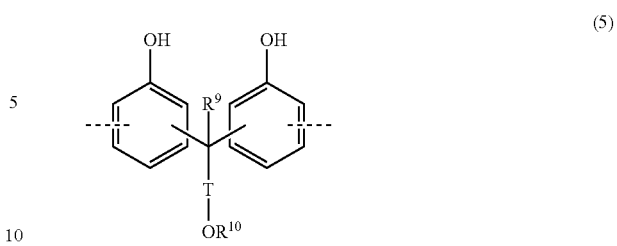
(5)

wherein the dotted line represents a bond; T and $R^9$ have the same meanings as defined above; and $R^{10}$ represents a monovalent carboxyl-containing organic group.

In the general formula (1), $R^1$ to $R^4$ may be the same or different and represent a monovalent hydrocarbon group having 1 to 8 carbon atoms, preferably having 1 to 6 carbon atoms. Illustrative examples thereof include linear, branched or cyclic alkyl groups such as a methyl group, an ethyl group, a propyl group, an isopropyl group, a n-butyl group, a tert-butyl group, and a cyclohexyl group; linear, branched or cyclic alkenyl groups such as a vinyl group, an allyl group, a propenyl group, a butenyl group, a hexenyl group, and a cyclohexenyl group; aryl groups such as a phenyl group and a tolyl group; and aralkyl groups such as a benzyl group and a phenethyl group.

In view of the compatibility with a later-described cross-linking agent and photosensitive acid generator, and in view of photo-curability, "m" is an integer of 1 to 100, preferably 1 to 80. Also, in view of adhesiveness to substrate, electric characteristics, and reliability, "a", "b", "c", "d", "e", and "f" are each 0 or a positive number, and "g" and "h" are each a positive number, provided that a+b+c+d+e+f+g+h=1. In this case, it is preferred that $0 \le a \le 0.5$, $0 \le b \le 0.3$, $0 \le c \le 0.5$, $0 \le d \le 0.3$, $0 \le e \le 0.8$, $0 \le f \le 0.5$, $0 < g \le 0.8$, and $0 < h \le 0.5$.

With respect to "a", "b", "c", "d", "e", "f", "g", and "h", it is more preferred that i) $0 \le a \le 0.5$, $0 \le b \le 0.3$, $0 \le c \le 0.5$, $0 \le d \le 0.3$, $0 \le e \le 0.8$, $0 \le f \le 0.5$, $0 < g \le 0.8$, and $0 < h \le 0.5$;

ii) $0 \le a \le 0.5$, $0 \le b \le 0.3$, c=0, d=0, $0 \le e \le 0.8$, $0 \le f \le 0.5$, $0 < g \le 0.8$, and $0 < h \le 0.5$;

iii) a=0, b=0, $0 \le c \le 0.5$, $0 \le d \le 0.3$, $0 \le e \le 0.8$, $0 \le f \le 0.5$, $0 < g \le 0.8$, and $0 < h \le 0.5$;

iv) a=0, b=0, c=0, d=0, $0 \le e \le 0.3$, $0 \le f \le 0.2$, $0 < g \le 0.8$, and $0 < h \le 0.5$; or v) a=0, b=0, c=0, d=0, e=0, f=0, $0 < g \le 0.8$, and $0 < h \le 0.5$.

Here, the range of "e" is preferably $0 \le e \le 0.8$, more preferably $0 \le e \le 0.6$, much more preferably $0 \le e \le 0.3$.

The range of "f" is preferably $0 < f \le 0.5$, more preferably $0 < f \le 0.3$. If "f" is 0.5 or less, it is possible to prevent the polymer compound becoming difficult to dissolve in alkaline developer in the patterning using an aqueous alkaline solution as a developer, which is object of the present invention. Also, if "f" is 0.5 or less, there is no fear that the film to be formed exhibits extremely high adhesiveness, so that its processability is deteriorated; and there is no fear that when the inventive photo-curable dry film having a structure sandwiched between a supporting film and a top coat film is produced, the top coat film cannot be detached, and therefore it cannot be used as the photo-curable dry film.

The range of "g" is preferably $0 < g \le 0.8$, more preferably $0.2 \le g \le 0.8$. If "g" is 0.2 or more, the solubility in aqueous alkaline developer is not lowered, so that a good pattern can be formed. That is, if "g" is 0.2 or more and thus the solubility of the unexposed part in aqueous alkaline developer is excellent in the negative pattern formation, the pattern deterioration such as an undissolved residue and a scum in the pattern bottom, and a footing profile in the pattern on the substrate can be suppressed even when the resist composition film to cover the substrate is thick. On the other hand, if "g" is 0.8 or less, the solubility in aqueous alkaline developer is appropriate; and thus, it is possible to prevent the problem that the crosslinking reaction to obtain a negative pattern does not proceed to the insoluble stage, and therefore a pattern cannot be obtained.

The range of "h" is preferably $0<h\leq 0.5$, more preferably $0<h\leq 0.3$.

In the general formula (1), X is a divalent organic group shown by the general formula (2), Y is a divalent organic group shown by the general formula (3), W is a divalent organic group shown by the general formula (4), and U is a divalent organic group shown by the general formula (5),

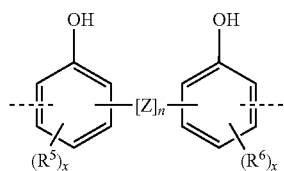
(2)

wherein Z represents a divalent organic group selected from any of

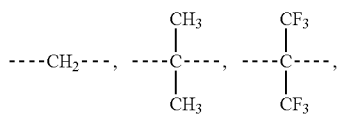

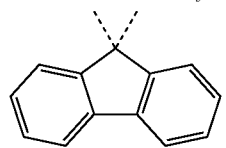

the dotted line represents a bond; "n" is 0 or 1; $R^5$ and $R^6$ each represent an alkyl group or alkoxy group having 1 to 4 carbon atoms and may be the same or different; and "x" is 0, 1, or 2;

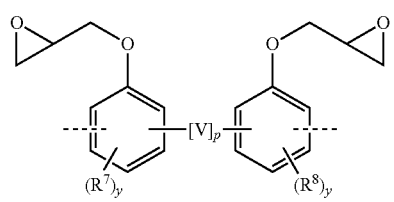
(3)

wherein V represents a divalent organic group selected from any of

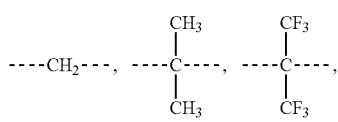

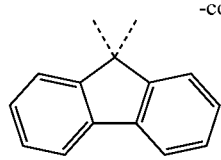

the dotted line represents a bond; "p" is 0 or 1; $R^7$ and $R^8$ each represent an alkyl group or alkoxy group having 1 to 4 carbon atoms and may be the same or different; and "y" is 0, 1, or 2;

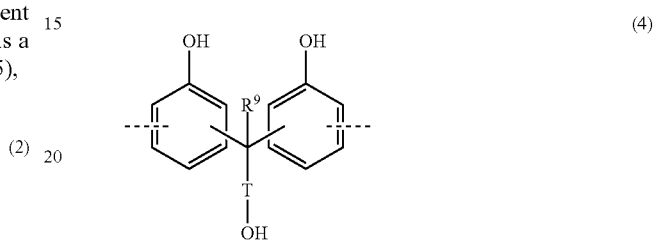
(4)

wherein the dotted line represents a bond; T represents an alkylene group having 1 to 10 carbon atoms or a divalent aromatic group; and $R^9$ represents a hydrogen atom or a methyl group;

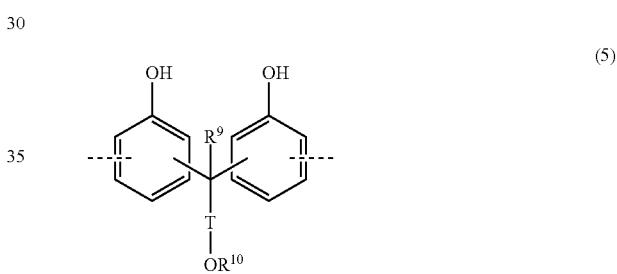
(5)

wherein the dotted line represents a bond; T and $R^9$ have the same meanings as defined above; and $R^{10}$ represents a monovalent carboxyl-containing organic group.

$R^{10}$ in the general formula (5) may be a monovalent carboxyl-containing organic group shown by the general formula (6),

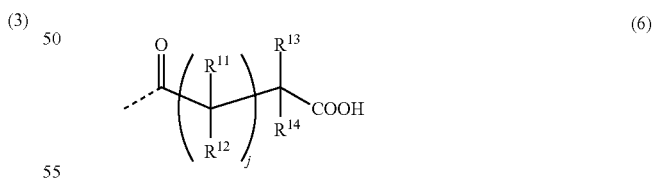
(6)

wherein the dotted line represents a bond; $R^{11}$ to $R^{14}$ may be the same or different and represent a hydrogen atom, a halogen atom, a linear, branched, or cyclic alkyl group having 1 to 12 carbon atoms, or an aromatic group; $R^{11}$ and $R^{13}$ may be bonded respectively to $R^{12}$ and $R^{14}$ to form a substituted or unsubstituted ring structure having 1 to 12 carbon atoms; and "j" is any of 1 to 7.

The silicone skeleton-containing polymer compound of the present invention should have a weight average molecular weight of 3,000 to 500,000, preferably 5,000 to 300,000, in view of the compatibility and the photo-curability of a later-described chemically amplified negative resist composition using it, and in view of mechanical characteristics of a cured product obtained from the chemically amplified negative resist composition. Herein, the weight average molecular weight is determined by gel permeation chromatography (GPC) in terms of polystyrene.

Also, the present invention provides a method for producing the silicone skeleton-containing polymer compound of the present invention.

The method for producing the silicone skeleton-containing polymer compound of the present invention includes introducing a carboxyl group by reacting a part or all of alcoholic or phenolic hydroxyl groups of a silicone skeleton-containing polymer compound having a repeating unit shown by the general formula (7) with a dicarboxylic acid anhydride.

In the method for producing the silicone skeleton-containing polymer compound of the present invention, the silicone skeleton-containing polymer compound having a repeating unit shown by the general formula (7) may be used as an intermediate raw material,

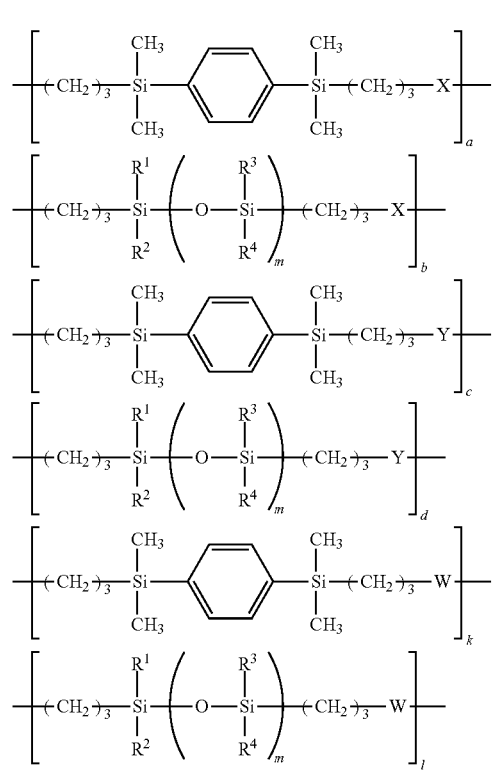

wherein $R^1$ to $R^4$, "a", "b", "c", "d", "m", X, Y, and W have the same meanings as defined above; "k" and "l" are each a positive number satisfying k=e+g and l=f+h; and "e", "f", "g", and "h" have the same meanings as defined above.

When the weight average molecular weight of the silicone skeleton-containing polymer compound having a repeating unit shown by the general formula (7) which is used as an intermediate raw material, is lowered, the average molecular weight of the objective silicone skeleton-containing polymer compound is also lowered, which results in low viscosity of the objective chemically amplified negative resist composition. Therefore, the viscosity of the resin layer formed from the chemically amplified negative resist composition using the above-mentioned silicone skeleton-containing polymer compound is also lowered. Moreover, in the molecule of the silicone skeleton-containing polymer compound, when the proportion of the molecular units containing linear polysiloxane (i.e. "b", "d", "f", and "h" in the general formula (1)) is increased, the proportion of the molecular units containing aromatic compound such as silphenylene (i.e. "a" "c" "e" and "g" in general formula (1)) is relatively decreased, which results in low viscosity of the above-mentioned silicone skeleton-containing polymer compound. Therefore, the viscosity of the resin layer formed from the chemically amplified negative resist composition using the above-mentioned silicone skeleton-containing polymer compound is also lowered. Furthermore, in the molecule of the silicone skeleton-containing polymer compound, when the chain length of the linear polysiloxane is increased, i.e., when the value of "m" in the general formula (1) is increased, the viscosity of the above-mentioned silicone skeleton-containing polymer compound is lowered. Therefore, the viscosity of the resin layer formed from the chemically amplified negative resist composition using the above-mentioned silicone skeleton-containing polymer compound is also lowered.

The silicone skeleton-containing polymer compound having a repeating unit shown by the general formula (7) can be obtained by so-called "hydrosilylation" polymerization reaction of:

either or both of a hydrogensilphenylene (1,4-bis(dimethylsilyl)benzene) shown by the structural formula (8) and a dihydroorganosiloxane shown by the general formula (9),

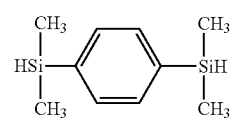

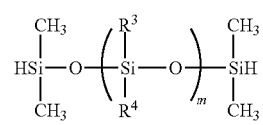

wherein $R^3$, $R^4$, and "m" have the same meanings as defined above;

either or both of a phenol compound having two allyl groups and shown by the general formula (10) and a compound having two allyl groups and shown by the general formula (11),

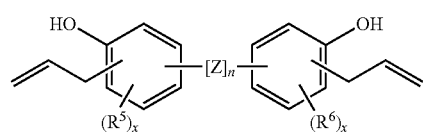

wherein Z, $R^5$, $R^6$, "n" and "x" have the same meanings as defined above,

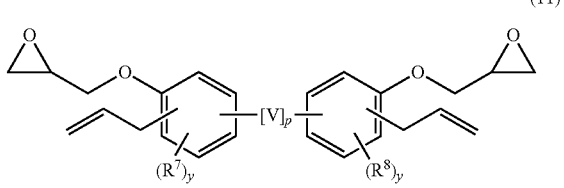

(11)

wherein V, $R^7$, $R^8$, "p" and "y" have the same meanings as defined above; and a phenol compound having two allyl groups and shown by the general formula (12),

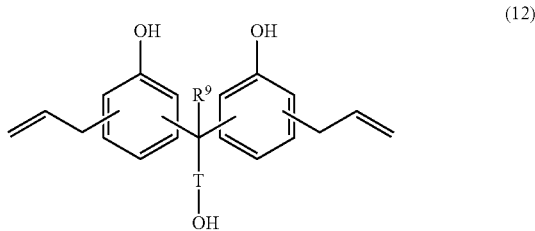

(12)

wherein T and $R^9$ have the same meanings as defined above; in the presence of a catalyst.

The phenol compound having two allyl groups and shown by the general formula (12) is preferably a compound shown by the general formula (13) or a compound shown by the general formula (14),

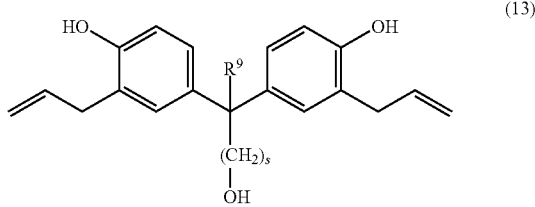

(13)

wherein $R^9$ has the same meaning as defined above, and "s" is a positive number of 1 to 12,

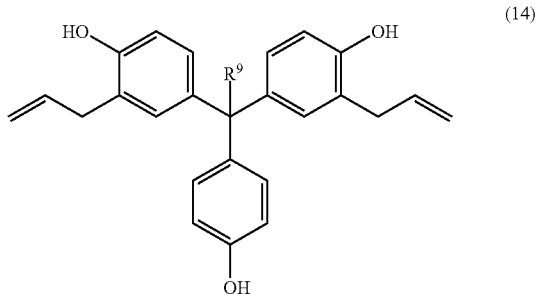

(14)

wherein $R^9$ has the same meaning as defined above.

First, explanation is given about preferable conditions of the "hydrosilylation" polymerization reaction in the presence of a catalyst between the hydrogensilphenylene shown by the structural formula (8) and/or the dihydroorganosiloxane shown by the general formula (9), the phenol compound having two allyl groups and shown by the general formula (10), the compound having two allyl groups and a glycidyl group and shown by the general formula (11), and a phenol compound having two allyl groups and shown by the general formula (12) (preferably, a compound having two allyl groups and an alcoholic hydroxyl group as shown by the general formula (13) or a phenol compound having two allyl groups as shown by the general formula (14)).

Then, explanation is given about preferable method for obtaining the phenol compound having two allyl groups and shown by the general formula (12), particularly, the compound having two allyl groups and an alcoholic hydroxyl group and shown by the general formula (13) or the phenol compound having two allyl groups and shown by the general formula (14).

Then, explanation is given about the reaction to introduce a carboxyl group by reacting a part or all of alcoholic or phenolic hydroxyl groups of the silicone skeleton-containing polymer compound prepared by the hydrosilyltion polymerization reaction with a dicarboxylic acid anhydride.

First, the preferable conditions of the "hydrosilylation" polymerization reaction in the presence of a catalyst will be described.

Here, the weight average molecular weight of the silicone skeleton-containing polymer compound of the present invention can be easily controlled by adjusting a ratio of the total number of allyl groups in the phenol compound having two allyl groups of formula (10), the compound having two allyl groups of formula (11), and the compound having two allyl groups of formula (12) to the total number of hydrosilyl groups in the hydrogensilphenylene of formula (8) and the dihydroorganosiloxane of formula (9) (i.e., total allyl groups/total hydrosilyl groups). Alternatively, the weight average molecular weight can be easily controlled by polymerization of a specific epoxy-containing compound having two allyl groups, a specific phenol compound having two allyl groups, a specific isocyanuric acid skeleton-containing compound having two allyl groups, hydrogensilphenylene, and dihydroorganosiloxane while using a monoallyl compound (e.g., o-allylphenol), a monohydrosilane (e.g., triethylhydrosilane) or monohydrosiloxane as a molecular weight modifier.

Examples of the catalyst which can be used in the polymerization reaction include platinum group metal elements such as platinum (including platinum black), rhodium, and palladium; platinum chloride, chloroplatinic acid, and chloroplatinic acid salts such as $H_2PtCl_4 \cdot xH_2O$, $H_2PtCl_6 \cdot xH_2O$, $NaHPtCl_6 \cdot xH_2O$, $KHPtCl_6 \cdot xH_2O$, $Na_2PtCl_6 \cdot xH_2O$, $K_2PtCl_4 \cdot xH_2O$, $PtCl_4 \cdot xH_2O$, $PtCl_2$, $Na_2HPtCl_4 \cdot xH_2O$ (wherein x is preferably an integer of 0 to 6, particularly preferably 0 or 6); alcohol-modified chloroplatinic acid (U.S. Pat. No. 3,220,972); complexes of chloroplatinic acid with olefins (U.S. Pat. No. 3,159,601, U.S. Pat. No. 3,159,662, and U.S. Pat. No. 3,775,452); platinum group metals such as platinum black and palladium on supports such as alumina, silica and carbon; rhodium-olefin complexes; chlorotris(triphenylphosphine)rhodium (so-called Wilkinson's catalyst); and complexes of platinum chloride, chloroplatinic acid, or chloroplatinic acid salts with vinyl-containing siloxanes (particularly, vinyl-containing cyclic siloxanes).

The amount thereof to be used is a catalytic amount, and in general, it is preferably 0.001 to 0.1% by mass as a platinum group metal based on the total amount of the reaction polymer.

In the polymerization reaction, a solvent may be used, if necessary. Preferable examples of the solvent include hydrocarbon solvents such as toluene and xylene.

With respect to polymerization conditions, the polymerization temperature is preferably in the range of 40 to 150° C., more preferably 60 to 120° C. since the catalyst is not deactivated and the polymerization can be brought to completion in a short time.

Although the polymerization time depends on the type and amount of a desired polymer, polymerization is preferably completed within about 0.5 to 100 hours, more preferably about 0.5 to 30 hours, in order to prevent moisture entry into the polymerization system. After completion of the polymerization, the solvent is distilled off if the solvent is used. In this way, a silicone skeleton-containing polymer compound having a repeating unit shown by the general formula (7) can be prepared.

Hereinafter, the preferable method for synthesizing a bis(4-hydroxy-2-allylphenyl) derivative having an alcoholic hydroxyl group as shown by the general formula (12) or (13) will be described.

As one method for synthesizing the compound shown by the general formula (12), a compound having ketone and alcoholic hydroxyl group as shown by the general formula (15-1) may be used as a starting material,

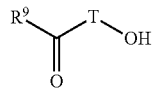

(15-1)

wherein $R^9$ and T have the same meanings as defined above.

First, the compound having ketone and alcoholic hydroxyl group as shown by the general formula (15-1) is condensed with two-equivalent phenol under acidic condition to obtain a bisphenol derivative having an alcoholic hydroxyl group as shown by the general formula

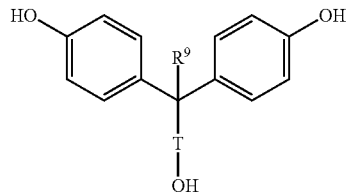

(15-2)

wherein $R^9$ and T have the same meanings as defined above.

Then, the bisphenol derivative having an alcoholic hydroxyl group as shown by the general formula (15-2) is reacted with two-equivalent halogenated allyl in a non-protic polar solvent under basic condition with potassium carbonate to obtain a compound in which hydrogen atoms of phenolic hydroxyl groups are substituted with an allyl group as shown by the general formula (15-3),

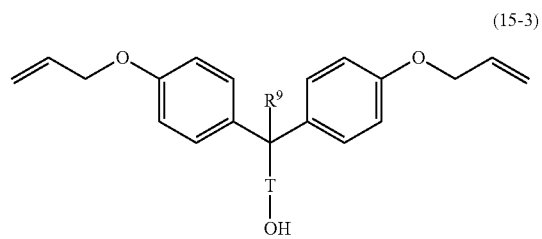

(15-3)

wherein $R^9$ and T have the same meanings as defined above.

The compound in which hydrogen atoms of phenolic hydroxyl groups are substituted with an allyl group as shown by the general formula (15-3) is dissolved in high-boiling point solvent such as dimethylaniline, and then heated at a high temperature about 180° C. to initiate Claisen rearrangement reaction, whereby a desired bis(4-hydroxy-2-allylphenyl) derivative having an alcoholic hydroxyl group as shown by the general formula (12), in which the allyl group migrates to 2-position of the phenol, can be obtained.

As other preferable method, the compound shown by the general formula (12) can be synthesized by using a compound having ketone and carboxylic acid as shown by the general formula (15-4) as a starting material,

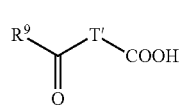

(15-4)

wherein $R^9$ has the same meaning as defined above; and T' represents a single bond or an alkylene group having 1 to 9 carbon atoms.

The compound having ketone and carboxylic acid as shown by the general formula (15-4) is condensed with two-equivalent phenol under acidic condition similarly to above, and thereby a bisphenol derivative having carboxylic acid as shown by the general formula (15-5) can be obtained,

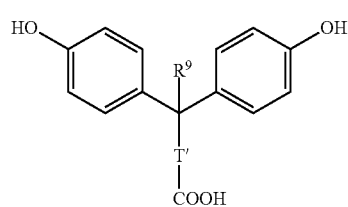

(15-5)

wherein $R^9$ and T' have the same meanings as defined above.

Further, the compound shown by the general formula (15-5) is reacted with three-equivalent halogenated allyl under the same condition as in the aforementioned method for obtaining allylether, to obtain a compound shown by the general formula (15-6). At this time, among the 3-equivalent halogenated allyl, 2-equivalent halogenated allyl serves to substitute hydrogen atoms of phenolic hydroxyl groups in the compound shown by the general formula (15-5) with an allyl group, while the other 1-equivalent halogenated allyl serves to substitute a hydrogen atom of the carboxylic acid in the compound shown by the general formula (15-5) with an allyl group, whereby a compound shown by the general formula (15-6) (carboxylic acid allyl ester) can be obtained,

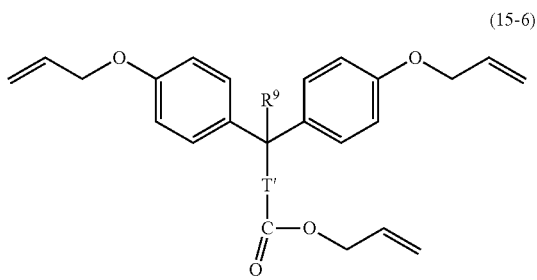

(15-6)

wherein $R^9$ and T' have the same meanings as defined above.

Further, the compound of formula (15-6) is dissolved in a non-protic polar solvent such as tetrahydrofuran and toluene, and 1-equivalent or more, preferably 1 to 1.5-equivalent of a Red-Al solution is added and stirred at 0 to 30° C., preferably 0 to 15° C. to readily perform reduction reaction of the carboxylic acid portion, thereby obtaining a compound shown by the general formula (15-7) equivalent to the compound shown by the general formula (15-3),

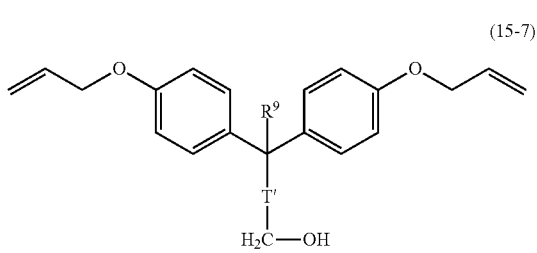

(15-7)

wherein $R^9$ and T' have the same meanings as defined above.

Subsequently, the compound shown by the general formula (15-7) is subjected to Claisen rearrangement reaction similarly to above, whereby a derivative shown by the general formula (15-8) equivalent to a desired bis(4-hydroxy-2-allylphenyl) derivative having an alcoholic hydroxyl group as shown by the general formula (12), in which the allyl group migrates to 2-position of the phenol, can be obtained,

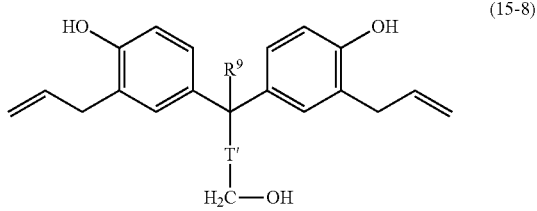

(15-8)

wherein $R^9$ and T' have the same meanings as defined above.

In a series of the methods for obtaining the bis(4-hydroxy-2-allylphenyl) derivative having an alcoholic hydroxyl group as shown by the general formula (12), a diphenolic acid (compound shown by the general formula (15-9)) is preferably used as the bisphenol derivative having carboxylic acid as shown by the general formula (15-5). That is, a diphenolic acid is a preferred starting material since it is industrially inexpensive and readily available.

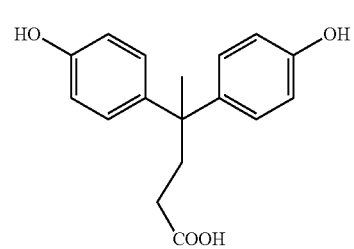

(15-9)

In the case that a diphenolic acid, which is a preferred raw material, is used, a bis(4-hydroxy-2-allylphenyl) derivative having an alcoholic hydroxyl group as shown by the formula (15-10) can be obtained, which is most preferably used for the "hydrosilylation" polymerization reaction.

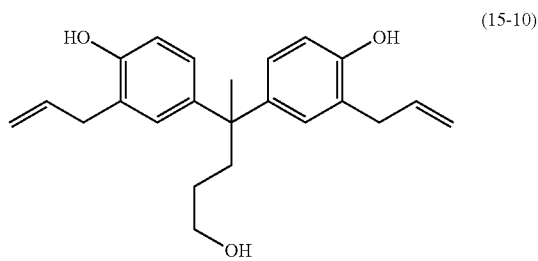 [SMILES: C=CCc1cc(C(C)(CCCO)c2ccc(O)c(CC=C)c2)ccc1O]

(15-10)

As to the phenol compound having two allyl groups as shown by the general formula (14), similarly, a compound having ketone as shown by the general formula (15-1) wherein T is a benzene ring is used as the starting material, thereby obtaining the compound having two allyl groups and a phenolic hydroxyl group as shown by the general formula (14). Preferable example of the compound shown by the general formula (15-1) to be used as the starting material include 4-hydroxyphthaldehyde and 4-hydroxyacetophenone. By the condensation of these starting materials with two-equivalent 2-allylphenol under acidic condition, the bis(4-hydroxy-2-allylphenyl) derivative having a phenolic hydroxyl group as shown by the general formula (14) can be obtained,

(15-1)

wherein $R^9$ and T have the same meanings as defined above,

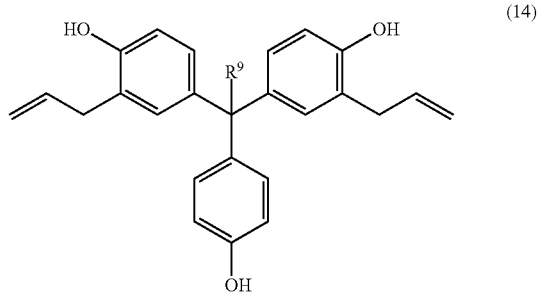

(14)

wherein $R^9$ has the same meaning as defined above.

Next, explanation is given about the reaction for introducing a carboxyl group by reacting a part or all of hydroxyl groups of the silicone skeleton-containing polymer compound having an alcoholic or phenolic hydroxyl group which is obtained by the hydrosilylation polymerization reaction with a dicarboxylic acid anhydride.

Indeed, it has been considered that the silicone skeleton-containing polymer compound of the present invention can be obtained by the hydrosilylation using a bis(4-hydroxy-2-allylphenyl) derivative having carboxylic acid as shown by the general formula (15-11). However, when the bis(4-hydroxy-2-allylphenyl) derivative having carboxylic acid as shown by the general formula (15-11) is used, Si—H group of the hydrogensilphenylene shown by the structural formula (8) and the dihydroorganosiloxane shown by the general formula (9) occasionally reacts with the above-mentioned carboxylic acid during the hydrosilylation polymerization reaction, so that the desired silicone skeleton-containing polymer compound of the present invention cannot be obtained. Accordingly, it is most preferable that after preparing a silicone skeleton-containing polymer compound having an alcoholic or phenolic hydroxyl group as intermediate, a part or all of alcoholic or phenolic hydroxyl group of the intermediate is reacted with a dicarboxylic acid anhydride to introduce a carboxyl group thereinto as mentioned above, whereby the silicone skeleton-containing polymer compound of the present invention can be obtained,

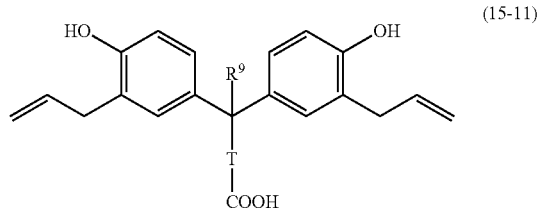

(15-11)

wherein $R^9$ and T have the same meanings as defined above.

For the reaction of a part or all of hydroxyl groups of the silicone skeleton-containing polymer compound having an alcoholic or phenolic hydroxyl group obtained by the hydrosilylation polymerization reaction, with a dicarboxylic acid anhydride, first, the obtained silicone skeleton-containing polymer compound is dissolved in a solvent having a weight 4 times of the compound. Then, an appropriate molar equivalent of dicarboxylic acid anhydride is added to molar ratios k and l of W in the general formula (7) (i.e., a unit having an alcoholic or phenolic hydroxyl group), and 1-equivalent triethylamine is added to the unit having an alcoholic or phenolic hydroxyl group. The resulting mixture is stirred at a temperature ranging from room temperature to 50° C. for several hours to perform the reaction, whereby a carboxyl group can be introduced into the silicone skeleton-containing polymer compound. The equivalent of the dicarboxylic acid anhydride to be reacted indicates a ratio of repeating units of formula (1) to repeating units of formula (7, i.e., (g+h)/(k+l). For example, if the dicarboxylic acid anhydride to be reacted is 1-equivalent, a carboxyl group is introduced to all alcoholic hydroxyl groups of W unit in the general formula (7), which leads to the general formula (1) wherein e=0 and f=0. The introducing ratio of carboxyl group, i.e., the preferable ranges of "g" and "h" in the general formula (1) are as described above.

The carboxylic acid thus introduced is shown by U in the general formula (1), and U is shown by the general formula (5). Further, $R^{10}$ in the general formula (5) can be shown by the general formula (6),

(6)

wherein the dotted line represents a bond; $R^{11}$ to $R^{14}$ may be the same or different and represent a hydrogen atom, a halogen atom, a linear, branched, or cyclic alkyl group having 1 to 12 carbon atoms, or an aromatic group; $R^{11}$ and $R^{13}$ may be bonded respectively to $R^{12}$ and $R^{14}$ to form a substituted or unsubstituted ring structure having 1 to 12 carbon atoms; and "j" is any of 1 to 7.

The dicarboxylic acid anhydride to be reacted with a part or all of hydroxyl groups of the silicone skeleton-containing polymer compound having an alcoholic or phenolic hydroxyl group can be shown by the general formula (16),

(16)

wherein $R^{11}$ to $R^{14}$ and "j" have the same meanings as defined above.

Preferable examples of the dicarboxylic acid anhydride include succinic anhydride, phthalic anhydride, maleic anhydride, itaconic anhydride, glutaric anhydride, adipic anhydride, pimelic anhydride, suberic anhydride, azelaic anhydride, sebacic anhydride, and compounds having the following structure.

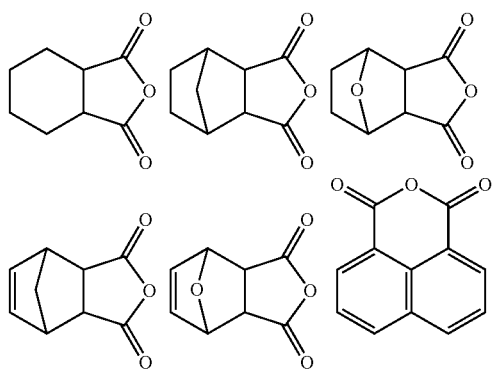

The thus-obtained silicone skeleton-containing polymer compound having the structure shown by the general formula (5) is suitable to the base resin of the chemically amplified negative resist composition, and can remedy the problem of delamination generated on a metal wiring such as Cu and Al, an electrode, and a substrate, especially on a substrate such as SiN. The reason why the delamination is improved is considered that the structural part shown by the general formula (5), which has been introduced to the silicone skeleton-containing polymer compound, improves the interaction with a substrate. When a pattern is formed by using a chemically amplified negative resist composition containing a silicone skeleton-containing polymer compound without the structural part shown by the general formula (5), the pattern is extremely inferior in adhesiveness to substrate.

On the other hand, the introduction of the structural part shown by the general formula (5) into the silicone skeleton-containing polymer compound results in improvement of solubility in aqueous alkaline developer such as a tetramethyl ammonium hydroxide (TMAH) aqueous solution, which is widely used for a chemically amplified negative resist composition. The chemically amplified negative resist composition requires a high solubility of the unexposed part in a developer. That is, in the development of a fine pattern, if the solubility of the unexposed part in a developer is low, an undissolved residue in the pattern bottom and a footing profile between the pattern and the substrate may occur. However, when a pattern is formed by using the chemically amplified negative resist composition containing the silicone skeleton-containing polymer compound of the present invention, the solubility of the unexposed part in an aqueous alkaline developer is improved, and therefore, the problems such as the occurrence of an undissolved residue in the pattern bottom and a footing profile can be resolved, as mentioned above.

Also, the other silicone skeleton-containing polymer compound of the present invention contains a repeating unit shown by the general formula (24) and has a weight average molecular weight of 3,000 to 500,000.

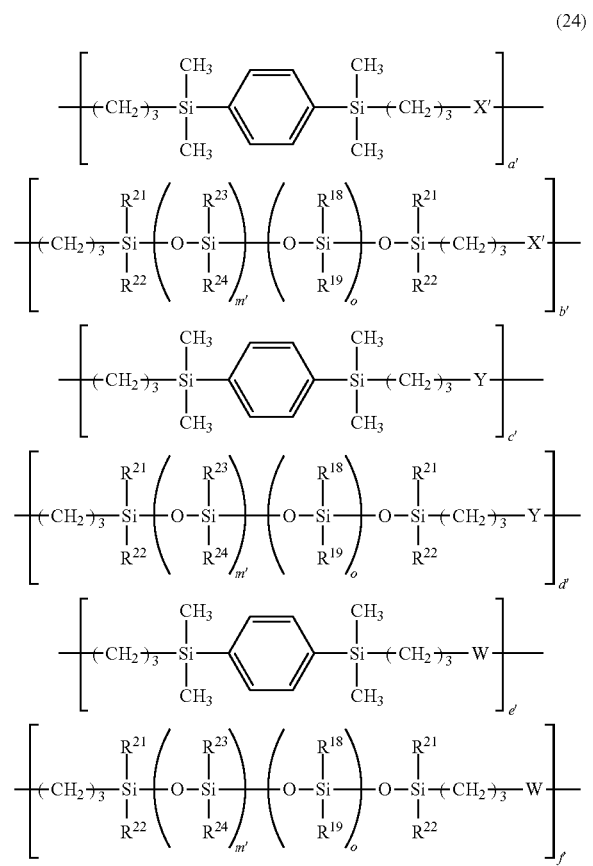

(24)

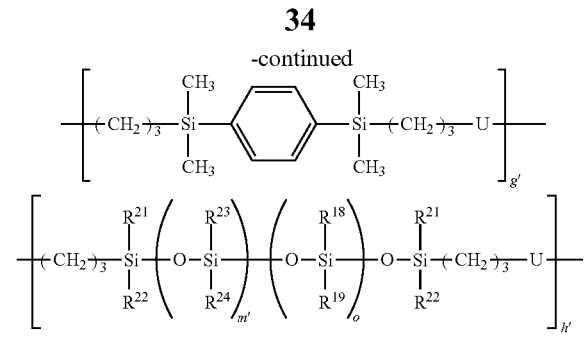

In the general formula (24), $R^{21}$ to $R^{24}$ may be the same or different and represent a monovalent organic group having 1 to 15 carbon atoms, preferably 1 to 10 carbon atoms, and optionally containing an oxygen atom; and $R^{18}$ and $R^{19}$ may be the same or different and represent a monovalent organic group having 1 to 28 carbon atoms, preferably 1 to 15 carbon atoms, more preferably 1 to 10 carbon atoms, and optionally containing an oxygen atom. Illustrative examples thereof include linear, branched or cyclic alkyl groups such as a methyl group, an ethyl group, a propyl group, an isopropyl group, a n-butyl group, a tert-butyl group, and a cyclohexyl group; linear, branched or cyclic alkenyl groups such as a vinyl group, an allyl group, a propenyl group, a butenyl group, a hexenyl group, and a cyclohexenyl group; aryl groups such as a phenyl group and a tolyl group; and aralkyl groups such as a benzyl group, a phenethyl group, and a methoxy phenethyl group. m' is an integer of 0 to 100; and "o" is an integer of 0 to 100. c', d', e', and f' are each 0 or a positive number, and a', b', g' and h' are each a positive number, provided that a'+b'+c'+d'+e'+f'+g'+h'=1. X' is a divalent organic group shown by the general formula (25) or the general formula (26); Y is a divalent organic group shown by the general formula (3); W is a divalent organic group shown by the general formula (4); and U is a divalent organic group shown by the general formula (5),

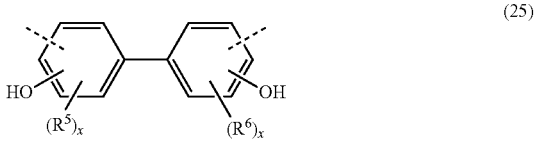

(25)

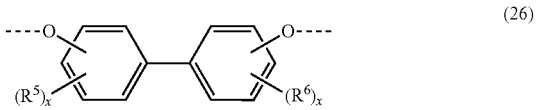

(26)

wherein the dotted line represents a bond; $R^5$ and $R^6$ each represent an alkyl group or alkoxy group having 1 to 4 carbon atoms and may be the same or different; and "x" is 0, 1, or 2;

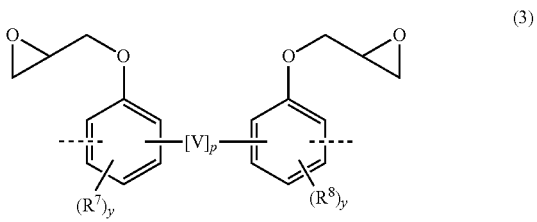

(3)

wherein V represents a divalent organic group selected from any of

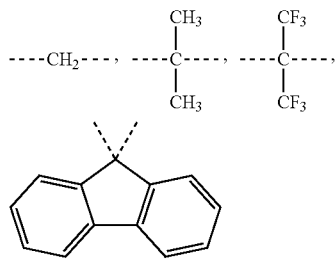

the dotted line represents a bond; "p" is 0 or 1; $R^7$ and $R^8$ each represent an alkyl group or alkoxy group having 1 to 4 carbon atoms and may be the same or different; and "y" is 0, 1, or 2;

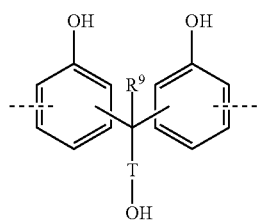
(4)

wherein the dotted line represents a bond; T represents an alkylene group having 1 to 10 carbon atoms or a divalent aromatic group; and $R^9$ represents a hydrogen atom or a methyl group;

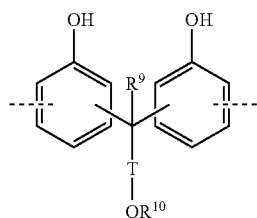
(5)

wherein the dotted line represents a bond; T and $R^9$ have the same meanings as defined above; and $R^{10}$ represents a monovalent carboxyl-containing organic group.

In addition, it is preferred that in the general formula (24), "o" is an integer of 1 to 100, more preferably 1 to 80; $R^{21}$ to $R^{24}$ may be the same or different and represent a monovalent hydrocarbon group having 1 to 8 carbon atoms; $R^{18}$ represents a phenyl substituent containing a hydroxyl group or an alkoxy group and shown by the general formula (27); and $R^{19}$ may be the same as or different from $R^{21}$ to $R^{24}$ and represents a monovalent organic group having 1 to 10 carbon atoms and optionally containing an oxygen atom, more preferably a monovalent hydrocarbon group having 1 to 8 carbon atoms, or $R^{19}$ may be the same as or different from $R^{18}$ and represents a phenyl substituent containing a hydroxyl group or an alkoxy group and shown by the general formula (27),

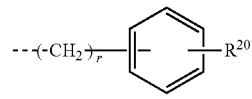
(27)

wherein "r" is an integer of 0 to 10; $R^{20}$ represents a hydroxyl group or a linear, branched, or cyclic alkoxy group having 1 to 12 carbon atoms.

In the phenyl substituent shown by the general formula (27), the hydroxyl group or the alkoxy group may be substituted in any of o-, m-, and p-positions. If $R^{20}$ represents an alkoxy group, the number of carbon atoms is 1 to 12, preferably 1 to 4.

The phenyl substituent shown by the general formula (27) may be specifically exemplified by groups shown by the formula (28). In the formula (28), the line with a wavy line: ⅹ represents a bonding arm.

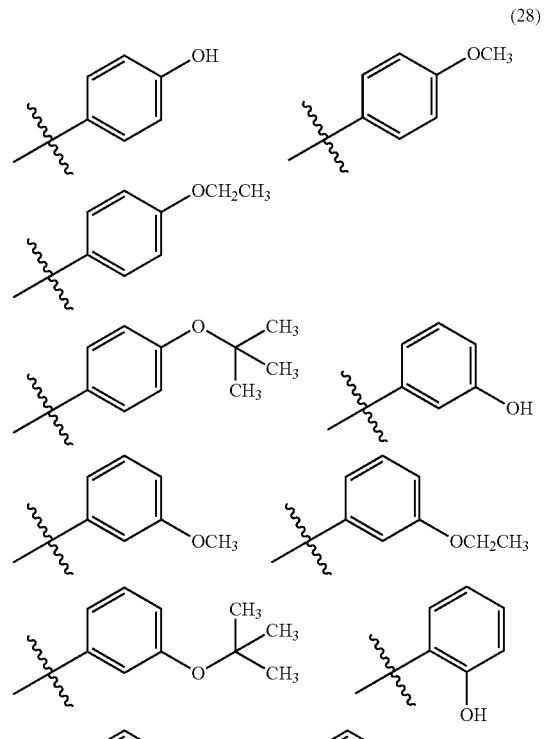
(28)

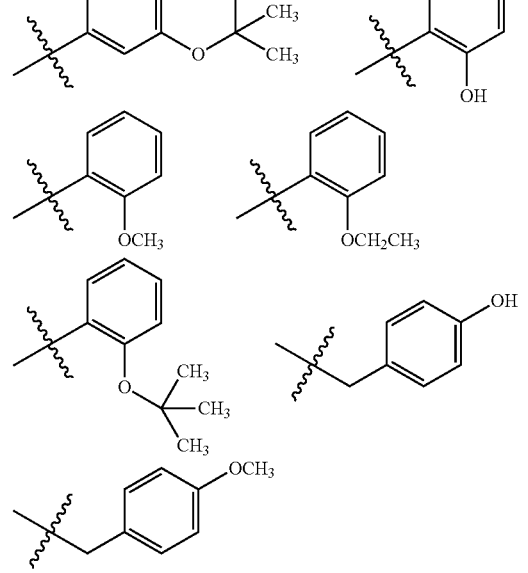

-continued

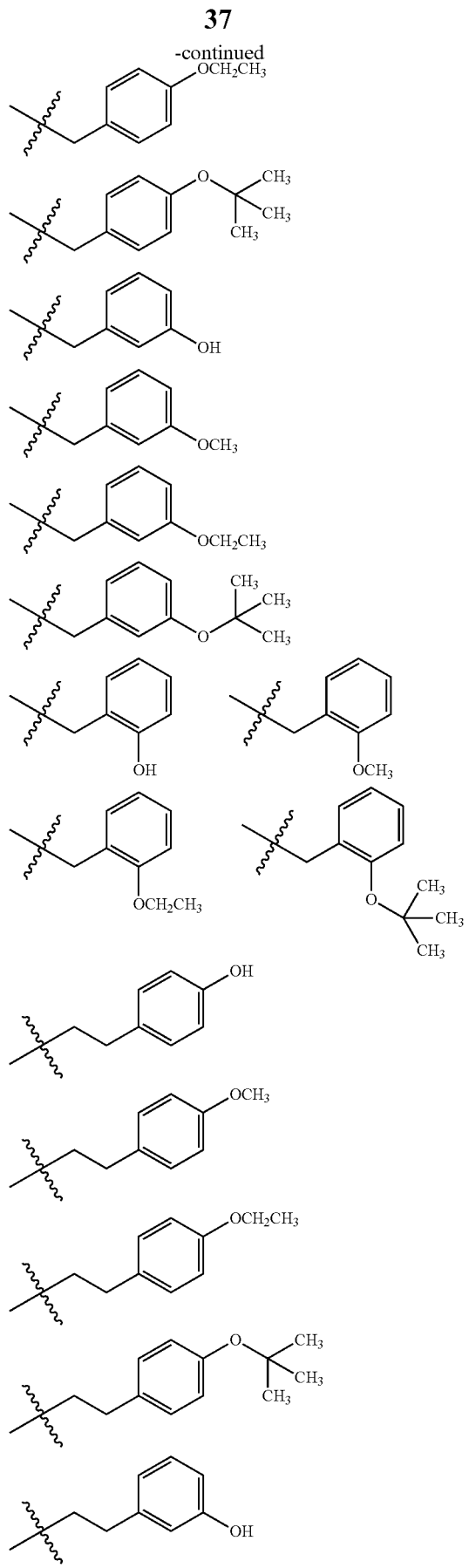

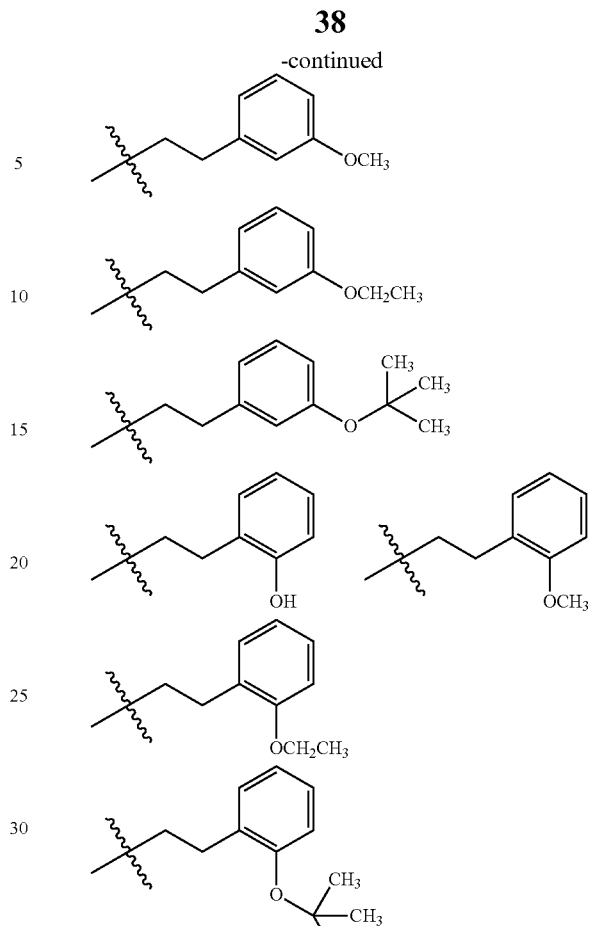

For example, such a silicone skeleton-containing polymer compound has biphenol skeleton shown by the general formula (25) or (26). The above-mentioned silicone skeleton-containing polymer compound of the present invention is suitable to the base resin of a chemically amplified negative resist composition, and can remedy the problem of delamination generated on a metal wiring such as Cu and Al, an electrode, and a substrate, especially on a substrate such as SiN.

Also, when the structural part shown by the general formula (25) or (26) is introduced into the silicone skeleton-containing polymer compound, its rigid structure with a low degree of freedom provides high Tg, excellent mechanical strength, and reliability to the cured film, and its compact structure allows improvement of the solubility in aqueous alkaline developer such as a tetramethyl ammonium hydroxide (TMAH) aqueous solution, which is widely used for a chemically amplified negative resist composition.

On the other hand, when the inventive silicone skeleton-containing polymer compound having the phenyl substituent shown by the general formula (27) is used as the base resin of a chemically amplified negative resist composition, crosslinking reactivity of the exposed part can be improved in the pattern formation. This is considered because the crosslinking point in the silicone skeleton-containing polymer compound is remarkably increased due to the additional crosslinking point on the siloxane, and thus the reaction with a later-described crosslinking agent progresses more greatly. In this way, the improvement in crosslinking reactivity of the exposed part causes a low solubility of the exposed part in developer.

As mentioned above, by using the silicone skeleton-containing polymer compound of the present invention as the base resin of a chemically amplified negative resist composition, solubility of the unexposed part in the developer can be improved, and further, the solubility of the exposed part in the developer can be extremely reduced. Thus, difference in dissolution rate between the exposed part and the unexposed part can be increased, and the dissolution contrast can be enhanced. Accordingly, a finer pattern formation is expected. That is, the silicone skeleton-containing polymer compound of the present invention is suitable to the base resins of the chemically amplified negative resist composition.

Further, the present invention provides a chemically amplified negative resist composition comprising:
(A) the above-mentioned silicone skeleton-containing polymer compound,
(B) a photosensitive acid generator capable of generating an acid by decomposition with light having a wavelength of 190 to 500 nm;
(C) one or more crosslinking agents selected from an amino condensate modified by formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted by a glycidyl group, a polyhydric phenol compound in which a hydrogen atom of a phenolic hydroxyl group is substituted by a substituent shown by the formula (C-1), and a compound having two or more nitrogen atoms bonded to a glycidyl group and shown by the formula (C-2),

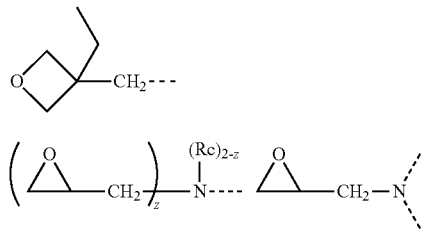

wherein the dotted line represents a bond; $R_c$ represents a linear, branched, or cyclic alkyl group having 1 to 6 carbon atoms; and "z" is 1 or 2;
(D) a solvent; and
(E) a basic compound.

As to (B) the photosensitive acid generator, a compound capable of generating an acid by exposure to light having a wavelength of 190 to 500 nm thereby serving as a curing catalyst may be used. The silicone skeleton-containing polymer compound of the present invention has excellent compatibility with the photosensitive acid generators, so that various photosensitive acid generators can be used. Illustrative examples of the photosensitive acid generator include an onium salt, a diazomethane derivative, a glyoxime derivative, a β-ketosulfone derivative, a disulfone derivative, a nitrobenzylsulfonate derivative, a sulfonate ester derivative, an imide-yl-sulfonate derivative, an oximesulfonate derivative, an iminosulfonate derivative, and a triazine derivative.

The onium salt may be exemplified by a compound shown by the general formula (17), $$(R^{15})_{j'}M^+K^- \qquad (17)$$

wherein $R^{15}$ represents an optionally substituted linear, branched, or cyclic alkyl group having 1 to 12 carbon atoms, an aryl group having 6 to 12 carbon atoms, or an aralkyl group having 7 to 12 carbon atoms; $M^+$ represents an iodonium or an sulfonium; and $K^-$ represents a non-nucleophilic counter ion; and j' is 2 or 3.

In the above-mentioned $R^{15}$, illustrative examples of the alkyl group include a methyl group, an ethyl group, a propyl group, a butyl group, a cyclohexyl group, a 2-oxocyclohexyl group, a norbornyl group, and an adamantyl group. Illustrative examples of the aryl group include a phenyl group; alkoxy phenyl groups such as an o-, m-, or p-methoxyphenyl group, an o-, m-, or p-ethoxyphenyl group, and a m- or p-tert-butoxyphenyl group; and alkyl phenyl groups such as a 2-, 3-, or 4-methylphenyl group, a 2-, 3-, or 4-ethylphenyl group, a 4-tert-butylphenyl group, a 4-butylphenyl group, and a dimethylphenyl group. Illustrative examples of the aralkyl group include a benzyl group and a phenethyl group.

Illustrative examples of the non-nucleophilic counter ion $K^-$ include halide ions such as a chloride ion and a bromide ion; fluoroalkyl sulfonates such as triflate, 1,1,1-trifluoroethane sulfonate, and nonafluorobutane sulfonate; aryl sulfonates such as tosylate, benzenesulfonate, 4-fluorobenzenesulfonate, and 1,2,3,4,5-pentafluorobenzenesulfonate; and alkyl sulfonates such as mesylate and butanesulfonate.

The diazomethane derivative may be exemplified by a compound shown by the general formula (18), N2

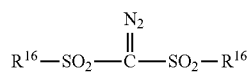

wherein $R^{16}$ represents may be the same or different and represent a linear, branched, or cyclic alkyl group or halogenated alkyl group having 1 to 12 carbon atoms, an aryl group or halogenated aryl group having 6 to 12 carbon atoms, or an aralkyl group having 7 to 12 carbon atoms.

In the above-mentioned $R^{16}$, illustrative examples of the alkyl group include a methyl group, an ethyl group, a propyl group, a butyl group, an amyl group, a cyclopentyl group, a cyclohexyl group, a norbornyl group, and an adamantyl group. Illustrative examples of the halogenated alkyl group include a trifluoromethyl group, a 1,1,1-trifluoroethyl group, a 1,1,1-trichloroethyl group, and a nonafluorobutyl group. Illustrative example of the aryl group includes a phenyl group; alkoxyphenyl groups such as an o-, m-, or p-methoxyphenyl group, an o-, m-, or p-ethoxyphenyl group, and a m- or p-tert-butoxyphenyl group; and alkylphenyl groups such as a 2-, 3-, or 4-methylphenyl group, a 2-, 3-, or 4-ethylphenyl group, a 4-tert-butylphenyl group, a 4-butylphenyl group, and a dimethylphenyl group. Illustrative examples of the halogenated aryl group include a fluorophenyl group, a chlorophenyl group, and a 1,2,3,4,5-pentafluorophenyl group. Illustrative examples of the aralkyl group include a benzyl group and a phenethyl group.

Illustrative examples of the photosensitive acid generator include onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluolobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, and diphenyl(4-thiophenoxyphenyl)sulfonium hexafluoroantimonate; diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane; glyoxime derivatives such as bis-o-(p-toluenesulfonyl)-α-dimethyl glyoxime, bis-o-(p-toluenesulfonyl)-α-diphenyl glyoxime, bis-o-(p-toluenesulfonyl)-α-dicyclohexyl glyoxime, bis-o-(p-toluenesulfonyl)-2,3-pentanedione glyoxime, bis-(p-toluenesulfonyl)-2-methyl-3,4-pentanedione glyoxime, bis-o-(n-butanesulfonyl)-α-dimethyl glyoxime, bis-o-(n-butanesulfonyl)-α-diphenyl glyoxime, bis-o-(n-butanesulfonyl)-α-dicyclohexyl glyoxime, bis-o-(n-butanesulfonyl)-2,3-pentanedione glyoxime, bis-o-(n-butanesulfonyl)-2-methyl-3,4-pentanedione glyoxime, bis-o-(methanesulfonyl)-α-dimethyl glyoxime, bis-o-(trifluoromethanesulfonyl)-α-dimethyl glyoxime, bis-o-(1,1,1-trifluoroethanesulfonyl)-α-dimethyl glyoxime, bis-o-(tert-butanesulfonyl)-α-dimethyl glyoxime, bis-o-(perfluorooctanesulfonyl)-α-dimethyl glyoxime, bis-o-(cyclohexanesulfonyl)-α-dimethyl glyoxime, bis-o-(benzenesulfonyl)-α-dimethyl glyoxime, bis-o-(p-fluorobenzenesulfonyl)-α-dimethyl glyoxime, bis-o-(p-tert-butylbenzenesulfonyl)-α-dimethyl glyoxime, bis-o-(xylenesulfonyl)-α-dimethyl glyoxime, and bis-o-(camphersulfonyl)-α-dimethyl glyoxime; oxime sulfonate derivatives such as α-(benzenesulfoniumoxyimino)-4-methylphenylacetonitrile; β-keto sulfone derivatives such as 2-cyclohexylcarbonyl-2-(p-toluenesulfonyl propane and 2-isopropylcarbonyl-2-(p-toluenesulfonyl) propane; disulfone derivatives such as diphenyl disulfone and dicyclohexyl disulfone; nitrobenzyl sulfonate derivatives such as 2,6-dinitrobenzyl p-toluenesulfonate and 2,4-dinitrobenzyl p-toluenesulfonate; sulfonate ester derivatives such as 1,2,3-tris(methanesulfonyloxy)benzene, 1,2,3-tris(trifluoromethanesulfonyloxy)benzene and 1,2,3-tris(p-toluenesulfonyloxy)benzene; imide-yl-sulfonate derivatives such as phthalimide-yl-triflate, phthalimide-yl-tosylate, 5-norbornene 2,3-dicarboxyimide-yl-triflate, 5-norbornene 2,3-dicarboxyimide-yl-tosylate, 5-norbornene 2,3-dicarboxyimide-yl-n-butylsulfonate, and n-trifluoromethylsulfonyloxy naphthylimide; iminosulfonates such as (5-(4-methylphenyl)sulfonyloxyimino-5H-thiophene 2-ylidene)-(2-methylphenyl)acetonitrile and (5-(4-4-methylphenylsulfonyloxy) phenylsulfonyloxyimino-H thiophene-2-ylidene)-(2-methylphenyl)acetonitrile; and 2-methyl-2[(4-methylthiophenyl)sulfonyl]-1-[(4-methylthio)phenyl]-1-propane. Among them, imide-yl-sulfonates, iminosulfonates, and oximesulfonates are preferably used.

Meanwhile, these photosensitive acid generators can be used solely or as a mixture of two or more kinds.

In view of the light absorption of the photosensitive acid generator itself and photo-curability in a thick film, amount of the photosensitive acid generator to be blended is preferably in the range of 0.05 to 20 parts by mass, or especially preferably in the range of 0.2 to 5 parts by mass, based on 100 parts by mass of (A) the silicone skeleton-containing polymer compound.

As to (C) the crosslinking agent, one or more crosslinking agents selected from an amino condensate modified by formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted by a glycidyl group, a polyhydric phenol compound in which a hydrogen atom of a phenolic hydroxyl group is substituted by a substituent shown by the formula (C-1), and a compound having two or more nitrogen atoms bonded to a glycidyl group and shown by the formula (C-2), may be used,

(C-1)

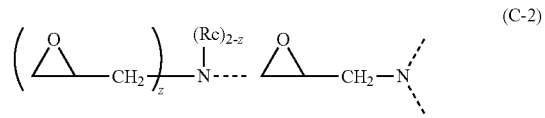

(C-2)

wherein the dotted line represents a bond; $R_c$ represents a linear, branched, or cyclic alkyl group having 1 to 6 carbon atoms; and "z" is 1 or 2.

The amino condensate modified by formaldehyde or formaldehyde-alcohol may be exemplified by melamine condensates modified by formaldehyde or formaldehyde-alcohol and urea condensates modified by formaldehyde or formaldehyde-alcohol.

To prepare a melamine condensate modified by formaldehyde or formaldehyde-alcohol, for example, a melamine monomer is modified with formalin into a methylol form, and optionally, the resultant compound is further modified with an alcohol into an alkoxy form according to a known method, thereby obtaining a modified melamine shown by the formula (19). In this case, lower alcohols such as an alcohol having 1 to 4 carbon atoms are preferred as the alcohol.

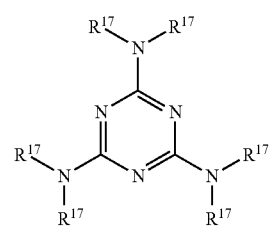

(19)

In the above formula, each $R^{17}$ may be the same or different, and represents a methylol group, an alkoxymethyl group containing an alkoxy group having 1 to 4 carbon atoms, or a hydrogen atom, provided that one or more of them is a methylol group or an alkoxymethyl group.

Examples of $R^{17}$ include a methylol group, alkoxymethyl groups such as a methoxymethyl group and an ethoxymethyl group, and a hydrogen atom.

Illustrative examples of the modified melamine shown by the formula (19) include trimethoxymethyl monomethylol melamine, dimethoxymethyl monomethylol melamine, trimethylol melamine, hexamethylol melamine, and hexamethoxymethylol melamine.

Then, the modified melamine shown by the formula (19) or the multimeric compound thereof (e.g. oligomer including dimer and trimer) is polymerized by addition condensation with formaldehyde until a desired molecular weight is achieved according to a known method, thereby obtaining the melamine condensate modified by formaldehyde or formaldehyde-alcohol.

Also, a urea condensate modified with formaldehyde or formaldehyde-alcohol can be prepared by modifying a urea condensate having a desired molecular weight with formaldehyde into a methylol form, and optionally, further modifying the resultant compound with an alcohol into an alkoxy form, according to a known method.

Illustrative examples of the urea condensate modified with formaldehyde or formaldehyde-alcohol include a methoxymethylated urea condensate, an ethoxymethylated urea condensate, and a propoxymethylated urea condensate.

These modified melamine condensates and modified urea condensates may be used solely or as a mixture of two or more kinds.

The phenol compound having on average two or more methylol groups or alkoxymethylol groups per molecule may be exemplified by (2-hydroxy-5-methyl)-1,3-benzenedimethanol, 2,2',6,6'-tetramethoxymethyl bisphenol A, compounds shown by the formulae (C-3) to (C-7), and the like.

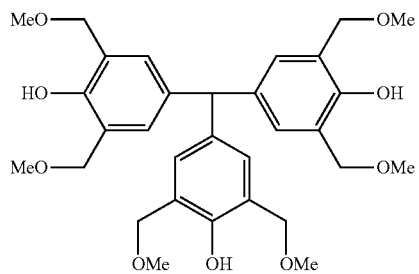

C-3

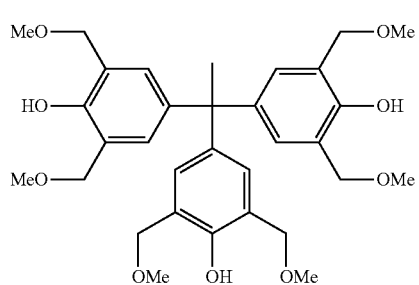

C-4

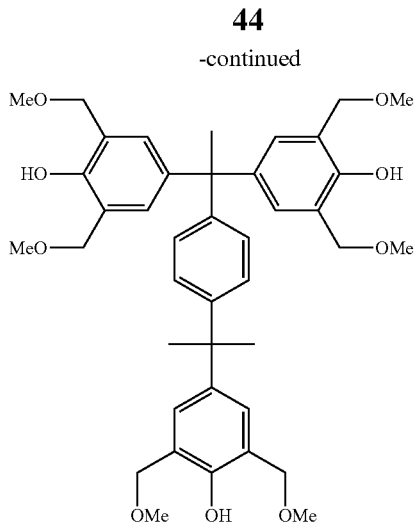

C-5

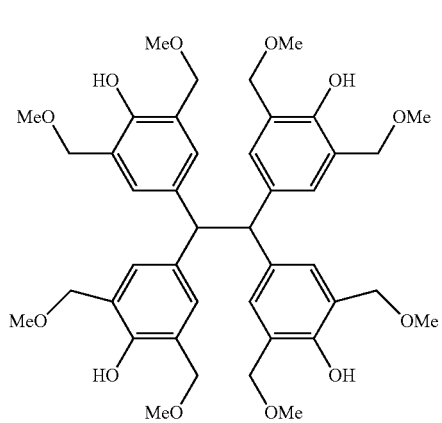

C-6

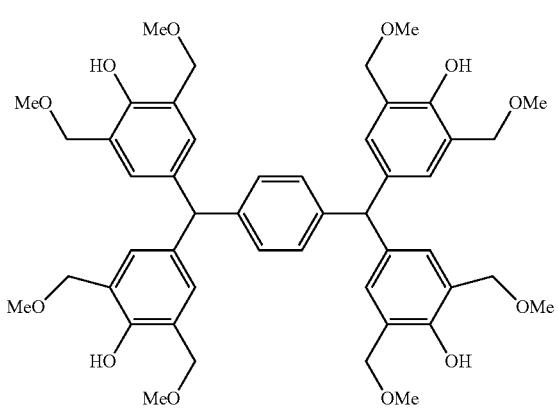

C-7

The polyhydric phenol compound in which a hydrogen atom of a phenolic hydroxyl group is substituted by a glycidyl group may be exemplified by compounds that are obtained by reacting a hydroxyl group of bisphenol A, tris(4-hydroxyphenyl)methane, or 1,1,1-tris(4-hydroxyphenyl)ethane with epichlorohydrin in the presence of a base catalyst. Preferable examples of the polyhydric phenol compound in which a hydrogen atom of a phenolic hydroxyl group is substituted by a glycidyl group include compounds shown by the formulae (C-8) to (C-14), C-8
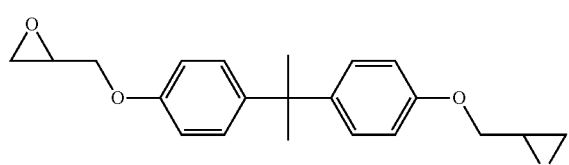

C-9
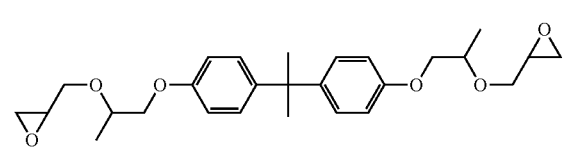

C-10
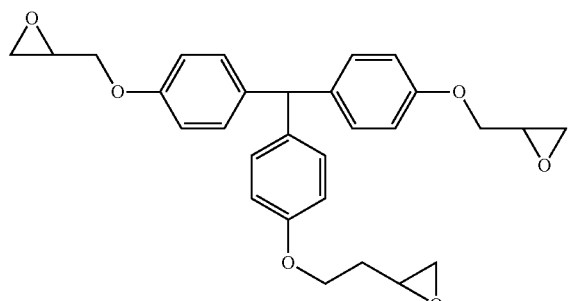

C-11
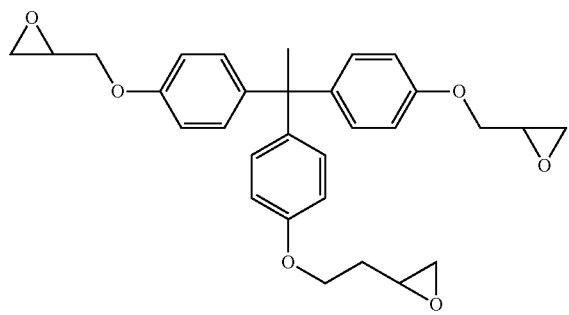

C-12
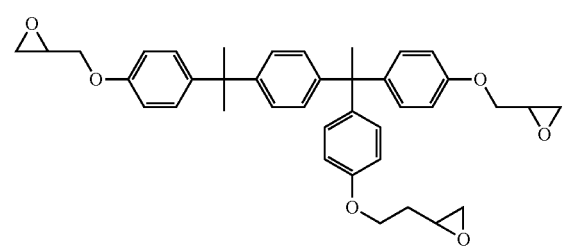

C-13
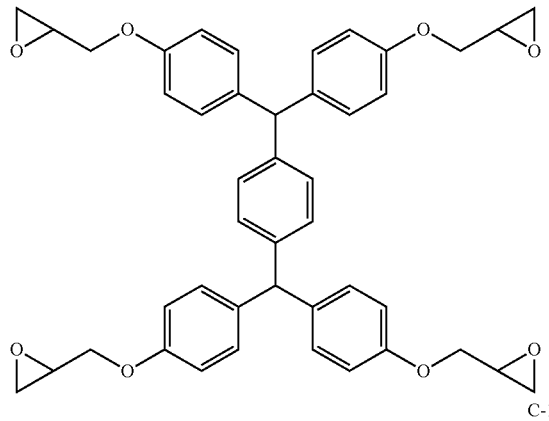

C-14
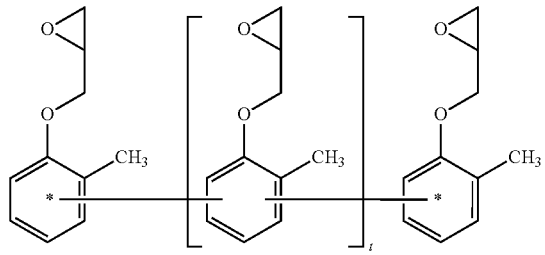

wherein 2≤t≤3.

These polyhydric phenol compounds in which a hydrogen atom of a phenolic hydroxyl group is substituted by a glycidyl group may be used as a crosslinking agent solely or as a mixture of two or more kinds.

Also, the polyhydric phenol compound in which a hydrogen atom of a phenolic hydroxyl group is substituted by a substituent shown by the formula (C-1) and containing two or more of the substituents may be exemplified by a compound shown by the formula (C-15), (C-1)
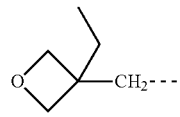

wherein the dotted line represents a bond, (C-15)
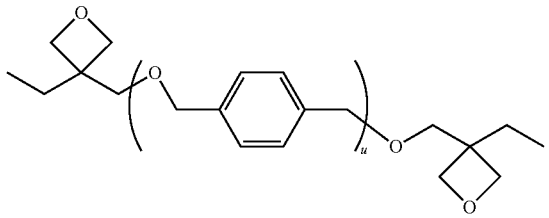

wherein 1≤u≤3.

On the other hand, the compound having two or more nitrogen atoms bonded to a glycidyl group and shown by the formula (C-2) may be exemplified by a compound shown by the formula (C-16),

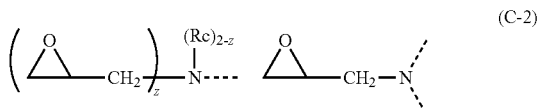
(C-2)

wherein the dotted line represents a bond; $R_c$ represents a linear, branched, or cyclic alkyl group having 1 to 6 carbon atoms; and "z" is 1 or 2,

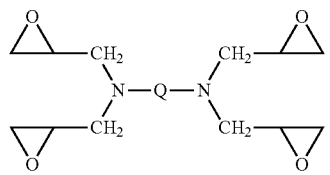
(C-16)

wherein Q represents a linear, branched, or cyclic alkylene group having 2 to 12 carbon atoms, or a divalent aromatic group.

Illustrative examples of the compound shown by the formula (C-16) include compounds shown by the formulae (C-17) to (C-20).

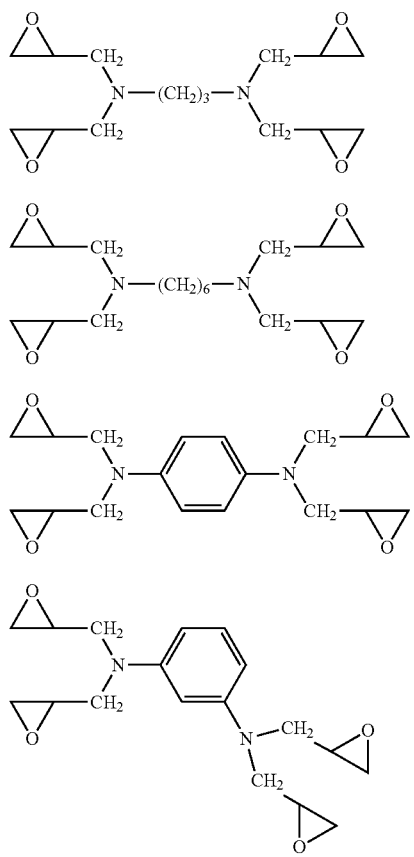

C-17

C-18

C-19

C-20

Other examples of the compound having two or more nitrogen atoms bonded to a glycidyl group and shown by the formula (C-2) include a compound shown by the formula (C-21).

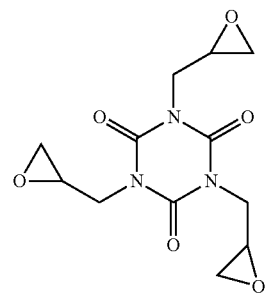
C-21

These compounds having two or more nitrogen atoms bonded to a glycidyl group and shown by the formula (C-2) may be used as a crosslinking agent solely or as a mixture of two or more kinds.

The above-mentioned crosslinking agent serves to initiate the curing reaction with (A) the silicone skeleton-containing polymer compound, facilitates the pattern formation, and enhances strength of the cured product. The weight average molecular weight of the crosslinking agent is preferably in the range of 150 to 10,000, particularly preferably 200 to 3,000, in view of photo-curability and heat resistance.

The crosslinking agent may be used solely or a mixture of two or more kinds.

Also, in view of photo-curability and reliability as the top coat to protect electric and electronic parts after post-cure, the amount of the crosslinking agent to be blended is preferably in the range of 0.5 to 50 parts by mass, more preferably 1 to 30 parts by mass based on 100 parts by mass of (A) the silicone skeleton-containing polymer compound.

As to (D) the solvent, those capable of dissolving (A) the silicone skeleton-containing polymer compound, (B) the photosensitive acid generator, and (C) the crosslinking agent can be used.

Illustrative examples of the solvent include ketones such as cyclohexanone, cyclopentanone, and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, and γ-butyrolactone; and these may be used one or more kinds. Among them, ethyl lactate, cyclohexanone, cyclopentanone, propylene glycol monomethyl ether acetate, and γ-butyrolactone, or a mixture of them are particularly preferred, because these materials have the utmost solubility to the photosensitive acid generator.

In view of compatibility, viscosity, and coating properties of the chemically amplified negative resist composition, the amount of the solvent to be blended is preferably in the range of 50 to 2,000 parts by mass, more preferably 100 to 1,000 parts by mass based on 100 parts by mass of the total amount of (A) the silicone skeleton-containing polymer compound, (B) the photosensitive acid generator, and (C) the crosslinking agent.

Moreover, in the chemically amplified negative resist composition of the present invention, (E) a basic compound may be added if necessary. As the basic compound, a compound capable of suppressing diffusion rate of an acid that is generated from the photosensitive acid generator in the resist film is suitable. By blending the basic compound like this, the resolution can be enhanced, the sensitivity change after exposure can be suppressed, and dependence on a substrate and an environment can be made small, so that the exposure allowance, the pattern shape, and the like may be improved.

Illustrative examples of the basic compound include primary, secondary, and tertiary aliphatic amines, mixed amines, aromatic amines, heterocyclic amines, a nitrogen-containing compound having a carboxyl group, a nitrogen-containing compound having a sulfonyl group, a nitrogen-containing compound having a hydroxyl group, a nitrogen-containing compound having a hydroxyphenyl group, a nitrogen-containing alcoholic compound, an amide derivative, an imide derivative, and a compound shown by the general formula (20).

(20)

In the above formula, "q" is 1, 2, or 3. The side chain α may be the same or different and represents a substituent shown by any of the general formulae (21) to (23). The side chain β may be the same or different and represents a hydrogen atom, or a linear, branched, or cyclic alkyl group having 1 to 20 carbon atoms and optionally containing an ether bond or a hydroxyl group. Further, the side chains a may be bonded with each other to form a ring,

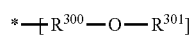

(21)

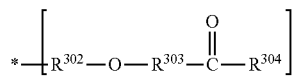

(22)

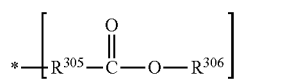

(23)

wherein $R^{300}$, $R^{302}$, $R^{305}$ represent a linear or branched alkylene group having 1 to 4 carbon atoms; and R ad represent a hydrogen atom, or a linear, branched, or cyclic alkyl group having 1 to 20 carbon atoms and optionally containing one or a plurality of a hydroxyl group, an ether bond, an ester bond, and a lactone ring. $R^{303}$ represents a single bond, or a linear or branched alkylene group having 1 to 4 carbon atoms; and $R^{30}$ represents a linear, branched, or cyclic alkyl group having 1 to 20 carbon atoms and optionally containing one or a plurality of a hydroxyl group, an ether bond, an ester bond, and a lactone ring. Meanwhile, the symbol * shows the bond terminal.

Illustrative examples of the primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Illustrative examples of the secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylene diamine, N,N-dimethylethylene diamine, and N,N-dimethyltetraethylene pentamine.

Illustrative examples of the tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylene diamine, N,N,N',N'-tetramethylethylene diamine, and N,N,N',N'-tetramethyltetraethylene pentamine.

Illustrative examples of the mixed amines include dimethylethylamine, methylethylpropylamine, benzylamine, phenethylamine, and benzyldimethylamine.

Illustrative examples of the aromatic amines and the heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-burylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pirazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Illustrative examples of the nitrogen-containing compound having a carboxyl group include amino benzoic acid, indole carboxylic acid, and amino acid derivatives (e.g., nicotinic acid, alanine, arginine, aspartic acid, glutamic acid, glycine, histidine, isoleucine, glycyl leucine, leucine, methionine, phenylalanine, threonine, lysine, 3-aminopyrazine-2-carboxylic acid, and methoxy alanine).

Illustrative examples of the nitrogen-containing compound having a sulfonyl group include 3-pyridinesulfonic acid and pyridinium p-toluenesulfonate.

Illustrative examples of the nitrogen-containing compound having a hydroxyl group, the nitrogen-containing compound having a hydroxyphenyl group, and the nitrogen-containing alcoholic compound include 2-hydroxy pyridine, amino cresol, 2,4-quinoline diol, 3-indole methanol hydrate, monoethanol amine, diethanol amine, triethanol amine, N-ethyl diethanol amine, N,N-diethyl ethanol amine, triisopropanol amine, 2,2'-imino diethanol, 2-amino ethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propane diol, 3-pyrrolidino-1,2-propane diol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotine amide.

Illustrative examples of the amide derivative include formamide, N-methyl formamide, N,N-dimethyl formamide, acetamide, N-methyl acetamide, N,N-dimethyl acetamide, propione amide, and benzamide.

Illustrative examples of the imide derivative include phthalimide, succinimide, and maleimide.

Illustrative examples of the compound shown by the general formula (20) include tris[2-(methoxymethoxy)ethyl] amine, tris[2-(2-methoxyethoxy)ethyl]amine, tris[2-(2-methoxyethoxymethoxy)ethyl]amine, tris[2-(1-methoxyethoxy)ethyl]amine, tris[2-(1-ethoxyethoxy)ethyl]amine, tris[2-(2-ethoxypropoxy)ethyl]amine, tris[2-{2-(2-hydroxyethoxy)ethoxy}ethyl]amine, 4,7,13,16,21,24-hexaoxa-1,10-diazabicyclo[8.8.8]hexacosane 4,7,13,18-tetraoxa-1,10-diazabicyclo[8.5.5]eicosane 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl) amine, tris(2-valeryloxyethyl)amine, tris(2-pivaloyloxyethyl)amine, N,N-bis(2-acetoxyethyl) 2-(acetoxyacetoxy) ethyl amine, tris(2-methoxycarbonyloxyethyl)amine, tris(2-tert-butoxycarbonyloxyethyl)amine, tris[2-(2-oxopropoxy) ethyl]amine, tris[2-(methoxycarbonylmethyl)oxyethyl] amine, tris[2-(tert-butoxycarbonylmethyloxy)ethyl]amine, tris[2-(cyclohexyloxycarbonylmethyloxy)ethyl]amine, tris (2-methoxycarbonylethyl)amine, tris(2-ethoxycarbonylethyl)amine, N,N-bis(2-hydroxyethyl) 2-(methoxycarbonyl) ethyl amine, N,N-bis(2-acetoxyethyl) 2-(methoxycarbonyl) ethyl amine, N,N-bis(2-hydroxyethyl) 2-(ethoxycarbonyl) ethyl amine, N,N-bis(2-acetoxyethyl) 2-(ethoxycarbonyl) ethyl amine, N,N-bis(2-hydroxyethyl) 2-(2-methoxyethoxycarbonyl)ethyl amine, N,N-bis(2-acetoxyethyl) 2-(2-methoxyethoxycarbonyl)ethyl amine, N,N-bis(2-hydroxyethyl) 2-(2-hydroxyethoxycarbonyl) ethyl amine, N,N-bis(2-acetoxyethyl) 2-(2-acetoxyethoxycarbonyl)ethyl amine, N,N-bis(2-hydroxyethyl) 2-[(methoxycarbonyl)methoxycarbonyl]ethyl amine, N,N-bis(2-acetoxyethyl) 2-[(methoxycarbonyl)methoxycarbonyl]ethyl amine, N,N-bis(2-hydroxyethyl) 2-(2-oxopropoxycarbonyl)ethyl amine, N,N-bis(2-acetoxyethyl) 2-(2-oxopropoxycarbonyl)ethyl amine, N,N-bis(2-hydroxyethyl) 2-(tetrahydrofurfuryloxycarbonyl)ethyl amine, N,N-bis(2-acetoxyethyl) 2-(tetrahydrofurfuryloxycarbonyl)ethyl amine, N,N-bis(2-hydroxyethyl) 2-[(2-oxotetrahydrofuran-3-yl)oxycarbonyl]ethyl amine, N,N-bis(2-acetoxyethyl) 2-[(2-oxotetrahydraofuran-3-yl)oxycarbonyl]ethyl amine, N,N-bis(2-hydroxyethyl) 2-(4-hydroxybutoxycarbonyl) ethyl amine, N,N-bis(2-formyloxyethyl) 2-(4-formyloxybutoxycarbonyl)ethyl amine, N,N-bis(2-formyloxyethyl) 2-(2-formyloxyethoxycarbonyl)ethyl amine, N,N-bis(2-methoxyethyl) 2-(methoxycarbonyl)ethyl amine, N-(2-hydroxyethyl)bis[2-(methoxycarbonyl)ethyl]amine, N-(2-acetoxyethyl)bis[2-(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis[2-(methoxycarbonyl)ethyl]amine, N-(3-acetoxy-1-propyl)bis[2-(methoxycarbonyl)ethyl] amine, N-(2-methoxyethyl)bis[2-(methoxycarbonyl)ethyl] amine, N-butyl bis[2-(methoxycarbonyl)ethyl]amine, N-butyl bis[2-(2-methoxyethoxycarbonyl)ethyl]amine, N-methyl bis(2-acetoxyethyl)amine, N-ethyl bis(2-acetoxyethyl) amine, N-methyl bis(2-pivaloyloxyethyl)amine, N-ethyl bis [2-(methoxycarbonyloxy)ethyl]amine, N-ethyl bis[2-(tert-butoxycarbonyloxy)ethyl]amine, tris (methoxycarbonylmethyl)amine, tris (ethoxycarbonylmethyl)amine, N-butyl bis (methoxycarbonylmethyl)amine, N-hexyl bis (methoxycarbonylmethyl)amine, and β-(diethylamino)-δ-valerolactone; however, the compound is not restricted to them.

The above-mentioned basic compounds may be used solely or as a mixture of two or more kinds.

In view of sensitivity, the amount of the basic compound to be blended is preferably in the range of 0 to 3 parts by mass, particularly preferably 0.01 to 1 part by mass based on 100 parts by mass of (A) the silicone skeleton-containing polymer compound.

In addition to the components (A) to (E) as mentioned above, other additives may be added to the chemically amplified negative resist composition of the present invention. The additives may be exemplified by a surfactant which is commonly used to enhance coating properties, a light absorber which is commonly used to enhance light absorption of the photosensitive acid generator or the like, and so forth.

As the surfactant, nonionic type surfactants such as fluorinated surfactants are preferred, and illustrative examples thereof include perfluoroalkyl polyoxyethylene ethanol, fluorinated alkyl ester, perfluoroalkylamine oxide, and a fluorine-containing organosiloxane compound.

These surfactants may be commercially available products, and illustrative examples thereof include Flolade "FC-4430" (available from Sumitomo 3M Ltd.), Surflon "S-141" and "S-145" (both are available from Asahi Glass Co., Ltd.), Unidyne "DS-401", "DS-4031", and "DS-451" (all are available from Daikin Industries, Ltd.), Megafac "F-8151" (available from DIC Co.), and "X-70-093" (available from Shin-Etsu Chemical Co., Ltd.). Among them, Flolade "FC-4430" (available from Sumitomo 3M Ltd.) and "X-70-093" (available from Shin-Etsu Chemical Co., Ltd.) are preferred.

Illustrative examples of the light absorber include diarylsulfoxide, diarylsulfone, 9,10-dimethylanthracene, and 9-fluorenone.

The chemically amplified negative resist composition of the present invention may be prepared by a usual method. After the above-mentioned respective components are mixed by stirring, the resulting mixture is filtrated through a filter or the like to prepare the chemically amplified negative resist composition. Also, a later-described photocurable dry film may be prepared similarly by using this chemically amplified negative resist composition.

The patterning using the chemically amplified negative resist composition of the present invention thus prepared may be performed by a well-known lithography technology. For example, the chemically amplified negative resist composition is applied by a spin coating method onto a silicon wafer, a $SiO_2$ Substrate, a SiN substrate, or a substrate formed with a pattern of a copper wiring or the like, and then, it is prebaked at 80 to 130° C. for 50 to 600 seconds approximately to form a resist film having a thickness of 1 to 50 μm, preferably 1 to 30 μm, more preferably 5 to 20 μm.

In the spin coating method, after about 5 mL of the resist composition is dispensed on a silicon substrate, the substrate is rotated, whereby the resist composition may be applied onto the substrate. By adjusting the rotation speed during this operation, film thickness of the resist film on the substrate can be readily controlled.

Next, a mask to form the intended pattern is put over the resist film, and then, a high energy beam having wavelength of 190 to 500 nm such as i-beam and g-beam is irradiated thereto with an exposure dose of about 1 to 5,000 $mJ/cm^2$, preferably about 100 to 2,000 $mJ/cm^2$. By this exposure, the exposed part is crosslinked to form a pattern not soluble in a developer (this will be mentioned later).

Then, if necessary, post-exposure bake (PEB) may be carried out on a hot plate at a temperature of 60 to 150° C. for a time of 1 to 10 minutes, preferably at 80 to 120° C. for 1 to 5 minutes.

Thereafter, development is carried out by using a developer. As to the developer, a 2.38% TMAH aqueous solution and the above-mentioned solvent that is used for preparing the chemically amplified negative resist composition of the present invention may be used. Preferable examples thereof include alcohols such as isopropyl alcohol (IPA), ketones such as cyclohexanone, and glycols such as propylene glycol monomethyl ether. The development can be carried out by a usual method, for example, by soaking the substrate formed with a pattern into a developer. Then, if necessary, washing, rinsing, drying, and so forth may be performed to obtain a resist film having an intended pattern. Meanwhile, in the case that patterning is not necessary, for example, in the case that a uniform film is merely wanted, the same procedure as the above-mentioned patterning process except using no photomask may be employed.

The obtained pattern in the resist film is preferably post-cured by using an oven or a hot plate at a temperature ranging from 100 to 250° C., preferably from 150 to 220° C., more preferably from 170 to 190° C. If the post-cure temperature is from 100 to 250° C., the crosslinking density of the resist film is increased, and remaining volatile components can be removed. Thus, this temperature range is preferable in view of adhesiveness to a substrate, heat resistance, strength, and electronic characteristics. The time for the post-cure can be from 10 minutes to 10 hours.

The cured film thus obtained has excellent flexibility, adhesiveness to a substrate, heat resistance, electric characteristics, mechanical strength, and chemical resistance to a soldering flux liquid, and thus, a semiconductor device having the cured film like this as a top coat has superior reliability, and especially, generation of a crack during a thermal cycle test can be prevented. In other words, the chemically amplified negative resist composition of the present invention can provide a top coat suitable to protect electric and electronic parts, a semiconductor device, and the like.

Further, the present invention provides a photo-curable dry film produced by using the above-mentioned chemically amplified negative resist composition.

First, the structure of the photo-curable dry film of the present invention will be described. The photo-curable dry film has a structure that a photo-curable resin layer is sandwiched between a supporting film and a top coat film. For the photo-curable resin layer, the chemically amplified negative resist composition of the present invention, which is effective to form a top coat to protect electric and electronic parts, may be used. Such a photo-curable dry film can form a fine pattern in wide ranges of film thickness and wavelength, and can be post-cured at low temperature to give a top coat having excellent flexibility, heat resistance, electric characteristics, adhesiveness, reliability, and chemical resistance.

In the present invention, the photo-curable resin layer of the photo-curable dry film obtained from the above-mentioned chemically amplified negative resist composition is a solid, so that the photo-curable resin layer does not contain a solvent. Therefore, there is no fear that bubbles due to the evaporation remain inside the photo-curable resin layer as well as between the photo-curable resin layer and the substrate having concavity and convexity.

The interlayer insulating film is tending to become thinner as a semiconductor device progresses toward downsizing, thinning, and layer-increasing; however, in view of planarity and step coverage of the substrate having concavity and convexity, there is preferable range of the film thickness. That is, the film thickness of the photo-curable resin layer is preferably in the range of 10 to 100 μm, more preferably 10 to 70 μm, particularly preferably 10 to 50 μm.

In the photo-curable resin layer, viscosity and fluidity are closely interrelated. Thus, the photo-curable resin layer can express appropriate fluidity in the appropriate range of viscosity, and it can penetrate deep into a narrow space. Accordingly, when the photo-curable dry film having the photo-curable resin layer formed of the chemically amplified negative resist composition containing the silicone skeleton-containing polymer compound of the present invention with an appropriate viscosity as mentioned above adheres- to a substrate having concavity and convexity, the photo-curable resin layer can cover the substrate in accordance with the concavity and the convexity, thereby achieving a high flatness. Moreover, the silicone skeleton-containing polymer compound, which is a main component of the photo-curable resin layer, contains a siloxane chain; and because of this, the surface tension thereof is so low that a higher flatness may be achievable. In addition, if the photo-curable resin layer adheres to the substrate under a vacuum environment, generation of a void therebetween can be more effectively prevented.

Next, the method for producing the photo-curable dry film of the present invention will be described.

In the photo-curable dry film of the present invention, the chemically amplified negative resist composition used for forming the photo-curable resin layer is obtained by mixing the components with stirring, followed by filtration through a filter or the like, as mentioned above. This chemically amplified negative resist composition can be used as a material for forming the photo-curable resin layer.

The supporting film used in the photo-curable dry film of the present invention may be a monolayer or a multilayer film having plural polymer films being laminated. The material thereof may be exemplified by a synthetic resin film such as polyethylene, polypropylene, polycarbonate, and polyethylene terephthalate, etc. Among these, polyethylene terephthalate is preferable because it has appropriate flexibility, mechanical strength, and heat resistance. These films may be variously subjected to, for example, corona treatment and coating treatment with a releasing agent. For this, many commercial films may be used. Illustrative examples thereof include Cerapeel WZ (RX) and Cerapeel BX8 (R) (both are available from Toray Advanced Film Co., Ltd.), E7302 and E7304 (both are available from Toyobo Co., Ltd.), Purex G31 and Purex G71T1 (both are available from Teijin DuPont Films Japan Ltd.), and PET38×1-A3, PET38×1-V8, and PET38×1-X08 (all available from Nippa Co., Ltd.).

The top coat film used in the photo-curable dry film of the present invention may be the same film as the above-mentioned supporting film, but polyethylene terephthalate and polyethylene having appropriate flexibility are preferred. For this, commercial films may be used, and illustrative examples thereof include, besides the polyethylene terephthalates that have already been mentioned, polyethylene such as GF-8 (available from Tamapoly Co., Ltd.) and PE Film 0-Type (available from Nippa Co., Ltd.).

The thicknesses of the supporting film and the top coat film are preferably both in the range of 10 to 100 μm, particularly preferably 25 to 50 μm, in view of stable production of the photo-curable dry film and the rolling habit around a roll axis, so-called curl-prevention.

As to the manufacturing equipment for the photo-curable dry film, a film coater that is generally used for producing an adhesive product may be used. Illustrative examples of the film coater include a comma coater, a comma reverse coater, a multi coater, a die coater, a lip coater, a lip reverse coater, a direct gravure coater, an offset gravure coater, a 3-roll bottom reverse coater, and a 4-roll bottom reverse coater.

The supporting film is rolled-out from a roll-out axis of the film coater; and the chemically amplified negative resist composition is applied onto the supporting film with a prescribed thickness to form the photo-curable resin layer while it is passing through a coater head of the film coater; and then, after it is passed through a hot-air circulating oven at a prescribed temperature for a prescribed period, the photo-curable resin layer that has been continuously dried on the supporting film is passed through a laminate roll together with the top coat film that has been rolled-out from another roll-out axis of the film coater under a prescribed pressure, thereby bonding the top coat film to the photo-curable resin layer on the supporting film, followed by roll-up to a roll-up axis of the film coater. In this case, temperature of the hot-air circulating oven is preferably in the range of 25 to 150° C., the period for passing through it is preferably in the range of 1 to 100 minutes, and the laminate roll pressure is preferably in the range of 0.01 to 5 MPa.

Next, the patterning process using the photo-curable dry film that is obtained in the way as mentioned above will be described.

In the patterning process using the photo-curable dry film of the present invention, first, the top coat film is delaminated from the photo-curable dry film to bring the photo-curable resin layer into close contact with the substrate. Then, photo exposure is performed, followed by post-exposure bake (hereinafter, PEB). Subsequently, development is performed, and if necessary, post-curing is carried out, whereby a cured film formed with a pattern can be obtained.

First, the photo-curable dry film is brought into close contact with a substrate by using a film adhering equipment. The substrate may be exemplified by a silicon wafer, a silicon wafer for TSV, a circuit substrate made of plastics, ceramics, various metals, etc., and especially, the substrate having a trech or a hole with an aperture width of 10 to 100 μm and a depth of 10 to 120 μm may be mentioned. As to the film adhering equipment, a vacuum laminator is preferred.

Specifically, the photo-curable dry film is attached to a film adhering equipment, the top coat film of the photo-curable dry film is delaminated, and the photo-curable resin layer thereby exposed is brought into close contact with a substrate on a table at a prescribed temperature by using an adhering roll under a prescribed pressure in a vacuum chamber with a prescribed degree of vacuum. Meanwhile, temperature of the table is preferably in the range of 60 to 120° C., pressure of the adhering roll is preferably in the range of 0 to 5.0 MPa, and degree of vacuum in the vacuum chamber is preferably in the range of 50 to 500 Pa.

After close contact, patterning may be performed by using a well-known lithography technology. At this time, in order to effectively carry out the photo-curing reaction of the photo-curable resin layer as well as to enhance the adhesiveness between the photo-curable resin layer and the substrate, pre-bake may be carried out if necessary. The pre-bake may be carried out, for example, at 40 to 140° C. for 1 minute to 1 hour approximately.

Then, curing is carried out by exposure to a light having a wavelength of 190 to 500 nm via a photomask under the state of intervention of the supporting film or under the state of the supporting film delaminated. The photomask may be obtained by engraving a prescribed pattern. Meanwhile, the photomask is preferably made of a material that can shield the light having a wavelength of 190 to 500 nm. For example, chromium and the like are preferably used, but it is not limited thereto.

As to the light having a wavelength of 190 to 500 nm, lights having various wavelengths generated from, for example, a radiation-beam generating instrument may be used, and illustrative examples thereof include UV light such as g-beam and i-beam, and far ultraviolet light (248 nm and 193 nm). The wavelength is preferably in the range of 248 to 436 nm. The exposure dose is preferably, for example, in the range of 10 to 3,000 mJ/cm$^2$. By subjecting to the exposure as mentioned above, the exposed part is crosslinked to form the pattern not soluble in the developer (this will be mentioned later).

Then, post-exposure baking (PEB) is carried out to enhance the development sensitivity. The post-exposure baking may be performed, for example, at 40 to 140° C. for 0.5 to 10 minutes.

Thereafter, development is carried out by using a developer. As to the developer, a 2.38% TMAH aqueous solution and the above-mentioned solvent that is used for preparing the chemically amplified negative resist composition used for forming the photo-curable resin layer of the photo-curable dry film of the present invention may be used. Preferable examples thereof include alcohols such as isopropyl alcohol (IPA), ketones such as cyclohexanone, and glycols such as propylene glycol monomethyl ether. The development can be carried out by a usual method, for example, by soaking the substrate formed with a pattern into a developer. Then, if necessary, washing, rinsing, drying, and so forth may be performed to obtain a film of the photo-curable resin layer having an intended pattern. Meanwhile, in the case that patterning is not necessary, for example, in the case that a uniform film is merely wanted, the same procedure as the above-mentioned patterning process except using no photomask may be employed.

The obtained pattern may be post-cured by using an oven or a hot plate at a temperature ranging from 100 to 250° C., preferably from 150 to 220° C., more preferably from 170 to 190° C. If the post-cure temperature is from 100 to 250° C., the crosslinking density of the film of the photo-curable resin layer is increased, and remaining volatile components can be removed. Thus, this temperature range is preferable in view of adhesiveness to a substrate, heat resistance, strength, and electronic characteristics. The time for the post-cure can be from 10 minutes to 10 hours.

The cured film thus obtained has excellent flexibility, adhesiveness to a substrate, heat resistance, electric characteristics, mechanical strength, and chemical resistance to a soldering flux liquid; and thus, a semiconductor device having the cured film like this as a top coat has superior reliability, and especially, generation of a crack during a thermal cycle test can be prevented. In other words, the photo-curable dry film of the present invention can provide a top coat suitable to protect electric and electronic parts, a semiconductor device, and the like.

In this way, the photo-curable dry film of the present invention can be effectively applied to the substrate having a trench or a hole. Thus, the present invention provides a layered product which has a substrate including a trench and/or a hole each having an aperture width of 10 to 100 μm and a depth of 10 to 120 μm, and a cured layer of the photo-curable resin formed of the photo-curable dry film laminated on the substrate.

As mentioned above, the chemically amplified negative resist composition of the present invention and the photo-curable dry film produced by using this composition can give a top coat having excellent flexibility, adhesiveness to a substrate, heat resistance, electric characteristics, mechanical strength, and chemical resistance by curing themselves. Thus, these are useful to an insulating film for a semiconductor device including a rewiring use, an insulating film for a multilayer printed substrate, a solder mask, a cover lay film, and an insulating film for embedding a through-silicon via (TSV) as well as useful for bonding to a substrate.

EXAMPLES

Hereinafter, the present invention is explained in more detail by referring to Synthesis Examples and Examples, but the present invention is not limited to the following examples. Meanwhile, in the following examples, the term "parts" indicates parts by mass.

I. Preparation of Chemically Amplified Negative Resist Composition

The structures of compounds (M-1) to (M-12) used in Synthesis Examples are shown below.

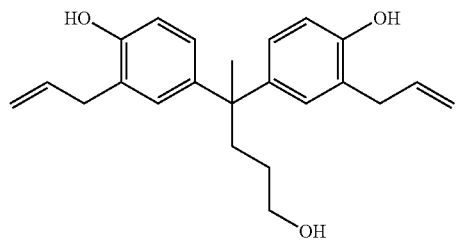
(M-1)

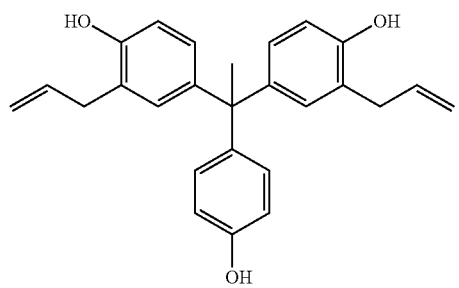
(M-2)

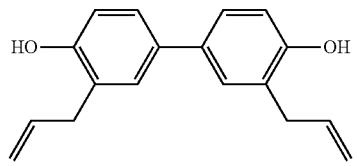
(M-3)

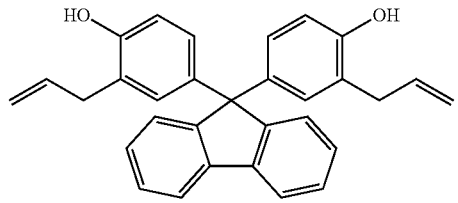
(M-4)

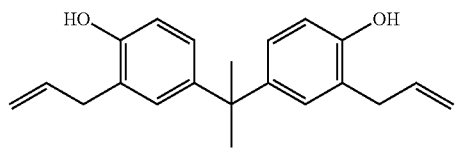
(M-5)

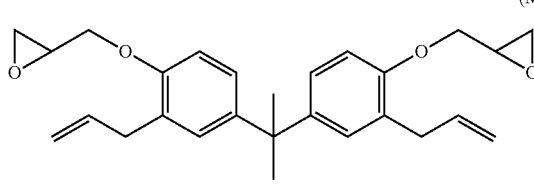
(M-6)

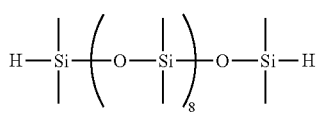
(M-7)

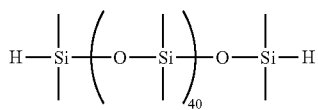
(M-8)

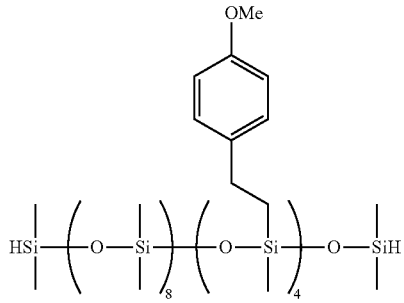
(M-9)

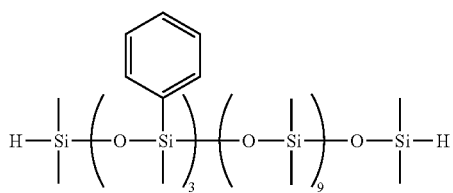
(M-10)

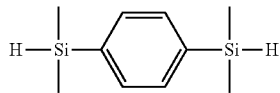
(M-11)

(M-12)

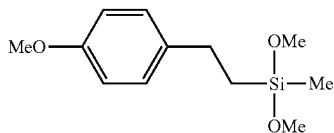

The silicone skeleton-containing polymer compound having a repeating unit shown by the general formula (1) and the silicone skeleton-containing polymer compound having a repeating unit shown by the general formula (24) of the present invention are shown below, (1)

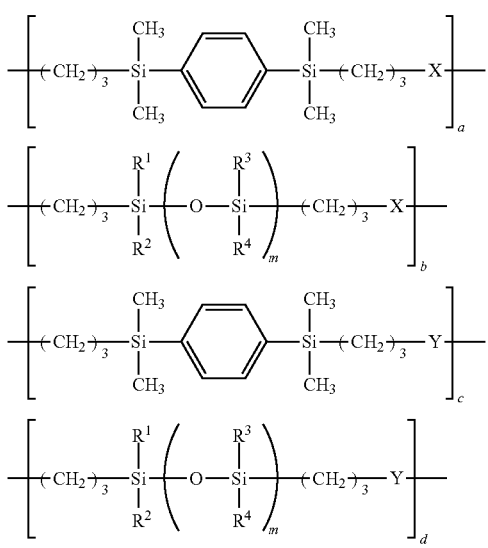

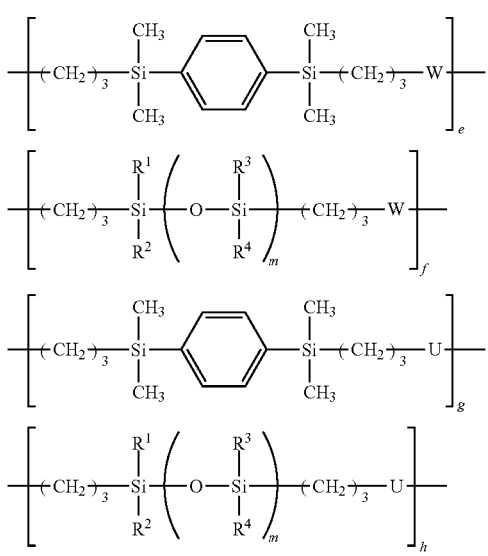

wherein $R^1$ to $R^4$, "a", "b", "c", "d", "e", "f", "g", "h", "m", X, Y, W, and U each are as defined above, (24)

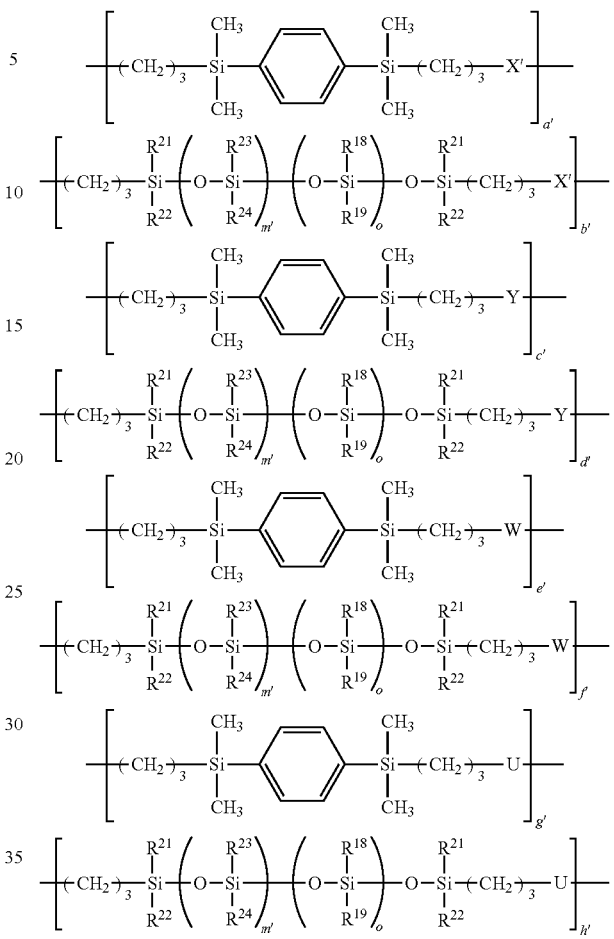

wherein $R^{21}$ to $R^{24}$, $R^{18}$, $R^{19}$, a', b', c', e', f', g', h', m', o, X', Y, W, and U each are as defined above.

[Synthesis Example 1] Synthesis of 4,4'-bis(4-hydroxy-3-allylphenyl)pentanol (M-1)

A 5-L flask equipped with a stirrer, thermometer, and nitrogen purge system was charged with 458 g of diphenolic acid, 884 g of potassium carbonate, and 2000 g of dimethylacetoamide. Then, 774 g of allylbromide was added dropwise thereto while stirring at room temperature under nitrogen atmosphere, followed by further stirring at 60° C. for 58 hours. To the resulting mixture was added dropwise 221 g of potassium carbonate, 193 g of allylbromide, and 500 g of dimethylacetamide while maintaining the temperature, and the mixture was further stirred at 60° C. for 20 hours. After 2000 g of water was added dropwise under ice-cooling to terminate the reaction, 1000 g of toluene, 1000 g of hexane, 2000 g of water were added, and the organic layer was collected. The obtained organic layer was successively washed with 2000 g of water, 500 g of water four times, and 500 g of saturated saline, and the solvent was distilled off to obtain 686 g of a crude material of allyl 4,4-bis(4-allyloxyphenyl)-pentanoate.

A 5-L flask equipped with a stirrer, thermometer, and nitrogen purge system under nitrogen atmosphere was charged with 655 g of the allyl 4,4-bis(4-allyloxy-phenyl) pentanoate and 1310 g of tetrahydrofuran to make a solution.

Then, 605 g of sodium bis(2-methoxyethoxy)aluminum hydride (70% by mass of toluene solution) was added dropwise thereto under ice-cooling. After stirring at room temperature for 3 hours, 1526 g of 10% by mass hydrochloric acid was added dropwise under ice-cooling to terminate the reaction. To the reaction solution was added 250 g of ethyl acetate and 750 g of toluene, and the organic layer was collected and washed 3 times with 500 g of water. The solvent of the obtained organic layer was distilled off, and the remainder was dissolved in 1000 g of toluene, and washed with 300 g of 4% by mass aqueous sodium hydroxide solution 5 times, 330 g of 2% by mass hydrochloric acid, and then 300 g of water 4 times. Thereafter, the solvent of the obtained organic layer was distilled off to obtain 555 g of a crude material of 4,4-bis(4-allyloxyphenyl)pentanol.

Then, a 5-L flask equipped with a stirrer, thermometer, and nitrogen purge system under nitrogen atmosphere was charged with 500 g of the 4,4-bis(4-allyloxyphenyl)pentanol and 500 g of N,N-diethylaniline to make a solution, and the solution was heated at 180° C. and stirred for 18 hours. After cooled to room temperature, 1460 g of 10% by mass hydrochloric acid was added dropwise under ice-cooling, and 2400 g of ethyl acetate was added to the reaction mixture. Then, the organic layer was collected and washed 4 times with 2400 g of water. The solvent of the obtained organic layer was distilled off, and the remainder was dissolved in 500 g of ethyl acetate, and 2000 g of hexane was added dropwise thereto under stirring. Thereafter, the hexane layer was removed, and the remaining oily material was dissolved in 500 g of ethyl acetate and collected. Then, the solvent of the obtained organic layer was distilled off, whereby 466 g of 4,4'-bis(4-hydroxy-3-allylphenyl)pentanol (M-1) was obtained with a yield of 93%. Incidentally, the compound (M-1) was identified by $^1$H-NMR (600 MHz) (JEOL-600 spectrometer manufactured by JEOL, Ltd.).

[Synthesis Example 2] Synthesis of bis(4-hydroxy-3-allylphenyl)-(4-hydroxyphenyl)-methane (M-2)

A 3-necked 1-L flask inside which was replaced with nitrogen was charged with 50.0 g (409 mmol) of 4-hydroxybenzaldehyde and 330.0 g (2,457 mmol) of 2-allylphenol. The mixture was stirred at room temperature to dissolve the 4-hydroxybenzaldehyde, and transferred to an ice bath. Then, 7.9 g of methanesulfonic acid was added dropwise slowly while maintaining the reaction solution at 10° C. or lower. After dropwise addition, the reaction solution was aged for 10 hours at room temperature, and 400 g of toluene and 400 g of saturated sodium hydrogen carbonate in aqueous solution were added thereto, and this mixture was transferred to a 2-L separatory funnel. The aqueous layer was removed therefrom, and 400 g of saturated sodium hydrogen carbonate in aqueous solution was added thereto for liquid separation followed by water-washing with 400 g of ultrapure water twice. After the collected organic layer was crystallized by 4400 g of hexane, supernatant was removed, and the remainder was dissolved in 300 g of toluene to crystallize again by 2000 g of hexane. This procedure was repeated once again, and the precipitated crystal was collected by filtration and dried, whereby 95 g of bis(4-hydroxy-3-allylphenyl)-(4-hydroxyphenyl)-methane (M-2) was obtained with a yield of 58%. Incidentally, the compound (M-2) was identified by $^1$H-NMR (600 MHz) (JEOL-600 spectrometer manufactured by JEOL, Ltd.).

[Synthesis Example 3] Synthesis of 3,3'-diallyl-4,4'-dihydroxy-1,1'-biphenyl (M-3)

A 4-necked 3-L flask equipped with a stirrer, thermometer, and nitrogen purge system was charged with 300 g of 4,4'-biphenol, 534 g of potassium carbonate, and 1200 g of acetone. Then, 468 g of allylbromide was added dropwise thereto while stirring at room temperature under nitrogen atmosphere, followed by further stirring at 50° C. for 24 hours. After cooled to room temperature, 1200 g of water was added thereto to terminate the reaction, and the precipitated crystal was collected by filtration. Further, the obtained crystal was washed with 1200 g of water 3 times, and the solvent was then distilled off to obtain 429 g of a crude material of 4,4'-bis(allyloxy)-1,1'-biphenyl.

Then, 3-L flask equipped with a stirrer, thermometer, and nitrogen purge system under nitrogen atmosphere was charged with 429 g of the 4,4'-bis(allyloxy)-1,1'-biphenyl and 858 g of N,N-diethylaniline to make a solution, and the solution was heated at 180° C. and stirred for 24 hours. After cooled to room temperature, 2300 g of 10% by mass hydrochloric acid was added dropwise under ice-cooling, and 1500 g of ethyl acetate was added to the reaction mixture. Then, the organic layer was collected and washed 5 times with 1500 g of water. The solvent of the obtained organic layer was distilled off and instead, 93 g of ethyl acetate and 2800 g of hexane were added thereto. The resulting solution was stirred at room temperature for a while to precipitate a crystal, and the crystal was collected by filtration. Thereafter, the crystal was washed twice with 1000 g of hexane, whereby 370 g of 3,3'-diallyl-4,4'-dihydroxy-1,1'-biphenyl (M-3) was obtained with a two-step yield of 86%. Incidentally, the compound (M-3) was identified by $^1$H-NMR (600 MHz) (JEOL-600 spectrometer manufactured by JEOL, Ltd.).

[Synthesis Example 4] Synthesis of Compound (M-12)

A 3-necked 1-L flask equipped with a stirrer, thermometer, and nitrogen purge system was charged with 348 g (3.28 mol) of dimethoxymethylsilane and 2.1 g of toluene solution containing chloroplatinic acid (5% by mass), followed by heating at 60° C. Then, 400 g (2.98 mol) of 4-methoxystyrene was added dropwise thereto over 7 hours. At this time, the heating temperature was increased up to 100° C. as the reaction system temperature rose. After dropwise addition, the mixture was cooled to room temperature, and purified by distillation to obtain 583 g of compound (M-12) with a yield of 81.4%. Incidentally, the compound (M-12) was identified by $^1$H-NMR (600 MHz) (JEOL-600 spectrometer manufactured by JEOL, Ltd.).

[Synthesis Example 5] Synthesis of Compound (M-9)

A 3-necked 1-L flask was charged with 212 g of the compound (M-12); and 162 g of 7.5% by mass aqueous potassium hydroxide solution was added thereto under stirring at room temperature. After addition, the mixture was heated at 100° C. while removing generated methanol from the system, and aged for 6 hours. Then, the mixture was cooled to room temperature, and 200 g of toluene and 68 g of 10% by mass hydrochloric acid were added. This mixture was transferred to a 1-L separatory funnel, and the lower aqueous layer was removed. Further, liquid separation and water-washing was repeated 3 times with 50 g of ultrapure water, and the organic layer was concentrated under reduced pressure to obtain 166 g of hydrolysis condensate of the compound (M-12).

A 3-necked 1-L flask inside which was replaced with nitrogen was charged with 164 g of the obtained hydrolysis condensate (0.84 mol when assuming that one condensation unit corresponds to its molecular weight), 125 g of cyclic tetramer of dimethylsiloxane (1.69 mol when assuming that one condensation unit corresponds to its molecular weight), and 37.4 g (0.28 mol) of 1,1,3,3-tetramethyldisiloxane; and the mixture was stirred at room temperature. Then, 1.5 g of trifluoromethanesulfonic acid was added dropwise thereto under stirring, and after dropwise addition, the mixture was heated at 60° C., and aged for 3 hours. The mixture was then cooled to room temperature, and 300 g of toluene and 208 g of 4% by mass aqueous sodium hydrogencarbonate solution were added thereto, followed by stirring for 1 hour. This mixture was transferred to a 1-L separatory funnel, and the lower aqueous layer was removed. Further, liquid separation and water-washing was repeated twice with 200 g of ultra-pure water, and the organic layer was concentrated under reduced pressure to obtain compound (M-9). Incidentally, the compound (M-9) was identified by $^1$H-NMR (600 MHz) (JEOL-600 spectrometer manufactured by JEOL, Ltd.).

[Synthesis Example 6] Synthesis of Silicone Skeleton-Containing Polymer Compound (A-1)

A 3-L flask equipped with a stirrer, thermometer, nitrogen purge system, and reflux condenser was charged with 350 g of toluene and 120 g of compound (M-1) to make a solution. To the solution were added 39 g of compound (M-3) and 85 g of compound (M-7), and the resulting mixture was heated at 60° C. Thereafter, 1.1 g of carbon carried platinum catalyst (5% by mass) was added thereto, and the mixture was heated at 90° C. and aged for 3 hours. Then, the mixture was cooled to 60° C., 1.1 g of carbon carried platinum catalyst (5% by mass) was added again, and 62 g of compound (M-11) was dropped into the flask over 30 minutes. At this time, the temperature inside the flask was increased to 65 to 67° C. After dropwise addition, the mixture was further aged at 90° C. for 3 hours, and cooled to room temperature. Then, 780 g of methyl isobutyl ketone was added to the reaction solution, and this reaction solution was filtrated under pressure through a filter to remove the platinum catalyst. Further, to the obtained solution containing a silicone skeleton-containing polymer compound was added 780 g of pure water, and the mixture was stirred, allowed to stand, and separated to remove the lower aqueous layer. This liquid separation and water-washing operation was repeated 6 times to remove trace amounts of acid component in the silicone skeleton-containing polymer compound. The solvent in the resulting silicone skeleton-containing polymer compound solution was distilled off under reduced pressure and instead, 750 g of tetrahydrofuran was added thereto, and the tetrahydrofuran solution was concentrated under reduced pressure so as to have a solid concentration of 30% by mass.

Then, a 3-L flask equipped with a stirrer, thermometer, nitrogen purge system, and reflux condenser was charged with 1000 g of the above-mentioned tetrahydrofuran solution containing 30% by mass of the silicone skeleton-containing polymer compound; and 31 g of succinic anhydride and 32 g of triethylamine were added thereto, followed by heating at 50° C. After stirring for 2 hours, the mixture was cooled to room temperature, and 900 g of saturated aqueous ammonium chloride solution and 1500 g of ethyl acetate were added thereto to terminate the reaction. Then, the aqueous layer was removed, and liquid separation and water-washing was repeated 5 times with 900 g of ultrapure water. The solvent of the collected organic layer was distilled off and instead, 600 g of cyclopentanone was added thereto, and the resulting cyclopentanone solution was concentrated under reduced pressure so as to have a solid concentration of 40 to 50% by mass, thereby obtaining a solution containing a silicone skeleton-containing polymer compound having carboxylic acid (A-1) and cyclopentanone as the main solvent. The molecular weight of the silicone skeleton-containing polymer compound in this solution was measured by GPC, consequently finding a weight average molecular weight of 10,000 in terms of polystyrene. The polymer compound corresponds to the general formula (24) wherein a'=0.220, b'=0.080, c'=0, d'=0, e'=0, f'=0, g'=0.513, h'=0.187, and X' and U are as follows.

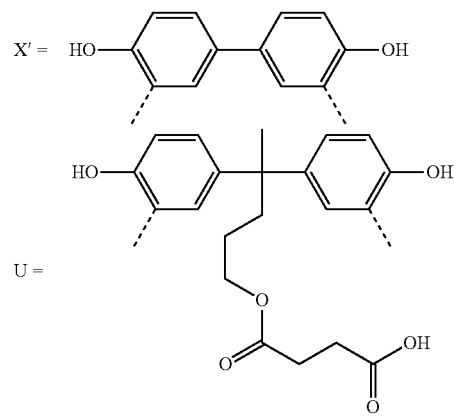

[Synthesis Example 7] Synthesis of Silicone Skeleton-Containing Polymer Compound (A-2)

A 3-L flask equipped with a stirrer, thermometer, nitrogen purge system, and reflux condenser was charged with 497 g of toluene and 120 g of compound (M-1) to make a solution. To the solution were added 91 g of compound (M-3) and 119 g of compound (M-7), and the resulting mixture was heated at 60° C. Thereafter, 1.6 g of carbon carried platinum catalyst (5% by mass) was added thereto, and the mixture was heated at 90° C. and aged for 3 hours. Then, the mixture was cooled to 60° C., 1.6 g of carbon carried platinum catalyst (5% by mass) was added again, and 87 g of compound (M-11) was dropped into the flask over 30 minutes. At this time, the temperature inside the flask was increased to 65 to 67° C. After dropwise addition, the mixture was further aged at 90° C. for 3 hours, and cooled to room temperature. Then, 780 g of methyl isobutyl ketone was added to the reaction solution, and this reaction solution was filtrated under pressure through a filter to remove the platinum catalyst. Further, to the obtained solution containing a silicone skeleton-containing polymer compound was added 780 g of pure water, and the mixture was stirred, allowed to stand, and separated to remove the lower aqueous layer. This liquid separation and water-washing operation was repeated 6 times to remove trace amounts of acid component in the silicone skeleton-containing polymer compound. The solvent in the resulting silicone skeleton-containing polymer compound solution was distilled off under reduced pressure and instead, 1078 g of tetrahydrofuran was added thereto, and the tetrahydrofuran solution was concentrated under reduced pressure so as to have a solid concentration of 30% by mass.

Then, a 3-L flask equipped with a stirrer, thermometer, nitrogen purge system, and reflux condenser was charged with 1400 g of the above-mentioned tetrahydrofuran solution containing 30% by mass of the silicone skeleton-containing polymer compound; and 31 g of succinic anhydride and 32 g of triethylamine were added thereto, followed by heating at 50° C. After stirring for 2 hours, the mixture was cooled to room temperature, and 900 g of saturated aqueous ammonium chloride solution and 1500 g of ethyl acetate were added thereto to terminate the reaction. Then, the aqueous layer was removed, and liquid separation and water-washing was repeated 5 times with 900 g of ultrapure water. The solvent of the collected organic layer was distilled off and instead, 600 g of cyclopentanone was added thereto, and the resulting cyclopentanone solution was concentrated under reduced pressure so as to have a solid concentration of 40 to 50% by mass, thereby obtaining a solution containing a silicone skeleton-containing polymer compound having carboxylic acid (A-2) and cyclopentanone as the main solvent. The molecular weight of the silicone skeleton-containing polymer compound in this solution was measured by GPC, consequently finding a weight average molecular weight of 13,000 in terms of polystyrene. The polymer compound corresponds to the general formula (24) wherein a'=0.367, b'=0.133, c'=0, d'=0, e'=0, f'=0, g'=0.367, h'=0.133, and X' and U are as follows.

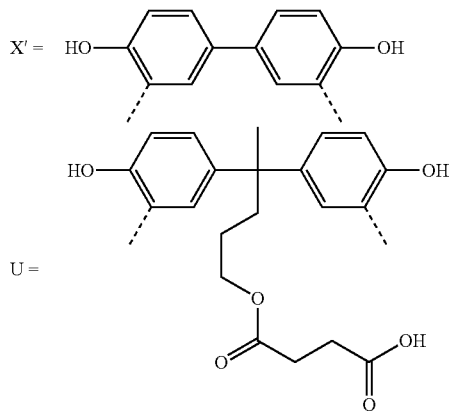

[Synthesis Example 8] Synthesis of Silicone Skeleton-Containing Polymer Compound (A-3)

A silicone skeleton-containing polymer compound was synthesized in the same manner as in Synthesis Example 6 except that 362 g of compound (M-8) was used in place of 85 g of compound (M-7), and cyclopentanone was added thereto as the main solvent to obtain a solution containing the silicone skeleton-containing polymer compound (A-3). The molecular weight of the silicone skeleton-containing polymer compound in this solution was measured by GPC, consequently finding a weight average molecular weight of 30,000 in terms of polystyrene. The polymer compound corresponds to the general formula (24) wherein a'=0.220, b'=0.080, c'=0, d'=0, e'=0, f'=0, g'=0.513, h'=0.187, and X' and U are as follows.

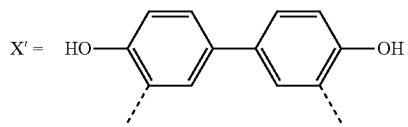

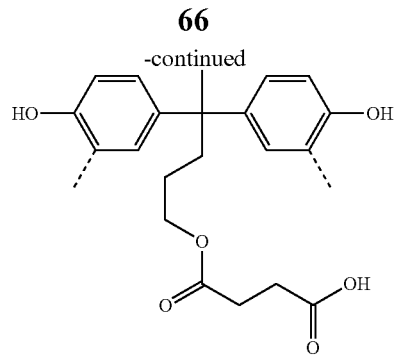

[Synthesis Example 9] Synthesis of Silicone Skeleton-Containing Polymer Compound (A-4)

A silicone skeleton-containing polymer compound was synthesized in the same manner as in Synthesis Example 6 except that 188 g of compound (M-9) was used in place of 85 g of compound (M-7), and cyclopentanone was added thereto as the main solvent to obtain a solution containing the silicone skeleton-containing polymer compound (A-4). The molecular weight of the silicone skeleton-containing polymer compound in this solution was measured by GPC, consequently finding a weight average molecular weight of 26,000 in terms of polystyrene. The polymer compound corresponds to the general formula (24) wherein a'=0.220, b'=0.080, c'=0, d'=0, e'=0, f'=0, g'=0.513, h'=0.187, and X' and U are as follows.

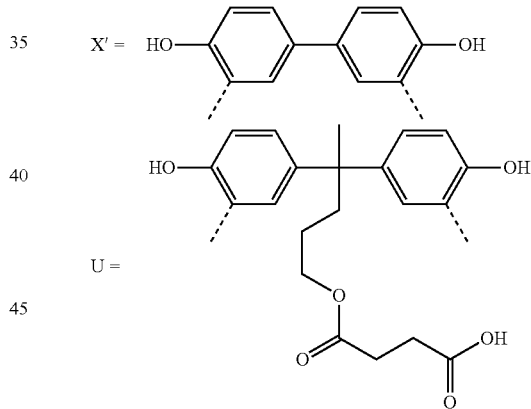

[Synthesis Example 10] Synthesis of Silicone Skeleton-Containing Polymer Compound (A-5)

A silicone skeleton-containing polymer compound was synthesized in the same manner as in Synthesis Example 6 except that 141 g of compound (M-10) was used in place of 85 g of compound (M-7), and cyclopentanone was added thereto as the main solvent to obtain a solution containing the silicone skeleton-containing polymer compound (A-5). The molecular weight of the silicone skeleton-containing polymer compound in this solution was measured by GPC, consequently finding a weight average molecular weight of 10,000 in terms of polystyrene. The polymer compound corresponds to the general formula (24) wherein a'=0.220, b'=0.080, c'=0, d'=0, e'=0, f'=0, g'=0.513, h'=0.187, and X' and U are as follows.

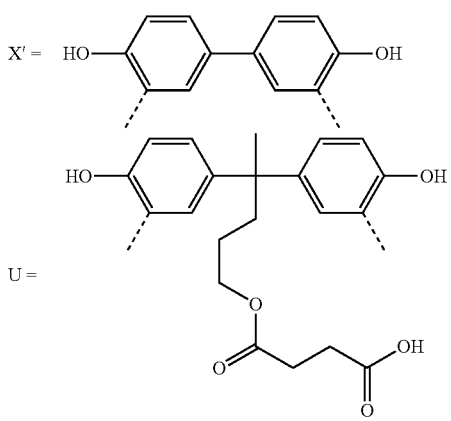

[Synthesis Example 11] Synthesis of Silicone Skeleton-Containing Polymer Compound (A-6)

A 3-L flask equipped with a stirrer, thermometer, nitrogen purge system, and reflux condenser was charged with 411 g of toluene and 120 g of compound (M-1) to make a solution. To the solution were added 45 g of compound (M-3), 24 g of compound (M-4), and 219 g of compound (M-9), and the resulting mixture was heated at 60° C. Thereafter, 1.3 g of carbon carried platinum catalyst (5% by mass) was added thereto, and the mixture was heated at 90° C. and aged for 3 hours. Then, the mixture was cooled to 60° C., 1.3 g of carbon carried platinum catalyst (5% by mass) was added again, and 73 g of compound (M-11) was dropped into the flask over 30 minutes. At this time, the temperature inside the flask was increased to 65 to 67° C. After dropwise addition, the mixture was further aged at 90° C. for 3 hours, and cooled to room temperature. Then, 780 g of methyl isobutyl ketone was added to the reaction solution, and this reaction solution was filtrated under pressure through a filter to remove the platinum catalyst. Further, to the obtained solution containing a silicone skeleton-containing polymer compound was added 780 g of pure water, and the mixture was stirred, allowed to stand, and separated to remove the lower aqueous layer. This liquid separation and water-washing operation was repeated 6 times to remove trace amounts of acid component in the silicone skeleton-containing polymer compound. The solvent in the resulting silicone skeleton-containing polymer compound solution was distilled off under reduced pressure and instead, 1050 g of tetrahydrofuran was added thereto, and the tetrahydrofuran solution was concentrated under reduced pressure so as to have a solid concentration of 30% by mass.

Then, a 3-L flask equipped with a stirrer, thermometer, nitrogen purge system, and reflux condenser was charged with 1500 g of the above-mentioned tetrahydrofuran solution containing 30% by mass of the silicone skeleton-containing polymer compound; and 31 g of succinic anhydride and 32 g of triethylamine were added thereto, followed by heating at 50° C. After stirring for 2 hours, the mixture was cooled to room temperature, and 900 g of saturated aqueous ammonium chloride solution and 1500 g of ethyl acetate were added thereto to terminate the reaction. Then, the aqueous layer was removed, and liquid separation and water-washing was repeated 5 times with 900 g of ultrapure water. The solvent of the collected organic layer was distilled off and instead, 600 g of cyclopentanone was added thereto, and the resulting cyclopentanone solution was concentrated under reduced pressure so as to have a solid concentration of 40 to 50% by mass, thereby obtaining a solution containing a silicone skeleton-containing polymer compound having carboxylic acid (A-6) and cyclopentanone as the main solvent. The molecular weight of the silicone skeleton-containing polymer compound in this solution was measured by GPC, consequently finding a weight average molecular weight of 24,000 in terms of polystyrene. The polymer compound corresponds to the general formula (1) wherein a=0.293, b=0.107, c=0, d=0, e=0, f=0, g=0.440, h=0.160, and X and U are as follows.

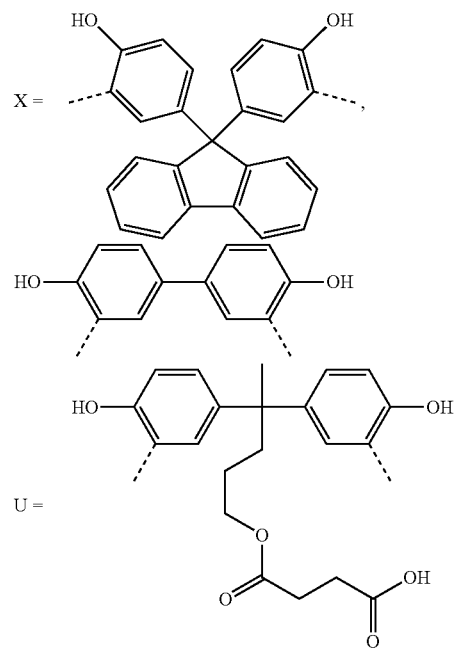

[Synthesis Example 12] Synthesis of Silicone Skeleton-Containing Polymer Compound (A-7)

A silicone skeleton-containing polymer compound was synthesized in the same manner as in Synthesis Example 11 except that 17 g of compound (M-5) was used in place of 24 g of compound (M-4), and cyclopentanone was added thereto as the main solvent to obtain a solution containing the silicone skeleton-containing polymer compound (A-7). The molecular weight of the silicone skeleton-containing polymer compound in this solution was measured by GPC, consequently finding a weight average molecular weight of 23,000 in terms of polystyrene. The polymer compound corresponds to the general formula (1) wherein a=0.293, b=0.107, c=0, d=0, e=0, f=0, g=0.440, h=0.160, and X and U are as follows.

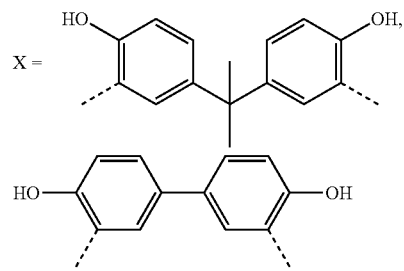

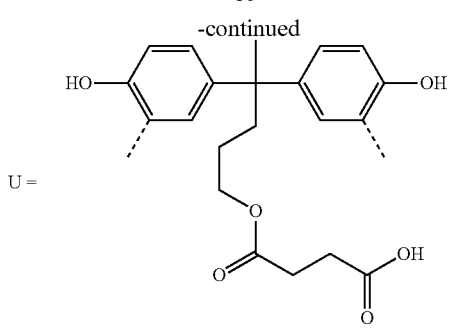

[Synthesis Example 13] Synthesis of Silicone Skeleton-Containing Polymer Compound (A-8)

A silicone skeleton-containing polymer compound was synthesized in the same manner as in Synthesis Example 11 except that 24 g of compound (M-6) was used in place of 24 g of compound (M-4), and cyclopentanone was added thereto as the main solvent to obtain a solution containing the silicone skeleton-containing polymer compound (A-8). The molecular weight of the silicone skeleton-containing polymer compound in this solution was measured by GPC, consequently finding a weight average molecular weight of 23,000 in terms of polystyrene. The polymer compound corresponds to the general formula (24) wherein a'=0.220, b'=0.080, c'=0.073, d'=0.027, e'=0, f'=0, g'=0.440, h'=0.160, and X', Y, and U are as follows.

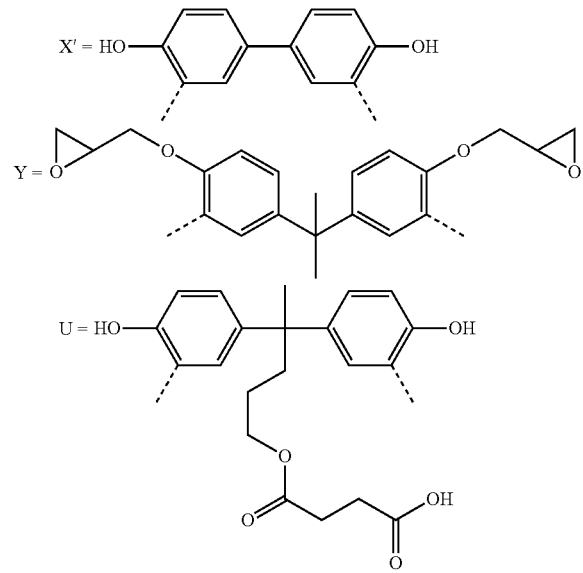

[Synthesis Example 14] Synthesis of Silicone Skeleton-Containing Polymer Compound (A-9)

A silicone skeleton-containing polymer compound was synthesized in the same manner as in Synthesis Example 6 except that 131 g of compound (M-2) was used in place of 120 g of compound (M-1), and cyclopentanone was added thereto as the main solvent to obtain a solution containing the silicone skeleton-containing polymer compound (A-9). The molecular weight of the silicone skeleton-containing polymer compound in this solution was measured by GPC, consequently finding a weight average molecular weight of 10,000 in terms of polystyrene. The polymer compound corresponds to the general formula (24) wherein a'=0.220, b'=0.080, c'=0, d'=0, e'=0, f'=0, g'=0.513, h'=0.187, and X' and U are as follows.

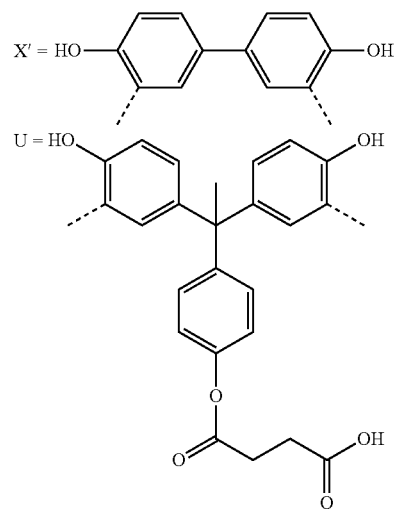

[Synthesis Example 15] Synthesis of Silicone Skeleton-Containing Polymer Compound (A-10)

A silicone skeleton-containing polymer compound was synthesized in the same manner as in Synthesis Example 6 except that 48 g of cyclchexyldicarboxylic anhydride was used in place of 31 g of succinic anhydride, and cyclopentanone was added thereto as the main solvent to obtain a solution containing the silicone skeleton-containing polymer compound (A-10). The molecular weight of the silicone skeleton-containing polymer compound in this solution was measured by GPC, consequently finding a weight average molecular weight of 10,000 in terms of polystyrene. The polymer compound corresponds to the general formula (24) wherein a'=0.220, b'=0.080, c'=0, d'=0, e'=0, f'=0, g'=0.513, h'=0.187, and X' and U are as follows.

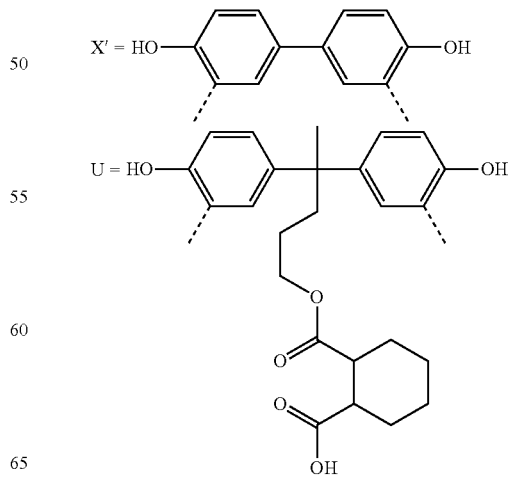

[Synthesis Example 16] Synthesis of Silicone Skeleton-Containing Polymer Compound (A-11)

A silicone skeleton-containing polymer compound was synthesized in the same manner as in Synthesis Example 6 except that 51 g of 5-norbornene-2,3-dicarboxylic anhydride was used in place of 31 g of succinic anhydride, and cyclopentanone was added thereto as the main solvent to obtain a solution containing the silicone skeleton-containing polymer compound (A-11). The molecular weight of the silicone skeleton-containing polymer compound in this solution was measured by GPC, consequently finding a weight average molecular weight of 10,000 in terms of polystyrene. The polymer compound corresponds to the general formula (24) wherein a'=0.220, b'=0.080, c'=0, d'=0, e'=0, f'=0, g'=0.513, h'=0.187, and X' and U are as follows.

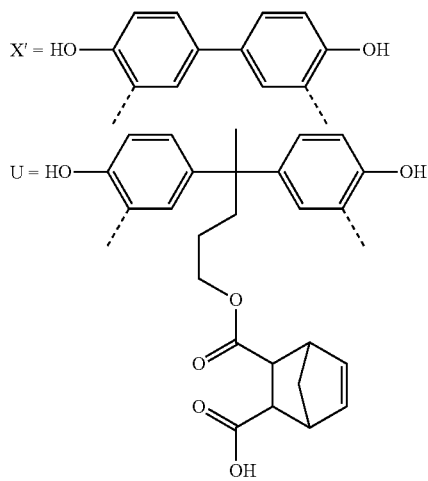

[Synthesis Example 17] Synthesis of Silicone Skeleton-Containing Polymer Compound (A-12)

A 3-L flask equipped with a stirrer, thermometer, nitrogen purge system, and reflux condenser was charged with 350 g of toluene and 171 g of compound (M-1) to make a solution. To the solution was added 85 g of compound (M-7), and the resulting mixture was heated at 60° C. Thereafter, 1.1 g of carbon carried platinum catalyst (5% by mass) was added thereto, and the mixture was heated at 90° C. and aged for 3 hours. Then, the mixture was cooled to 60° C., 1.1 g of carbon carried platinum catalyst (5% by mass) was added again, and 62 g of compound (M-11) was dropped into the flask over 30 minutes. At this time, the temperature inside the flask was increased to 65 to 67° C. After dropwise addition, the mixture was further aged at 90° C. for 3 hours, and cooled to room temperature. Then, 780 g of methyl isobutyl ketone was added to the reaction solution, and this reaction solution was filtrated under pressure through a filter to remove the platinum catalyst. Further, to the obtained solution containing a silicone skeleton-containing polymer compound was added 780 g of pure water, and the mixture was stirred, allowed to stand, and separated to remove the lower aqueous layer. This liquid separation and water-washing operation was repeated 6 times to remove trace amounts of acid component in the silicone skeleton-containing polymer compound. The solvent in the resulting silicone skeleton-containing polymer compound solution was distilled off under reduced pressure and instead, 750 g of tetrahydrofuran was added thereto, and the tetrahydrofuran solution was concentrated under reduced pressure so as to have a solid concentration of 30% by mass.

Then, a 3-L flask equipped with a stirrer, thermometer, nitrogen purge system, and reflux condenser was charged with 1000 g of the above-mentioned tetrahydrofuran solution containing 30% by mass of the silicone skeleton-containing polymer compound; and 32 g of succinic anhydride and 33 g of triethylamine were added thereto, followed by heating at 50° C. After stirring for 2 hours, the mixture was cooled to room temperature, and 900 g of saturated aqueous ammonium chloride solution and 1500 g of ethyl acetate were added thereto to terminate the reaction. Then, the aqueous layer was removed, and liquid separation and water-washing was repeated 5 times with 900 g of ultrapure water. The solvent of the collected organic layer was distilled off and instead, 600 g of cyclopentanone was added thereto, and the resulting cyclopentanone solution was concentrated under reduced pressure so as to have a solid concentration of 40 to 50% by mass, thereby obtaining a solution containing a silicone skeleton-containing polymer compound having carboxylic acid (A-12) and cyclopentanone as the main solvent. The molecular weight of the silicone skeleton-containing polymer compound in this solution was measured by GPC, consequently finding a weight average molecular weight of 10,000 in terms of polystyrene. The polymer compound corresponds to the general formula (1) wherein a=0, b=0, c=0, d=0, e=0.220, f=0.080, g=0.513, h=0.187, and W and U are as follows.

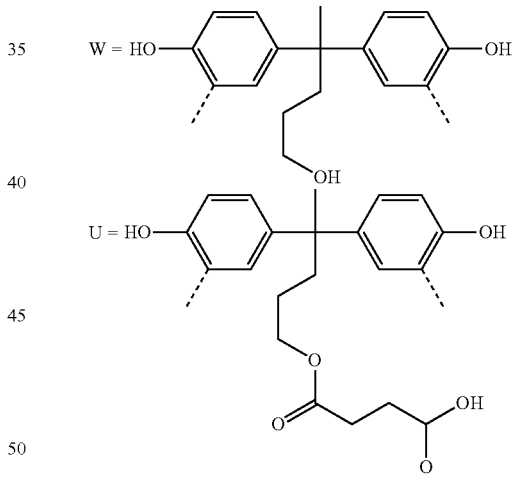

[Synthesis Example 18] Synthesis of Silicone Skeleton-Containing Polymer Compound (A-13)

A silicone skeleton-containing polymer compound was synthesized in the same manner as in Synthesis Example 17 except that 46 g of succinic anhydride and 46 g of triethylamine were used in place of 32 g of succinic anhydride and 33 g of triethylamine respectively, and cyclopentanone was added thereto as the main solvent to obtain a solution containing the silicone skeleton-containing polymer compound (A-13). The molecular weight of the silicone skeleton-containing polymer compound in this solution was measured by GPC, consequently finding a weight average molecular weight of 10,000 in terms of polystyrene. The polymer compound corresponds to the general formula (1) wherein a=0, b=0, c=0, d=0, e=0, f=0, g=0.733, h=0.267, and U is as follows.

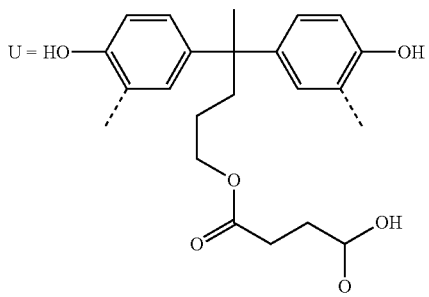

The solutions of the silicone skeleton-containing polymer compounds (A-1) to (A-13) synthesized in Synthesis Examples 6 to 18 were used. Each of the solutions was blended with a crosslinking agent, a photosensitive acid generator, a basic compound, and cyclopentanone as an additional solvent, with the composition and the blending ratio as shown in Table 1, to prepare a resist composition with a concentration of 45% by mass in terms of the resin. Thereafter, the composition was stirred, mixed, dissolved, and then filtrated through a 0.5 μm filter made of Teflon (registered trade mark) for microfiltration to obtain a desired resist composition.

TABLE 1

| | Silicone skeleton-containing polymer compound | Photo-sensitive acid generator | Cross-linking agent | Cross-linking agent | Basic compound |
|---|---|---|---|---|---|
| Resist composition 1 | A-1 (100 parts by mass) | PAG-1 (1.0 part by mass) | XL-1 (10.0 parts by mass) | XL-2 (15.0 parts by mass) | Amine-1 (0.2 part by mass) |
| Resist composition 2 | A-2 (100 parts by mass) | PAG-1 (1.0 part by mass) | XL-1 (10.0 parts by mass) | XL-2 (15.0 parts by mass) | Amine-1 (0.2 part by mass) |
| Resist composition 3 | A-3 (100 parts by mass) | PAG-1 (1.0 part by mass) | XL-1 (10.0 parts by mass) | XL-2 (15.0 parts by mass) | Amine-1 (0.2 part by mass) |
| Resist composition 4 | A-4 (100 parts by mass) | PAG-1 (1.0 part by mass) | XL-1 (10.0 parts by mass) | XL-2 (15.0 parts by mass) | Amine-1 (0.2 part by mass) |
| Resist composition 5 | A-5 (100 parts by mass) | PAG-1 (1.0 part by mass) | XL-1 (10.0 parts by mass) | XL-2 (15.0 parts by mass) | Amine-1 (0.2 part by mass) |
| Resist composition 6 | A-6 (100 parts by mass) | PAG-1 (1.0 part by mass) | XL-1 (10.0 parts by mass) | XL-2 (15.0 parts by mass) | Amine-1 (0.2 part by mass) |
| Resist composition 7 | A-7 (100 parts by mass) | PAG-1 (1.0 part by mass) | XL-1 (10.0 parts by mass) | XL-2 (15.0 parts by mass) | Amine-1 (0.2 part by mass) |
| Resist composition 8 | A-8 (100 parts by mass) | PAG-1 (1.0 part by mass) | XL-1 (10.0 parts by mass) | XL-2 (15.0 parts by mass) | Amine-1 (0.2 part by mass) |
| Resist composition 9 | A-9 (100 parts by mass) | PAG-1 (1.0 part by mass) | XL-1 (10.0 parts by mass) | XL-2 (15.0 parts by mass) | Amine-1 (0.2 part by mass) |
| Resist composition 10 | A-10 (100 parts by mass) | PAG-1 (1.0 part by mass) | XL-1 (10.0 parts by mass) | XL-2 (15.0 parts by mass) | Amine-1 (0.2 part by mass) |
| Resist composition 11 | A-11 (100 parts by mass) | PAG-1 (1.0 part by mass) | XL-1 (10.0 parts by mass) | XL-2 (15.0 parts by mass) | Amine-1 (0.2 part by mass) |
| Resist composition 12 | A-12 (100 parts by mass) | PAG-1 (1.0 part by mass) | XL-1 (10.0 parts by mass) | XL-2 (15.0 parts by mass) | Amine-1 (0.2 part by mass) |
| Resist composition 13 | A-13 (100 parts by mass) | PAG-1 (1.0 part by mass) | XL-1 (10.0 parts by mass) | XL-2 (15.0 parts by mass) | Amine-1 (0.2 part by mass) |

In Table 1, XL-2 represents EOCN-1020-55 (available from Nippon Kayaku Co., Ltd), and Photosensitive acid generator (PAG-1), Crosslinking agent (XL-1), and Basic compound (Amine-1) are shown below.

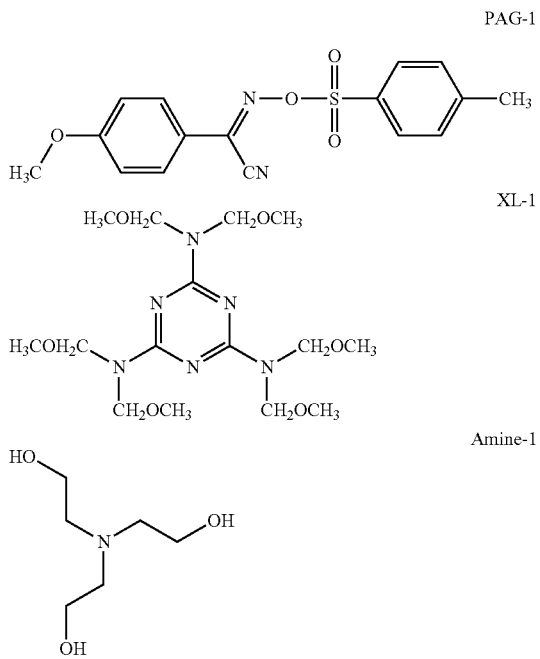

II. Exposure and Pattern Formation

Each of the resist compositions 1 to 13 (5 mL) was dispensed on a silicon substrate, and then the substrate was rotated to apply the resist composition by spin coating so as to give a film thickness of 20 μm.

Then, pre-bake was carried out on a hot plate at 100° C. for 2 minutes. Subsequently, this substrate was mounted with a mask capable of forming 20 μm holes arranged in 1:1 lengthwise and breadthwise, and exposed to a broad band light by using Mask Aligner MA-8 (manufactured by SUSS Micro Tec AG). After the exposure, the substrate was heated at 110° C. for 2 minutes (PEB), and then cooled. Thereafter, patterning was carried out by repeating one-minute puddle development three times using a 2.38% tetramethyl ammonium hydroxide aqueous solution as a developer. Then, the pattern formed on the substrate was post-cured with an oven at 180° C. for 2 hours while purging therein with nitrogen.

In a similar manner, a pattern is formed on a SiN substrate and on a Cu substrate in place of the silicon substrate.

Next, each substrate was cut-out so that the shape of the obtained hole pattern can be observed. The shape of the hole pattern was observed by using a scanning electron microscope (SEM). The optimum exposure dose (converted to an exposure dose of 365 nm light) to give an aperture diameter of the hole pattern equal to the mask size of 20 μm is shown in Table 2. The observed shape is also shown in Table 2.

TABLE 2

|  |  | Pattern profile and exposure dose (mJ) on silicon substrate | Pattern profile and exposure dose (mJ) on SiN substrate | Pattern profile and exposure dose (mJ) on Cu substrate |
|---|---|---|---|---|
| Example 1 | Resist composition 1 | Rectangular 600 | Forward tapered 650 | Forward tapered 650 |
| Example 2 | Resist composition 2 | Forward tapered 700 | Forward tapered 750 | Forward tapered 750 |
| Example 3 | Resist composition 3 | Forward tapered 700 | Forward tapered 750 | Forward tapered 750 |
| Example 4 | Resist composition 4 | Rectangular 400 | Forward tapered 450 | Forward tapered 450 |
| Example 5 | Resist composition 5 | Rectangular 600 | Forward tapered 650 | Forward tapered 650 |
| Example 6 | Resist composition 6 | Rectangular 400 | Forward tapered 450 | Forward tapered 450 |
| Example 7 | Resist composition 7 | Rectangular 400 | Forward tapered 450 | Forward tapered 450 |
| Example 8 | Resist composition 8 | Rectangular 400 | Forward tapered 450 | Forward tapered 450 |
| Example 9 | Resist composition 9 | Rectangular 600 | Forward tapered 650 | Forward tapered 650 |
| Example 10 | Resist composition 10 | Rectangular 600 | Forward tapered 650 | Forward tapered 650 |
| Example 11 | Resist composition 11 | Rectangular 600 | Forward tapered 650 | Forward tapered 650 |
| Example 12 | Resist composition 12 | Forward tapered 600 | Forward tapered 650 | Forward tapered 650 |
| Example 13 | Resist composition 13 | Forward tapered 600 | Forward tapered 650 | Forward tapered 650 |

As shown in Table 2, resist compositions 1 to 13 which contains the silicone skeleton-containing polymer compound of the present invention could form a pattern having a good profile on any of silicon substrate, SiN substrate, and Cu substrate without remarkable delamination of the pattern by using a 2.38% tetramethyl ammonium hydroxide aqueous solution as a developer.

III. Production of Photo-Curable Dry Film

For photo-curable dry film, solutions of the silicone skeleton-containing polymer compounds (A-1) to (A-13) synthesized in Synthesis Examples 6 to 18, were blended with a crosslinking agent, a photosensitive acid generator, and a basic compound, with the composition and the blending ratio as shown in Table 1, in the same manner as above except using no additional cyclopentanone. Thereafter, they were stirred, mixed, dissolved, and then filtrated through a 1.0 μm filter made of Teflon (registered trade mark) for microfiltration to obtain resist compositions 1' to 13'.

By using a die coater as a film coater and a polyethylene terephthalate film (thickness of 38 μm) as a supporting film, resist compositions 1' to 13' were each applied onto the supporting film so as to give a thickness of 50 μm. Then, each was passed through a hot-air circulating oven (length of 4 m) at 100° C. over 5 minutes to form a photo-curable resin layer on the supporting film. Thereafter, a polyethylene film (thickness of 50 μm) was laminated as a top coat film onto the photo-curable resin layer by using a laminate roll under pressure of 1 MPa to obtain photo-curable dry films 1 to 13.

Meanwhile, the thickness of the photo-curable resin layer was 50 μm. The film examples were shown in Table 3 as Examples.

IV. Exposure and Pattern Formation

The top coat film of respective photo-curable dry films 1 to 13 obtained as mentioned above was delaminated. Then, the photo-curable resin layer on the supporting film was brought into close contact with a silicon substrate at 100° C. by using a vacuum laminator TEAM-100RF (manufactured by Takatori Corp.) with a vacuum degree in the vacuum chamber of 100 Pa. After the pressure was resumed to normal pressure, the substrate was cooled to 25° C., taken out from the vacuum laminator, and then, the supporting film was delaminated.

After delamination of the supporting film, pre-bake was carried out on a hot plate at 100° C. for 5 minutes. Then, this substrate was mounted with a mask capable of forming 40 μm holes arranged in 1:1 lengthwise and breadthwise, and exposed to a broad band light by using Mask Aligner MA-8 (manufactured by SUSS Micro Tec AG). After the exposure, the substrate was heated at 130° C. for 5 minutes (PEB), and then cooled. Thereafter, patterning was carried out by repeating one-minute puddle development three times by using a 2.38% tetramethyl ammonium hydroxide aqueous solution as a developer. Then, the obtained pattern was post-cured by using an oven at 180° C. for 2 hours while purging therein with nitrogen.

The respective photo-curable dry films 1 to 13 thus produced were also laminated to a SiN substrate and on a Cu substrate in place of the silicon substrate, and a pattern was then formed in a similar manner as mentioned above.

Next, each substrate was cut-out so that the shape of the obtained hole pattern can be observed. The shape of the hole pattern was observed by using a scanning electron microscope (SEM). The optimum exposure dose (converted to an exposure dose of 365 nm light) to give an aperture diameter of the hole pattern equal to the mask size of 40 μm is shown in Table 3. The observed shape is also shown in Table 3.

exposure dose (365 nm wavelength) shown in Table 4 by using Mask Aligner MA-8 (manufactured by SUSS Micro Tec AG). After the exposure, the substrate was heated at 110° C. for 5 minutes (PEB), and then cooled. Thereafter, one-minute puddle development was repeated three times by using a 2.38% tetramethyl ammonium hydroxide aqueous solution as a developer. Then, post-cure was performed by using an oven at 180° C. for 2 hours while purging therein with nitrogen. Each of the substrates thus obtained was diced to expose the cross section of the circular holes, and the cross section of the circular holes was observed by using a scanning electron microscope (SEM) to evaluate whether or not defects were present. The results are shown in Table 4.

TABLE 3

| | Photo-curable dry film | Pattern profile and exposure dose (mJ) on silicon substrate | Pattern profile and exposure dose (mJ) on SiN substrate | Pattern profile and exposure dose (mJ) on Cu substrate |
|---|---|---|---|---|
| Example 14 | Photo-curable dry film 1 | Forward tapered 750 | Forward tapered 800 | Forward tapered 800 |
| Example 15 | Photo-curable dry film 2 | Forward tapered 850 | Forward tapered 900 | Forward tapered 900 |
| Example 16 | Photo-curable dry film 3 | Forward tapered 850 | Forward tapered 900 | Forward tapered 900 |
| Example 17 | Photo-curable dry film 4 | Forward tapered 550 | Forward tapered 600 | Forward tapered 600 |
| Example 18 | Photo-curable dry film 5 | Forward tapered 750 | Forward tapered 800 | Forward tapered 800 |
| Example 19 | Photo-curable dry film 6 | Forward tapered 550 | Forward tapered 600 | Forward tapered 600 |
| Example 20 | Photo-curable dry film 7 | Forward tapered 550 | Forward tapered 600 | Forward tapered 600 |
| Example 21 | Photo-curable dry film 8 | Forward tapered 550 | Forward tapered 600 | Forward tapered 600 |
| Example 22 | Photo-curable dry film 9 | Forward tapered 750 | Forward tapered 800 | Forward tapered 800 |
| Example 23 | Photo-curable dry film 10 | Forward tapered 750 | Forward tapered 800 | Forward tapered 800 |
| Example 24 | Photo-curable dry film 11 | Forward tapered 750 | Forward tapered 800 | Forward tapered 800 |
| Example 25 | Photo-curable dry film 12 | Forward tapered 750 | Forward tapered 800 | Forward tapered 800 |
| Example 26 | Photo-curable dry film 13 | Forward tapered 750 | Forward tapered 800 | Forward tapered 800 |

As shown in Table 3, photo-curable dry film 1 to 13 which uses the photo-curable resin composition containing the silicone skeleton-containing polymer compound of the present invention could form a pattern having a good profile on any of silicon substrate, SiN substrate, and Cu substrate without remarkable delamination of the pattern.

V. Fill-Up Performance

A 6-inch (150 mm) diameter silicon wafer having 200 circular holes each having an aperture diameter of 10 to 100 μm (pitch of 10 μm) and a depth of 10 to 120 μm (pitch of 10 μm) was prepared. Each top coat film of photo-curable dry films 1 to 5 and 12 was delaminated, and then, the photo-curable resin layer on the supporting film was brought into close contact with the substrate at 100° C. by using a vacuum laminator TEAM-100RF (manufactured by Takatori Corp.) with a vacuum degree in the vacuum chamber of 100 Pa. After the pressure was resumed to normal pressure, the substrate was cooled to 25° C., taken out from the vacuum laminator, and then, the supporting film was delaminated.

After delamination of the supporting film, pre-bake was carried out on a hot plate at 100° C. for 5 minutes. Then, the substrate was exposed to a broad band light with the

TABLE 4

| | Film Example | | Observation result |
|---|---|---|---|
| Examples | Photo-curable dry film | Exposure dose (mJ) | of circular hole cross section |
| Example 27 | Photo-curable dry film 1 | 700 | No defect Excellent fill-up |
| Example 28 | Photo-curable dry film 2 | 800 | No defect Excellent fill-up |
| Example 29 | Photo-curable dry film 3 | 800 | No defect Excellent fill-up |
| Example 30 | Photo-curable dry film 4 | 600 | No defect Excellent fill-up |
| Example 31 | Photo-curable dry film 5 | 700 | No defect Excellent fill-up |
| Example 32 | Photo-curable dry film 12 | 700 | No defect Excellent fill-up |

As shown in Table 4, all the circular holes of the silicon wafer having the photo-curable dry film of the present invention adhered thereto were filled up without defect, and thus, it could be clarified that it is excellent in fill-up performance as a top coat to protect electric and electronic parts.

VI. Electric Characteristics (Dielectric Breakdown Strength)

Each top coat film of photo-curable dry films 1 to 5 and 12 with a film thickness of 50 μm was delaminated, and then, the photo-curable resin layer on the supporting film was brought into close contact with a substrate defined in JIS K 6249 at 100° C. The substrate was then cooled to room temperature, and the supporting film was delaminated. After delamination of the supporting film, pre-bake was carried out on a hot plate at 100° C. for 5 minutes. Further, the substrate was exposed to a broad band light with an exposure dose of 1,000 mJ/cm$^2$ (365 nm wavelength) by using the above-mentioned mask aligner via a quartz photomask, heated at 110° C. for 5 minutes (PEB), and then cooled. Thereafter, patterning was carried out by repeating one-minute puddle development three times by using a 2.38% tetramethyl ammonium hydroxide aqueous solution as a developer. Then, post-cure was performed by using an oven at 180° C. for 2 hours while purging therein with nitrogen to obtain a substrate for measurement of dielectric breakdown strength. The dielectric breakdown strength was measured in accordance with the measurement method defined in JIS K 6249. The results are shown in Table 5.

VII. Adhesiveness

Each top coat film of photo-curable dry films 1 to 5 and 12 with a film thickness of 50 μm was delaminated, and then, the photo-curable resin layer on the supporting film was brought into close contact with an untreated 6-inch (150 mm) silicon wafer at 100° C. by using a vacuum laminator with a vacuum degree in the vacuum chamber of 100 Pa. After the pressure was resumed to normal pressure, the substrate was cooled to 25° C., taken out from the vacuum laminator, and then, the supporting film was delaminated. After delamination of the supporting film, pre-bake was carried out on a hot plate at 100° C. for 5 minutes.

Then, the substrate was exposed to a broad band light with an exposure dose of 1,000 mJ/cm$^2$ (365 nm wavelength) by using the above-mentioned mask aligner via a quartz photomask, heated at 110° C. for 5 minutes (PEB), and then cooled. Thereafter, post-cure was carried out by using an oven at 180° C. for 2 hours while purging therein with nitrogen to obtain the wafer having a post-cured film.

The obtained wafer was cut out into a square having a size of 1×1 cm. Then, an aluminum pin with epoxy adhesive was fastened to the cut wafer by means of a dedicated jig. Thereafter, the assembly was heated with an oven at 150° C. for 1 hour to bond the aluminum pin to the wafer. After cooled to room temperature, initial adhesiveness was evaluated from the resistance force by using a thin-film adhesion strength measurement apparatus (Sebastian Five-A). Herein, the measurement was performed with a measurement rate of 0.2 kg/sec. FIG. 1 is an explanatory view of the method for measuring adhesiveness. In FIG. 1, reference number 1 denotes a silicon wafer (substrate), 2 denotes a cured film, 3 denotes an aluminum pin with adhesive, 4 denotes a support, 5 denotes a grip, and 6 denotes tensile direction. The obtained value is an average of 12 measurement points, and a larger value indicates a higher adhesion strength of the cured film to the substrate. Adhesiveness was evaluated by comparing the obtained values. The results were shown in Table 5.

VIII. Crack Resistance

Each top coat film of photo-curable dry films 1 to 5 and 12 with a film thickness of 50 μm was delaminated, and then, the photo-curable resin layer on the supporting film was brought into close contact with the same substrate as used in the fill-up performance test mentioned above, at 100° C. by using the above-mentioned vacuum laminator with a vacuum degree in the vacuum chamber of 100 Pa. After the pressure was resumed to normal pressure, the substrate was cooled to 25° C., taken out from the vacuum laminator, and then, the supporting film was delaminated.

After delamination of the supporting film, pre-bake was carried out on a hot plate at 100° C. for 5 minutes. Then, the substrate was exposed to a broad band light with an exposure dose of 1,000 mJ/cm$^2$ (365 nm wavelength) by using the above-mentioned mask aligner via a quartz photomask. Thereafter, one-minute puddle development was repeated three times by using a 2.38% tetramethyl ammonium hydroxide aqueous solution as a developer. Subsequently, post-cure was carried out by using an oven at 180° C. for 2 hours while purging therein with nitrogen.

This substrate having the cured film formed thereon was put into a thermal cycle tester with a temperature profile of −55° C. to +150° C. as one cycle, and subjected to 1,000 cycles to examine whether or not a crack was formed in the cured film. The results are shown in Table 5.

IX. Resistance to Removing Liquid

Each top coat film of photo-curable dry films 1 to 5 and 12 with a film thickness of 50 μm was delaminated, and then, the photo-curable resin layer on the supporting film was brought into close contact with an untreated 6-inch (150 mm) silicon wafer at 100° C. by using the above-mentioned vacuum laminator with a vacuum degree in the vacuum chamber of 100 Pa. After the pressure was resumed to normal pressure, the substrate was cooled to 25° C., taken out from the vacuum laminator, and then, the supporting film was delaminated.

After delamination of the supporting film, pre-bake was carried out on a hot plate at 100° C. for 5 minutes. Then, the substrate was exposed to a broad band light with an exposure dose of 1,000 mJ/cm$^2$ (365 nm wavelength) by using the above-mentioned mask aligner via a quartz photomask, heated at 110° C. for 5 minutes (PEB), and then cooled. Thereafter, one-minute puddle development was repeated three times by using a 2.38% tetramethyl ammonium hydroxide aqueous solution as a developer. Subsequently, post-cure was carried out by using an oven at 180° C. for 2 hours while purging therein with nitrogen to obtain a 15 mm×15 mm square pattern cured film.

This substrate was soaked in N-methylpyrrolidone (NMP) at room temperature for 1 hour, and then, the changes in appearance and film thickness were examined to evaluate resistance to the removing liquid. The results are shown in Table 5.

TABLE 5

| Film Example | Electric characteristics Dielectric breakdown strength (V/μm) | Adhesiveness (kg/cm$^2$) | Crack resistance (after thermal cycle test) | Resistance to removing liquid (after soaking in NMP) |
|---|---|---|---|---|
| Example 27 | 350 | 490 | No crack | No change in appearance and film thickness |
| Example 28 | 360 | 450 | No crack | No change in appearance and film thickness |
| Example 29 | 360 | 440 | No crack | No change in appearance and film thickness |

TABLE 5-continued

| Film Example | Electric characteristics Dielectric breakdown strength (V/μm) | Adhesive- ness (kg/cm²) | Crack resistance (after thermal cycle test) | Resistance to removing liquid (after soaking in NMP) |
|---|---|---|---|---|
| Example 30 | 340 | 480 | No crack | No change in appearance and film thickness |
| Example 31 | 350 | 450 | No crack | No change in appearance and film thickness |
| Example 32 | 340 | 500 | No crack | No change in appearance and film thickness |

As shown in Table 5, the cured film obtained by patterning using the photo-curable dry film of the present invention was excellent all in electric characteristics, adhesiveness, crack resistance, and resistance to removing liquid, as a top coat to protect electric and electronic parts.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A silicone skeleton-containing polymer compound comprising a repeating unit shown by the general formula (1) and having a weight average molecular weight of 3,000 to 500,000,

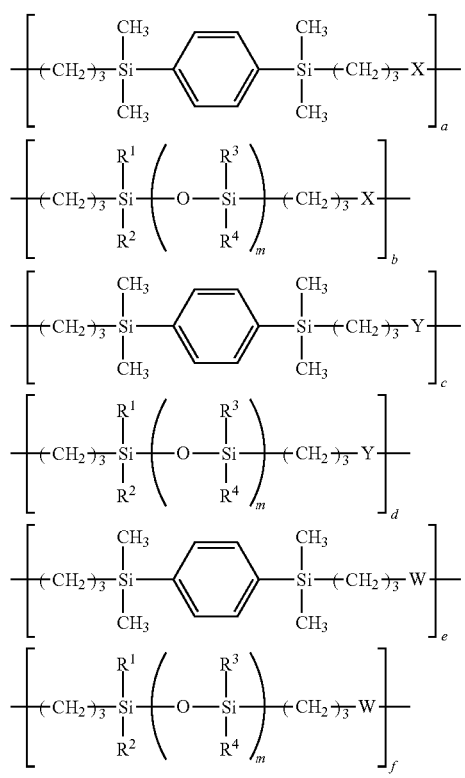

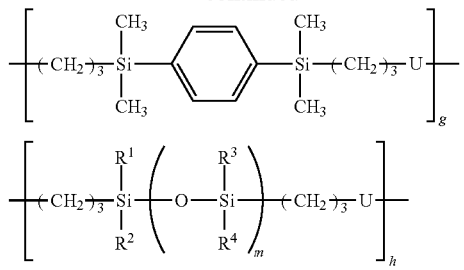

wherein $R^1$ to $R^4$ may be the same or different and represent a monovalent hydrocarbon group having 1 to 8 carbon atoms; "m" is an integer of 1 to 100; "a", "b", "c", "d", "e", and "f" are each 0 or a positive number, and "g" and "h" are each a positive number, provided that $a+b+c+d+e+f+g+h=1$; X is a divalent organic group shown by the general formula (2); Y is a divalent organic group shown by the general formula (3); W is a divalent organic group shown by the general formula (4); and U is a divalent organic group shown by the general formula (5),

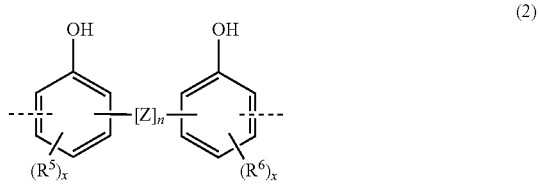

wherein Z represents a divalent organic group selected from any of

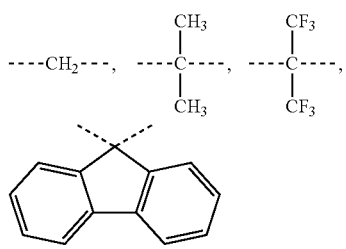

the dotted line represents a bond; "n" is 0 or 1; $R^5$ and $R^6$ each represent an alkyl group or alkoxy group having 1 to 4 carbon atoms and may be the same or different; and "x" is 0, 1, or 2;

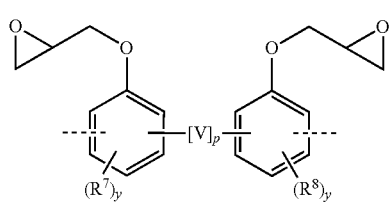

wherein V represents a divalent organic group selected from any of

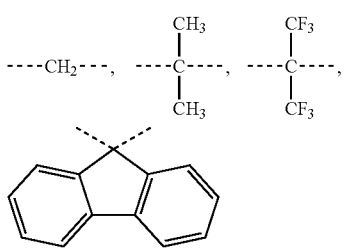

the dotted line represents a bond; "p" is 0 or 1; $R^7$ and $R^8$ each represent an alkyl group or alkoxy group having 1 to 4 carbon atoms and may be the same or different; and "y" is 0, 1, or 2;

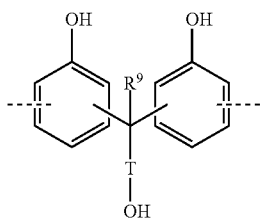
(4)

wherein the dotted line represents a bond; T represents an alkylene group having 1 to 10 carbon atoms or a divalent aromatic group; and $R^9$ represents a hydrogen atom or a methyl group;

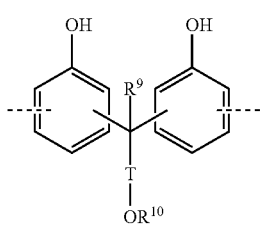
(5)

wherein the dotted line represents a bond; T and $R^9$ have the same meanings as defined above; and $R^{10}$ represents a monovalent carboxyl-containing organic group.

2. The silicone skeleton-containing polymer compound according to claim 1, wherein $R^{10}$ in the general formula (5) is a monovalent carboxyl-containing organic group shown by the general formula (6),

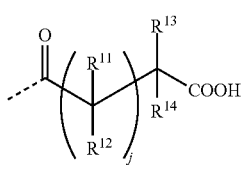
(6)

wherein the dotted line represents a bond; $R^{11}$ to $R^{14}$ may be the same or different and represent a hydrogen atom, a halogen atom, a linear, branched, or cyclic alkyl group having 1 to 12 carbon atoms, or an aromatic group; $R^{11}$ and $R^{13}$ may be bonded respectively to $R^{12}$ and $R^{14}$ to form a substituted or unsubstituted ring structure having 1 to 12 carbon atoms; and "j" is any of 1 to 7.

3. The silicone skeleton-containing polymer compound according to claim 2, wherein in the general formula (1), $0 \le a \le 0.5$, $0 \le b \le 0.3$, $0 \le c \le 0.5$, $0 \le d \le 0.3$, $0 \le e \le 0.8$, $0 \le f \le 0.5$, $0 < g \le 0.8$, and $0 < h \le 0.5$.

4. The silicone skeleton-containing polymer compound according to claim 3, wherein in the general formula (1), a=0, b=0, c=0, d=0, $0 \le e \le 0.3$, $0 \le f \le 0.2$, $0 < g \le 0.8$, and $0 < h \le 0.5$.

5. The silicone skeleton-containing polymer compound according to claim 2, wherein in the general formula (1), a=0, b=0, c=0, d=0, $0 \le e \le 0.3$, $0 \le f \le 0.2$, $0 < g \le 0.8$, and $0 < h \le 0.5$.

6. The silicone skeleton-containing polymer compound according to claim 1, wherein in the general formula (1), $0 \le a \le 0.5$, $0 \le b \le 0.3$, $0 \le c \le 0.5$, $0 \le d \le 0.3$, $0 \le e \le 0.8$, $0 \le f \le 0.5$, $0 < g \le 0.8$, and $0 < h \le 0.5$.

7. The silicone skeleton-containing polymer compound according to claim 6, wherein in the general formula (1), a=0, b=0, c=0, d=0, $0 \le e \le 0.3$, $0 \le f \le 0.2$, $0 < g \le 0.8$, and $0 < h \le 0.5$.

8. The silicone skeleton-containing polymer compound according to claim 1, wherein in the general formula (1), a=0, b=0, c=0, d=0, $0 \le e \le 0.3$, $0 \le f \le 0.2$, $0 < g \le 0.8$, and $0 < h \le 0.5$.

9. A method for producing the silicone skeleton-containing polymer compound according to claim 1, comprising:
introducing a carboxyl group by reacting a part or all of alcoholic or phenolic hydroxyl groups of a silicone skeleton-containing polymer compound having a repeating unit shown by the general formula (7) with a dicarboxylic acid anhydride,

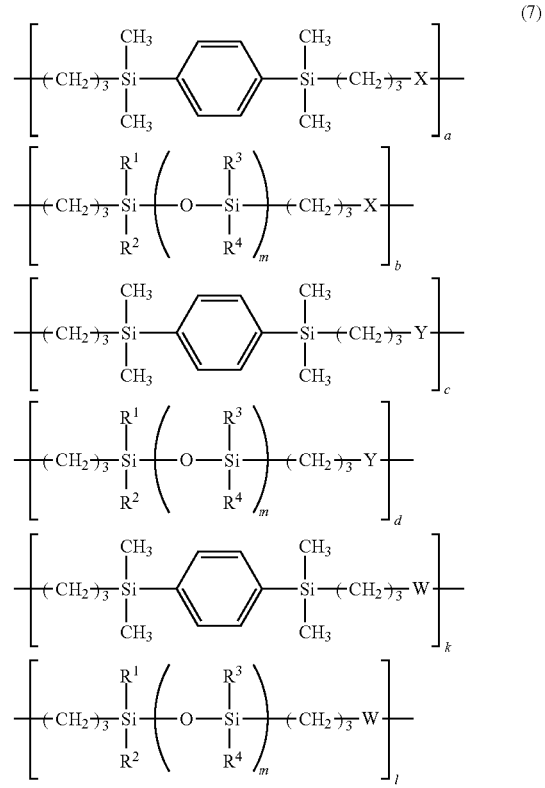
(7)

wherein $R^1$ to $R^4$, "a", "b", "c", "d", "m", X, Y, and W have the same meanings as defined above; "k" and "l" are each a positive number satisfying k=e+g and l=f+h; and "e", "f", "g", and "h" have the same meanings as defined above,
wherein the silicone skeleton-containing polymer compound shown by the general formula (7) is a polymer compound obtained by polymerization reaction of:
either or both of a hydrogensilphenylene shown by the structural formula (8) and a dihydroorganosiloxane shown by the general formula (9),

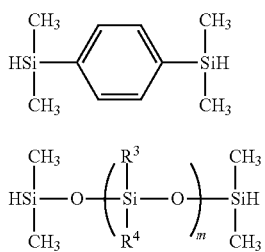
(8)

(9)

wherein $R^3$, $R^4$, and "m" have the same meanings as defined above;
either or both of a phenol compound having two allyl groups and shown by the general formula (10) and a compound having two allyl groups and shown by the general formula (11),

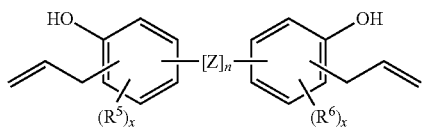
(10)

wherein Z, $R^5$, $R^6$, "n" and "x" have the same meanings as defined above,

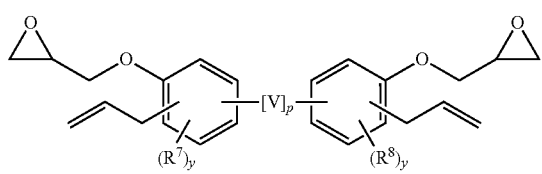
(11)

wherein V, $R^7$, $R^8$, "p" and "y" have the same meanings as defined above; and
a phenol compound having two allyl groups and shown by the general formula (12)

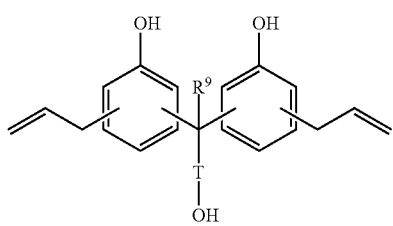
(12)

wherein T and $R^9$ have the same meanings as defined above; in the presence of a catalyst.

10. The method for producing the silicone skeleton-containing polymer compound according to claim 9, wherein the phenol compound having two allyl groups and shown by the general formula (12) is a compound shown by the general formula (13),

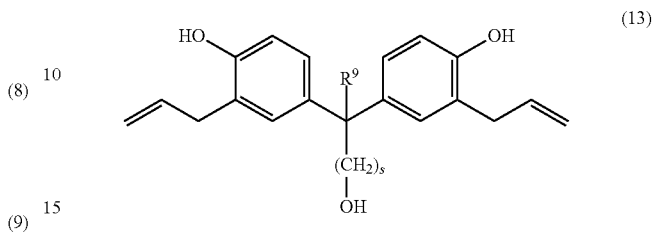
(13)

wherein $R^9$ has the same meaning as defined above, and "s" is a positive number of 1 to 12.

11. The method for producing the silicone skeleton-containing polymer compound according to claim 9, wherein the phenol compound having two allyl groups and shown by the general formula (12) is a compound shown by the general formula (14),

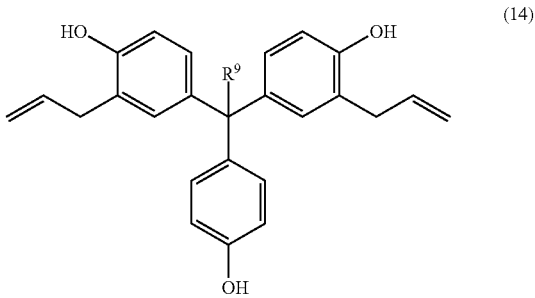
(14)

wherein $R^9$ has the same meaning as defined above.

12. A silicone skeleton-containing polymer compound comprising a repeating unit shown by the general formula (24) and having a weight average molecular weight of 3,000 to 500,000,

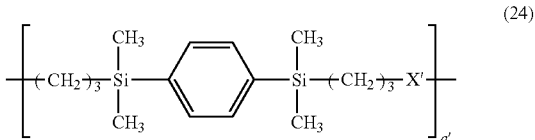
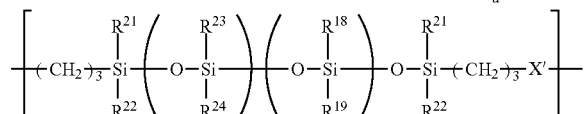
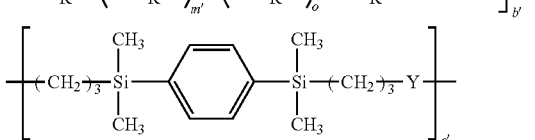
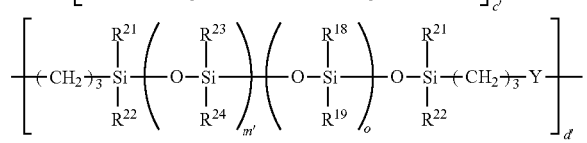
(24)

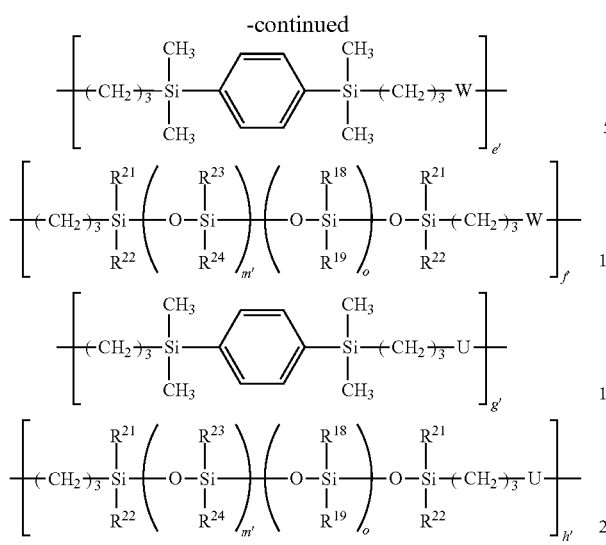

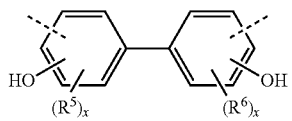

(25)

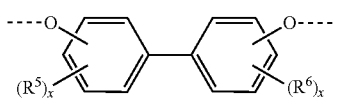

(26)

wherein the dotted line represents a bond; $R^5$ and $R^6$ each represent an alkyl group or alkoxy group having 1 to 4 carbon atoms and may be the same or different; and "x" is 0, 1, or 2;

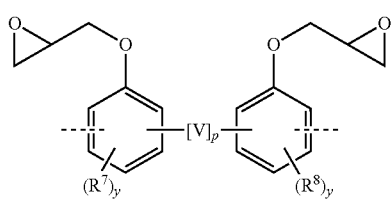

(3)

wherein V represents a divalent organic group selected from any of

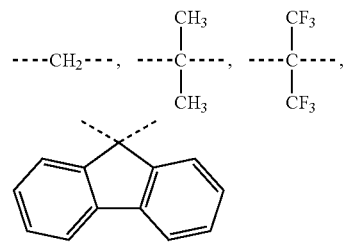

the dotted line represents a bond; "p" is 0 or 1; $R^7$ and $R^8$ each represent an alkyl group or alkoxy group having 1 to 4 carbon atoms and may be the same or different; and "y" is 0, 1, or 2;

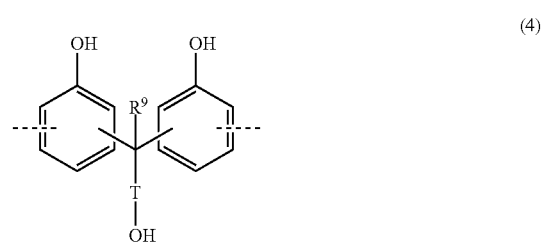

(4)

wherein the dotted line represents a bond; T represents an alkylene group having 1 to 10 carbon atoms or a divalent aromatic group; and $R^9$ represents a hydrogen atom or a methyl group;

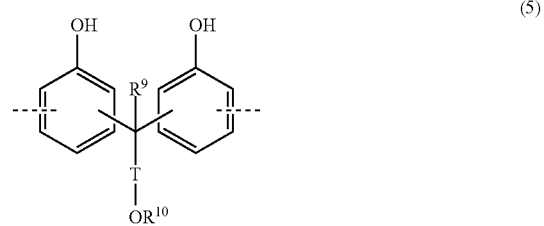

(5)

wherein the dotted line represents a bond; T and $R^9$ have the same meanings as defined above; and $R^{10}$ represents a monovalent carboxyl-containing organic group.

13. The silicone skeleton-containing polymer compound according to claim 12, wherein in the general formula (24), "o" is an integer of 1 to 100; $R^{21}$ to $R^{24}$ may be the same or different and represent a monovalent hydrocarbon group having 1 to 8 carbon atoms; $R^{18}$ represents a phenyl substituent containing a hydroxyl group or an alkoxy group and shown by the general formula (27); and $R^{19}$ may be the same as or different from $R^{21}$ to $R^{24}$ and represents a monovalent organic group having 1 to 10 carbon atoms and optionally containing an oxygen atom, or $R^{19}$ may be the same as or different from $R^{18}$ and represents a phenyl substituent containing a hydroxyl group or an alkoxy group and shown by the general formula (27),

(27)

wherein $R^{21}$ to $R^{24}$ may be the same or different and represent a monovalent organic group having 1 to 15 carbon atoms and optionally containing an oxygen atom; $R^{18}$ and $R^{19}$ may be the same or different and represent a monovalent organic group having 1 to 28 carbon atoms and optionally containing an oxygen atom; m' is an integer of 0 to 100; "o" is an integer of 0 to 100; c', d', e', and f' are each 0 or a positive number, and a', b', g' and h' are each a positive number, provided that a'+b'+c'+d'+e'+f'+g'+h'=1; X' is a divalent organic group shown by the general formula (25) or the general formula (26); Y is a divalent organic group shown by the general formula (3); W is a divalent organic group shown by the general formula (4); and U is a divalent organic group shown by the general formula (5), wherein "r" is an integer of 0 to 10; $R^{20}$ represents a hydroxyl group or a linear, branched, or cyclic alkoxy group having 1 to 12 carbon atoms.
14. The silicone skeleton-containing polymer compound according to claim 13, wherein the phenyl substituent shown by the general formula (27) is one group, or two or more groups selected from the formula (28),
(28)
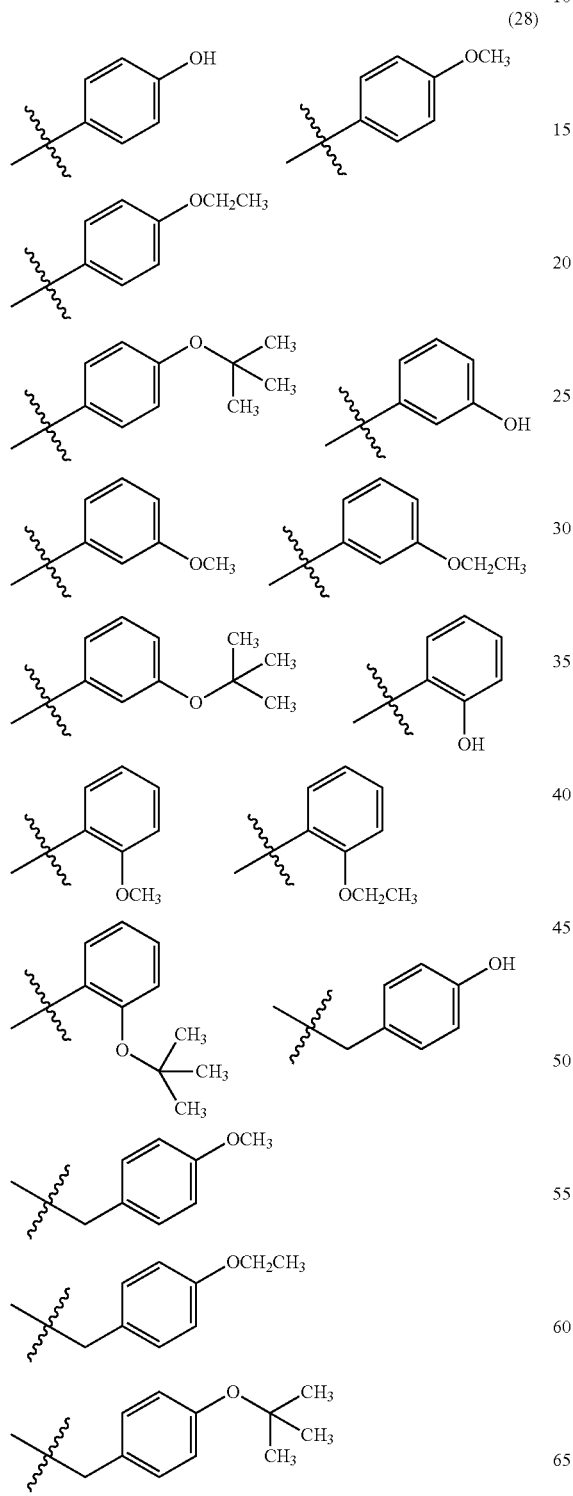
-continued
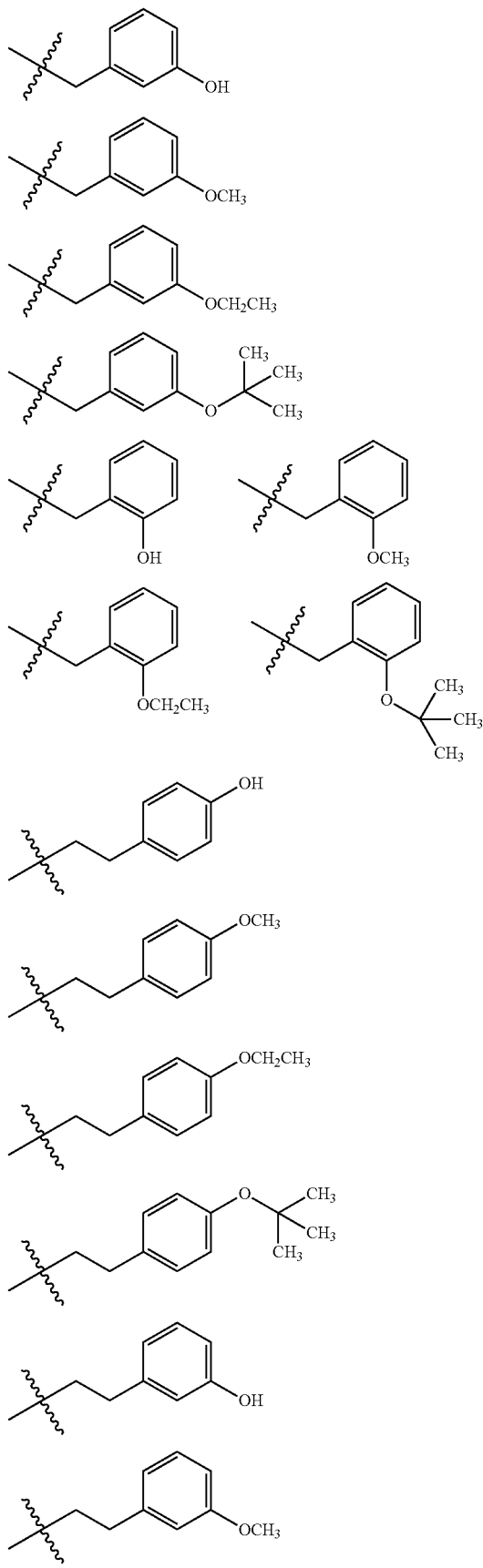

-continued

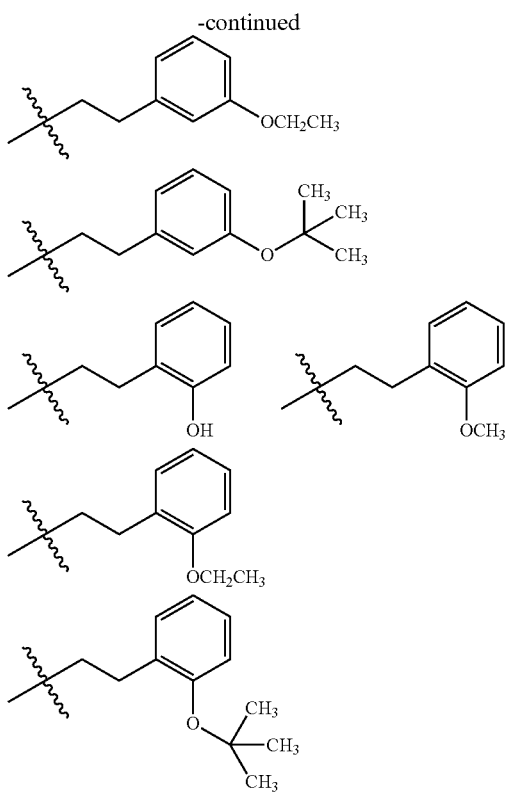

wherein the line with a wavy line represents a bonding arm.

15. A chemically amplified negative resist composition comprising:
(A) the silicone skeleton-containing polymer compound according to claim 1,
(B) a photosensitive acid generator capable of generating an acid by decomposition with light having a wavelength of 190 to 500 nm;
(C) one or more crosslinking agents selected from an amino condensate modified by formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted by a glycidyl group, a polyhydric phenol compound in which a hydrogen atom of a phenolic hydroxyl group is substituted by a substituent shown by the formula (C-1), and a compound having two or more nitrogen atoms bonded to a glycidyl group and shown by the formula (C-2),

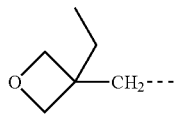 (C-1)

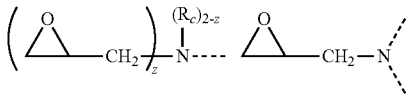 (C-2)

wherein the dotted line represents a bond; $R_c$ represents a linear, branched, or cyclic alkyl group having 1 to 6 carbon atoms; and "z" is 1 or 2;

(D) a solvent; and
(E) a basic compound.

16. A chemically amplified negative resist composition comprising:
(A) the silicone skeleton-containing polymer compound according to claim 12,
(B) a photosensitive acid generator capable of generating an acid by decomposition with light having a wavelength of 190 to 500 nm;
(C) one or more crosslinking agents selected from an amino condensate modified by formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted by a glycidyl group, a polyhydric phenol compound in which a hydrogen atom of a phenolic hydroxyl group is substituted by a substituent shown by the formula (C-1), and a compound having two or more nitrogen atoms bonded to a glycidyl group and shown by the formula (C-2),

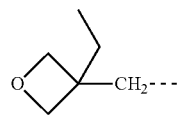 (C-1)

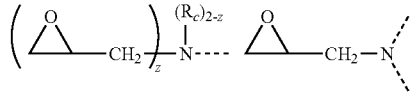 (C-2)

wherein the dotted line represents a bond; $R_c$ represents a linear, branched, or cyclic alkyl group having 1 to 6 carbon atoms; and "z" is 1 or 2;

(D) a solvent; and
(E) a basic compound.

17. A photo-curable dry film comprising a supporting film, a top coat film, and a photo-curable resin layer having a film thickness of 10 to 100 μm, the photo-curable resin layer being sandwiched between the supporting film and the top coat film, wherein the photo-curable resin layer is formed of the chemically amplified negative resist composition according to claim 15.

18. A photo-curable dry film comprising a supporting film, a top coat film, and a photo-curable resin layer having a film thickness of 10 to 100 μm, the photo-curable resin layer being sandwiched between the supporting film and the top coat film, wherein the photo-curable resin layer is formed of the chemically amplified negative resist composition according to claim 16.

19. A method for producing a photo-curable dry film, comprising:
(I) continuously applying the chemically amplified negative resist composition according to claim 15 onto a supporting film to form a photo-curable resin layer,
(II) continuously drying the photo-curable resin layer, and further
(III) laminating a top coat film onto the photo-curable resin layer.

20. A method for producing a photo-curable dry film, comprising:
(I) continuously applying the chemically amplified negative resist composition according to claim 16 onto a supporting film to form a photo-curable resin layer, (II) continuously drying the photo-curable resin layer, and further
(III) laminating a top coat film onto the photo-curable resin layer.

21. A patterning process comprising:
    (1) applying the chemically amplified negative resist composition according to claim 15 onto a substrate to form a photosensitive material film;
    (2) exposing the photosensitive material film to a high energy beam having a wavelength of 190 to 500 nm or an electron beam via a photomask after a heat treatment; and
    (3) subjecting to development with a developer after a heat treatment.

22. The patterning process according to claim 21, further comprising post-curing a patterned film formed by the development at 100 to 250° C. after the development.

23. A patterning process comprising:
    (1) applying the chemically amplified negative resist composition according to claim 16 onto a substrate to form a photosensitive material film;
    (2) exposing the photosensitive material film to a high energy beam having a wavelength of 190 to 500 nm or an electron beam via a photomask after a heat treatment; and
    (3) subjecting to development with a developer after a heat treatment.

24. The patterning process according to claim 23, further comprising post-curing a patterned film formed by the development at 100 to 250° C. after the development.

25. A patterning process comprising:
    (i) separating the top coat film from the photo-curable dry film according to claim 17 and bringing an exposed photo-curable resin layer into close contact with a substrate;
    (ii) exposing the photo-curable resin layer to a high energy beam having a wavelength of 190 to 500 nm or an electron beam via a photomask either through the supporting film or in a peeled-off state of the supporting film;
    (iii) subjecting to a heat treatment after the exposure; and
    (iv) subjecting to development with a developer.

26. The patterning process according to claim 25, wherein the substrate includes a trench and/or a hole each having an aperture width of 10 to 100 μm and a depth of 10 to 120 μm.

27. A patterning process comprising:
    (i) separating the top coat film from the photo-curable dry film according to claim 18 and bringing an exposed photo-curable resin layer into close contact with a substrate;
    (ii) exposing the photo-curable resin layer to a high energy beam having a wavelength of 190 to 500 nm or an electron beam via a photomask either through the supporting film or in a peeled-off state of the supporting film;
    (iii) subjecting to a heat treatment after the exposure; and
    (iv) subjecting to development with a developer.

28. The patterning process according to claim 27, wherein the substrate includes a trench and/or a hole each having an aperture width of 10 to 100 μm and a depth of 10 to 120 μm.

29. A layered product comprising a substrate including a trench and/or a hole each having an aperture width of 10 to 100 μm and a depth of 10 to 120 μm, and the photo-curable resin layer of the photo-curable dry film according to claim 17 laminated on the substrate.

30. A layered product comprising a substrate including a trench and/or a hole each having an aperture width of 10 to 100 μm and a depth of 10 to 120 μm, and the photo-curable resin layer of the photo-curable dry film according to claim 18 laminated on the substrate.

31. A layered product comprising:
    a substrate; and
    a patterned film laminated on the substrate, the patterned film being a cured product of the chemically amplified negative resist composition according to claim 15.

32. A layered product comprising:
    a substrate; and
    a patterned film laminated on the substrate, the patterned film being a cured product of the chemically amplified negative resist composition according to claim 16.

* * * * *